US008945876B2

(12) United States Patent
Su et al.

(10) Patent No.: US 8,945,876 B2
(45) Date of Patent: Feb. 3, 2015

(54) AUTO-PROCESSING DOMAINS FOR POLYPEPTIDE EXPRESSION

(71) Applicant: University Of Hawaii, Honolulu, HI (US)

(72) Inventors: Wei Wen Su, Honolulu, HI (US); Bei Zhang, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 13/683,869

(22) Filed: Nov. 21, 2012

(65) Prior Publication Data

US 2013/0131315 A1    May 23, 2013

Related U.S. Application Data

(60) Provisional application No. 61/563,508, filed on Nov. 23, 2011, provisional application No. 61/564,808, filed on Nov. 29, 2011.

(51) Int. Cl.
*C12N 9/00* (2006.01)
*C07K 14/00* (2006.01)
*C12P 21/00* (2006.01)
*C12N 15/82* (2006.01)

(52) U.S. Cl.
CPC ............. *C12P 21/00* (2013.01); *C12N 15/8201* (2013.01)
USPC .......................................... 435/69.7; 530/350

(58) Field of Classification Search
CPC ... A61K 39/11; C07K 2319/92; C12N 9/1007
USPC .......................................... 530/350; 435/69.7
See application file for complete search history.

(56) References Cited

U.S. PATENT DOCUMENTS

| | | | |
|---|---|---|---|
| 4,774,182 A | 9/1988 | Szybalski | |
| 5,846,767 A | 12/1998 | Halpin et al. | |
| 6,376,745 B1 | 4/2002 | Atabekov et al. | |
| 6,448,473 B1 | 9/2002 | Mitsky et al. | |
| 6,455,759 B1 | 9/2002 | Vierstra et al. | |
| 6,887,490 B1 | 5/2005 | Jahoda et al. | |
| 6,933,378 B2 | 8/2005 | Atabekov et al. | |
| 7,026,526 B2 | 4/2006 | Snell | |
| 7,326,567 B2 | 2/2008 | Saha | |
| 7,364,878 B2 | 4/2008 | Otte et al. | |
| 7,393,632 B2 | 7/2008 | Cheo et al. | |
| 7,642,404 B2 | 1/2010 | Werner et al. | |
| 7,692,065 B2 | 4/2010 | Harper et al. | |
| 7,741,530 B2 | 6/2010 | Snell | |
| 7,794,980 B2 | 9/2010 | Pietrokovski et al. | |
| 8,048,999 B2 | 11/2011 | Yamanaka et al. | |
| 8,058,065 B2 | 11/2011 | Yamanaka et al. | |
| 8,129,187 B2 | 3/2012 | Yamanaka et al. | |
| 2002/0129400 A1 | 9/2002 | Snell | |
| 2002/0132308 A1 | 9/2002 | Liu et al. | |
| 2002/0160378 A1 | 10/2002 | Harper et al. | |
| 2003/0108524 A1 | 6/2003 | Diagana et al. | |
| 2003/0182678 A1 | 9/2003 | Mitsky et al. | |
| 2004/0009476 A9 | 1/2004 | Harper et al. | |
| 2006/0026718 A1 | 2/2006 | Werner et al. | |
| 2006/0037099 A1 | 2/2006 | Werner et al. | |
| 2006/0183121 A1 | 8/2006 | Pietrokovski et al. | |
| 2006/0200869 A1 | 9/2006 | Naldini et al. | |
| 2006/0253936 A1 | 11/2006 | Liu et al. | |
| 2007/0065912 A1 | 3/2007 | Carson et al. | |
| 2007/0277263 A1 | 11/2007 | Anderson et al. | |
| 2008/0004228 A1 | 1/2008 | Berger et al. | |
| 2008/0115243 A1 | 5/2008 | Raab et al. | |
| 2008/0227151 A1 | 9/2008 | Otte et al. | |
| 2008/0227199 A1 | 9/2008 | Otte et al. | |
| 2008/0311623 A1 | 12/2008 | Saha | |
| 2009/0017496 A1 | 1/2009 | Ma et al. | |
| 2009/0092698 A1 | 4/2009 | Meyer | |
| 2009/0222936 A1 | 9/2009 | Richmond et al. | |
| 2010/0071085 A1 | 3/2010 | Lindbo | |
| 2010/0138948 A1 | 6/2010 | Werner et al. | |
| 2010/0178671 A1 | 7/2010 | Nguyen et al. | |
| 2010/0186104 A1 | 7/2010 | Riazuddin et al. | |

(Continued)

FOREIGN PATENT DOCUMENTS

AU    2337892         7/1992
AU    35161 A5        9/2000

(Continued)

OTHER PUBLICATIONS

Amitai et al., "Modulation of intein activity by its neighboring extein substrates," Proc. Nat. Acad. Sci. USA, Jul. 7, 2009, pp. 11005-11010, vol. 106, No. 27.

Cabantous et al., "Protein tagging and detection with engineered self-assembling fragments of green fluorescent protein," Nature Biotechnology, 2005, pp. 102-107, vol. 23.

Castresana et al., "Both positive and negative regulatory elements mediate expression of a photoregulated CAB gene from *Nicotiana plumbaginifolia*," J. European Molecular Biology Organization, 1988, pp. 1929-193, vol. 7.

(Continued)

*Primary Examiner* — Karen Cochrane Carlson
(74) *Attorney, Agent, or Firm* — Knobbe, Martens, Olson & Bear, LLP

(57) ABSTRACT

Embodiments herein include methods and constructs that can be used to co-express two or more polypeptides of interest from a single polynucleotide encoding a precursor polypeptide. Within this precursor polypeptide can reside at least one autonomous processing unit, which can mediate release of flanking polypeptides of interest in cis. The processing unit can include an N-terminal autocatalytic cleavage domain and a C-terminal cleavage domain. Some embodiments include constructs and methods for co-expressing polypeptides without N- or C-terminal overhangs, in any cellular or extracellular location, and/or in stoichiometric ratios.

35 Claims, 38 Drawing Sheets

(56) References Cited

U.S. PATENT DOCUMENTS

| | | |
|---|---|---|
| 2010/0209974 A1 | 8/2010 | You et al. |
| 2010/0251418 A1 | 9/2010 | Snell |
| 2011/0034368 A1 | 2/2011 | Carson et al. |
| 2011/0150861 A1 | 6/2011 | Carson et al. |

FOREIGN PATENT DOCUMENTS

| | | |
|---|---|---|
| AU | 54991 A5 | 1/2001 |
| AU | 3683901 (A) | 8/2001 |
| AU | 2003238719 A1 | 12/2003 |
| AU | 770120 B2 | 2/2004 |
| CA | 2176209 A1 | 6/1995 |
| CA | 2375831 A1 | 12/2000 |
| CA | 2433842 A1 | 8/2002 |
| CA | 2489475 A1 | 12/2003 |
| CA | 2722998 A1 | 12/2003 |
| CA | 2615983 A1 | 2/2007 |
| CA | 2700380 A1 | 4/2009 |
| CN | 101094921 A | 12/2007 |
| CN | 101595228 A | 12/2009 |
| CN | 101842488 A | 9/2010 |
| EP | 1 011 734 B1 | 6/2000 |
| EP | 1 017 834 B1 | 7/2000 |
| EP | 0 736 099 B1 | 10/2001 |
| EP | 1 159 435 A1 | 12/2001 |
| EP | 0 598 029 B1 | 2/2002 |
| EP | 0 749 485 B1 | 2/2002 |
| EP | 1 196 614 A1 | 4/2002 |
| EP | 1 308 517 A1 | 5/2003 |
| EP | 1 356 063 B1 | 10/2003 |
| EP | 1 513 937 A1 | 3/2005 |
| EP | 1 563 077 B1 | 8/2005 |
| EP | 1 700 908 A2 | 9/2006 |
| EP | 1723246 B1 | 11/2006 |
| EP | 1 783 228 A1 | 5/2007 |
| EP | 1 945 773 B1 | 3/2009 |
| EP | 2 048 232 A1 | 4/2009 |
| EP | 2 159 287 A2 | 3/2010 |
| EP | 2 159 288 A2 | 3/2010 |
| JP | 2008-61650 A | 3/2008 |
| JP | 2010-004886 A | 1/2010 |
| JP | 2010-011859 A | 1/2010 |
| KR | 10-2008-0031024 A | 4/2008 |
| MX | 2008000985 A | 4/2008 |
| MX | 2010003631 A | 4/2010 |
| NZ | 537073 A | 8/2006 |
| SG | 164383 A1 | 9/2010 |
| WO | WO 93/03143 A1 | 2/1993 |
| WO | WO 95/17514 | 6/1995 |
| WO | WO 95/21249 A1 | 8/1995 |
| WO | WO 95/24486 A1 | 9/1995 |
| WO | WO 98/06835 A2 | 2/1998 |
| WO | WO 98/54342 A1 | 12/1998 |
| WO | WO 99/03505 A1 | 1/1999 |
| WO | WO 99/35255 A2 | 7/1999 |
| WO | WO 99/35495 A2 | 7/1999 |
| WO | WO 00/11175 A1 | 3/2000 |
| WO | WO 00/52183 A1 | 9/2000 |
| WO | WO 00/78985 A1 | 12/2000 |
| WO | WO 01/09302 A2 | 2/2001 |
| WO | WO 01/59091 A3 | 12/2001 |
| WO | WO 02/16583 A2 | 2/2002 |
| WO | WO 02/16655 A2 | 2/2002 |
| WO | WO 02/061100 A1 | 8/2002 |
| WO | WO 03/102197 A1 | 12/2003 |
| WO | WO 03/106684 A3 | 4/2004 |
| WO | WO 2004/043997 A2 | 5/2004 |
| WO | WO 2004/046359 A2 | 6/2004 |
| WO | WO 2004/046360 A2 | 6/2004 |
| WO | WO 2004/094598 A2 | 11/2004 |
| WO | WO 2004/094642 A2 | 11/2004 |
| WO | WO 2005/024031 A1 | 3/2005 |
| WO | WO 2005/047512 A2 | 5/2005 |
| WO | WO 2005/085456 A1 | 9/2005 |
| WO | WO 2006/052363 A2 | 5/2006 |
| WO | WO 2007/054250 A1 | 5/2007 |
| WO | WO 2005/112597 A3 | 8/2007 |
| WO | WO 2007/137329 A2 | 12/2007 |
| WO | WO 2008/094512 A2 | 8/2008 |
| WO | WO 2009/033653 A1 | 3/2009 |
| WO | WO 2009/046006 A1 | 4/2009 |
| WO | WO 2007/014162 A3 | 5/2009 |
| WO | WO 2009/129596 A1 | 10/2009 |
| WO | WO 2010/066851 A1 | 6/2010 |
| WO | WO 2011/053699 A1 | 5/2011 |

OTHER PUBLICATIONS

Christopher et al., "A novel light-regulated promoter is conserved in cereal and dicot chloroplasts," The Plant Cell, Jul. 1992, pp. 785-798, vol. 4, American Society of Plant Physiologists.

Creighton et al., "Proteins: Structures and Molecular Principles," 1983, W.H. Freeman & Co., N.Y.

Dassa et al., "New type of polyubiquitin-like genes with intein-like autoprocessing domains," TRENDS in Genetics, Nov. 2004, pp. 538-542, vol. 20, No. 11.

De Felipe et al., "Inhibition of 2A-mediated 'cleavage' of certain artificial polyproteins bering N-terminal signal sequences," Biotechnol. J., Feb. 2010, pp. 213-223, vol. 5, Issue 2.

De Felipe et al., "E unum pluribus: multiple proteins from a self-processing polyprotein," Trends in Biotechnology, Feb. 2006, pp. 68-75, vol. 24, Issue 2, Cell Press.

El Amrani et al., "Coordinate expression and independent subcellular targeting of multiple proteins from a single transgene," Plant Physiology, May 2004, pp. 16-24, vol. 135, No. 1, American Society of Plant Biologists.

Fisher et al., "Rapid, efficient production of homozygous transgenic tobacco plants with *Agrobacterium tumefaciens*: A seed-to-seed protocol," Plant Molecular Biology Reporter, Sep. 1995, pp. 278-289, vol. 13, Issue 3.

Francois et al., "Processing in *Arabidopsis thaliana* of a heterologous polyprotein resulting in differential targeting of the individual plant defensins," Plant Science, Jan. 2004, pp. 113-121, vol. 166, Issue 1.

Fromm et al., "An octopine synthase enhancer element directs tissue-specific expression and binds ASF-1, a factor from tobacco nuclear extracts," The Plant Cell, Oct. 1989, pp. 977-984, vol. 1, American Society of Plant Physiologists.

Hiraga et al., "Minimization and stabilization of the *Mycobacterium tuberculosis recA* intein," Journal of Molecular Biology, Dec. 9, 2005, pp. 916-926, vol. 354, Issue 4.

Houghten et al., "General method for the rapid solid-phase synthesis of large numbers of peptides: Specificity of antigen-antibody interaction at the level of individual amino acids," Proc. Natl. Acad. Sci. USA, 1985, pp. 5131-5135, vol. 82.

Kunes et al., "Expression of antibodies using single-open reading frame vector design and polyprotein processing from mammalian cells," Biotechnol. Prog., 2009, pp. 735-744, vol. 25, No. 3, American Institute of Chemical Engineers.

Li et al., "Dipeptide seryl-histidine and related oligopeptides cleave DNA, protein, and a carboxyl ester," Bioorganic & Medicinal Chemistry, Dec. 2000, pp. 2675-2680, vol. 8, Issue 12.

Lumbreras et al., "The use of an alternative promoter in the *Arabidopsis thaliana HMG1* gene generates an mRNA that encodes a novel 3-hydroxy-3-methylglutaryl coenzyme A reductase isoform with an extended N-terminal region," The Plant Journal, 1995, pp. 541-549, vol. 8, No. 4. L.

Mann et al., "Novel lipid modifications of secreted protein signals," Biochemistry, Jul. 2004, pp. 891-923, vol. 73.

Martin et al., "Characterization of a naturally occurring trans-splicing intein from *Synechocystis* sp. PCC6803," Biochemistry, Feb. 6, 2001, pp. 1393-1402, vol. 40, No. 5.

Mathys et al., "Characterization of a self-splicing mini-intein and its conversion into autocatalytic N-and C-terminal cleavage elements: facile production of protein building blocks for protein ligation," Gene, Apr. 29, 1999, pp. 1-13, vol. 231, Issues 1-2.

Merrifield et al., "Solid Phase Peptide Synthesis. I. The Synthesis of a Tetrapeptide," J. Am. Chem. Soc., 1964, vol. 85, pp. 2149-2154.

(56) References Cited

OTHER PUBLICATIONS

Perisic and Lam, "A tobacco DNA binding protein that interacts with a light-responsive box II element," The Plant Cell, Jul. 1992, pp. 831-838, vol. 4.

Requesens et al., "A method of transient expression in maize endosperm," In Vitro Cell.Dev.Biol.—Plant, 2010, pp. 485-490, vol. 46.

Samlova et al., "Ratiometric fluorescence-imaging assays of plant membrane traffic using polyproteins," Traffic, Dec. 2006, pp. 1701-1723, vol. 7, No. 12.

Scott et al., "Production of cyclic peptides and proteins in vivo," PNAS, Nov. 23, 1999, pp. 13638-13643, vol. 96, No. 24.

Shirsat et al., "Sequences responsible for the tissue specific promoter activity of a pea legumin gene in tobacco," Molecular and General Genetics MGG, Jan. 1989, pp. 326-331, vol. 215, Issue 2.

Stewart and Young, "Solid phase peptide synthesis," 1969 W. H. Freeman, San Francisco.

Walker et al., "A ubiquitin-based vector for the co-ordinated synthesis of multiple proteins in plants," Plant Biotechnol J., May 2007, pp. 413-421, vol. 5, No. 3.

Xu et al., "The mechanism of protein splicing and its modulation by mutation," The EMBO Journal, 1996, pp. 5146-5153, vol. 15, No. 19.

Yang et al., "Functional analysis of the split *Synechocystis* DnaE intein in plant tissues by biolistic particle bombardment," Transgenic Research, Oct. 1, 2006, pp. 583-593, vol. 15, Issue 5.

International Preliminary Report on Patentability dated May 27, 2014 in Application No. PCT/US2012/066424.

International Search Report and Written Opinion dated Feb. 28, 2013 in Application No. PCT/US2012/066424.

Volkmann et al., "Intein lacking conserved C-terminal motif G retains controllable N-cleavage activity", The FEBS Journal, vol. 278, No. 18, Aug. 31, 2011.

FIGURE 1D
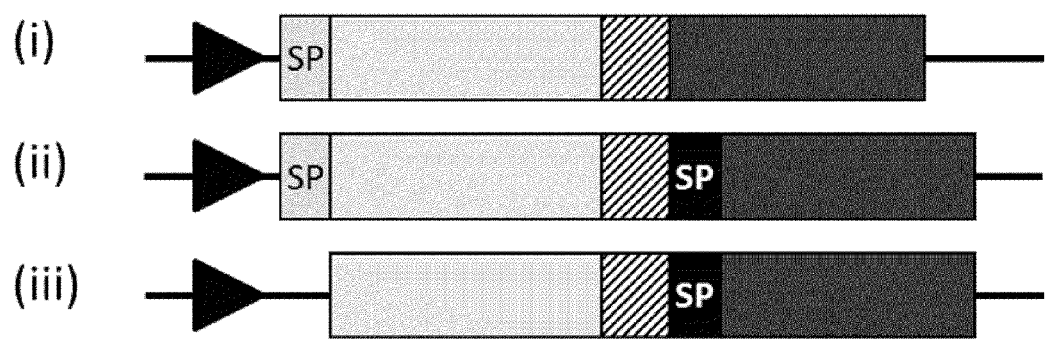
 = processing unit
SP = signal peptide

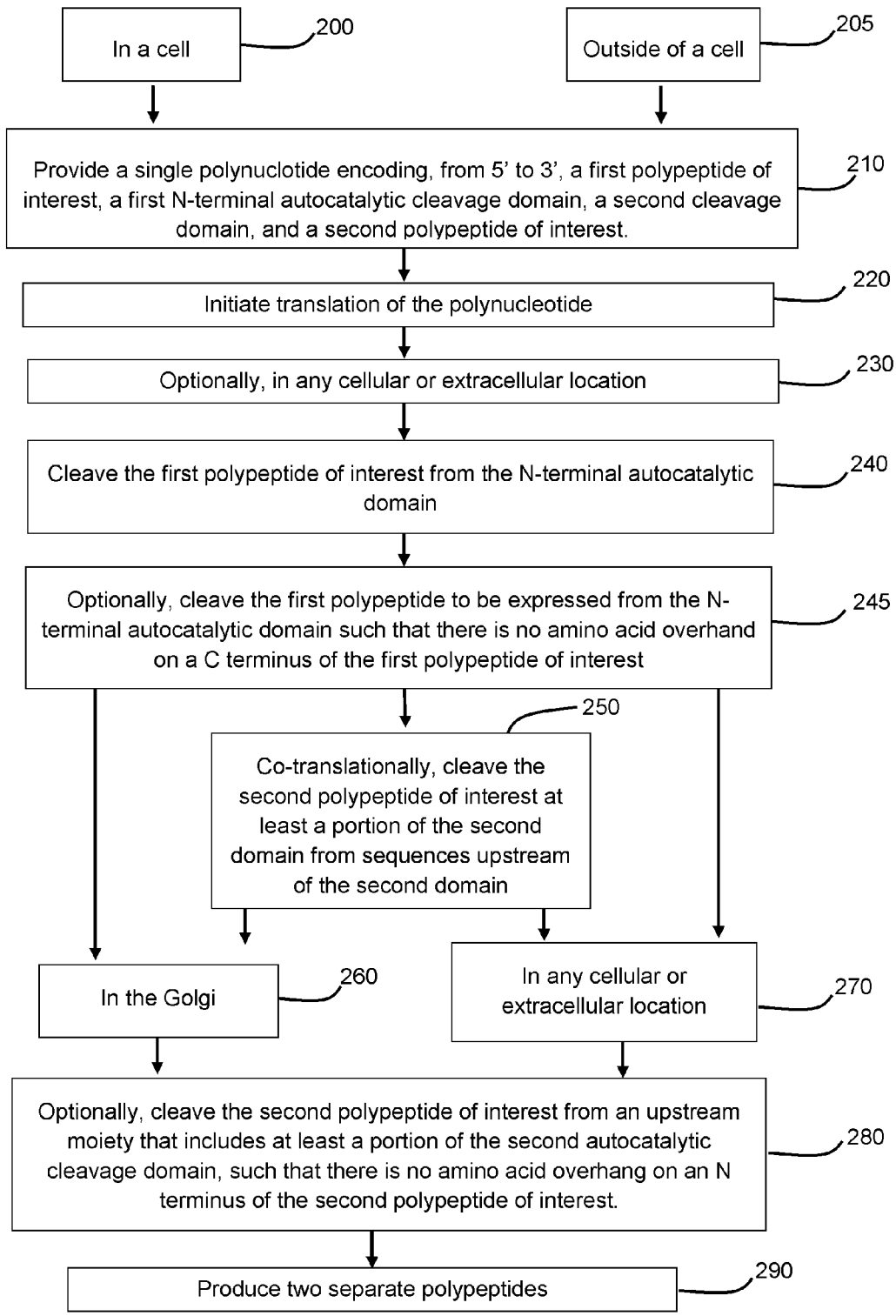

Figure 6A GFP-intein::F2A-mCherry sequence

KpnI GFP172
1 (SEQ ID NO: 8) GGTACCGTCGACCAAGGAGATATAACAATGAGTAAAGGAGAAGAACTTTTCACTGGAGTTGTCCCAATTCTTGTTGAATTAGATGGTGAT
1 (SEQ ID NO: 9) M S K G E E L F T G V V P I L V E L D G D

91 GTTAATGGGCACAAATTTTCTGTCAGTGGAGAGGGTGAAGGTGATGCAACATACGGAAAACTTACCCTTAAATTTATTTGCACTACTGGA
31 V N G H K F S V S G E G E G D A T Y G K L T L K F I C T T G

181 AAACTACCTGTTCCTTGGCCAACACTTGTCACTACTTTCACTTATGGTGTTCAATGCTTTTCAAGATACCCAGATCATATGAAGCGGCAC
61 K L P V P W P T L V T T F T Y G V Q C F S R Y P D H M K R H

271 GACTTCTTCAAGAGCGCCATGCCTGAGGGATACGTGCAGGAGAGGACCATCTTCTTCAAGGACGACGGGAACTACAAGACACGTGCTGAA
91 D F F K S A M P E G Y V Q E R T I F F K D D G N Y K T R A E

361 GTCAAGTTTGAGGGAGACACCCTCGTCAACAGGATCGAGCTTAAGGGAATCGATTTCAAGGAGGACGGAAACATCCTCGGCCACAAGTTG
121 V K F E G D T L V N R I E L K G I D F K E D G N I L G H K L

451 GAATACAACTACAACTCCCACAACGTATACATCATGGCCGACAAGCAAAAGAACGGCATCAAAGCCAACTTCAAGACCCGCCACAACATC
151 E Y N Y N S H N V Y I M A D K Q K N G I K A N F K T R H N I

541 GAACACCATCACCATCACCATCACGGCGGCGTGCAACTCGCTGATCATTATCAACAAAATACTCCAATTGGCGATGGCCCTGTCCTTTTA
181 E H H H H H H H G G V Q L A D H Y Q Q N T P I G D G P V L L

BstBI
631 CCAGACAACCATTACCTGTCCACACAATCTGCCCTTTTCGAAAGATCCCAACGAAAAGAGAGACCACATGGTCCTTCTTGAGTTTGTAACA
211 P D N H Y L S T Q S A L S K D P N E K R D H M V L L E F V T

DnaE intein w/o N-Extein
721 GCTGCTGGGATTACACATGGCATGGATGAACTATACAAATGTTTGTCCTTCGGAACTGAGATACTTACAGTTGAATATGGACCACTTCCT
241 A A G I T H G M D E L Y K C L S F G T E I L T V E Y G P L P 811 ATTGGAAAGATTGTGAGTGAAGAGATCAACTGCAGTGTTTATTCCGTGGATCCAGAGGGTAGAGTTTACACTCAAGCAATTGCTCAGTGG
271 I G K I V S E E I N C S V Y S V D P E G R V Y T Q A I A Q W 901 CATGATAGGGGAGAACAGGAGGTTCTTGAATATGAGTTGGAAGATGGCTCTGTGATAAGAGCTACATCAGATCACAGGTTTCTTACTACA
301 H D R G E Q E V L E Y E L E D G S V I R A T S D H R F L T T 991 GATTACCAACTTTTGGCAATCGAAGAGATTTTCGCTAGACAGCTCGATCTTCTCACTTTGGAAAATATTAAGCAAACAGAAGAGGCACTT
331 D Y Q L L A I E E I F A R Q L D L L T L E N I K Q T E E A L 1081 GATAACCATAGGCTTCCATTTCCTCTTTTGGATGCTGGAACTATTAAGATGGTTAAAGTGATAGGAAGAAGGTCATTGGGTGTTCAAAGA
361 D N H R L P F P L L D A G T I K M V K V I G R R S L G V Q R C-Extein FMDV 2A XbaI
1171 ATATTTGATATCGGACTTCCTCAGGATCACAATTTTCTTACTCGCAAACGGTGCTATTGCTGCAGCTTGTTCTTGTGGCTCTGGTTCTAGA
391 I F D I G L P Q D H N F L L A N G A I A A A C S C G S G S R

1261 GTTACTGAGCTTTTGTATAGGATGAAGAGGGCAGAAACATACTGCCCAAGACCTTTACTCGCAATCCATCCAACAGAGGCTAGGCACAAG
421 V T E L L Y R M K R A E T Y C P R P L L A I H P T E A R H K

HindIII ApaI mCherry
1351 CAAAAAATTGTTGCTCCTGTGAAACAGCTTTTGAACTTTGATCTTCTCAAGCTTGCGGGAGACGTCGAGTCCAACCCTGGGCCCGTGAGC
451 Q K I V A P V K Q L L N F D L L K L A G D V E S N P G P V S 1441 AAGGGCGAGGAGGATAACATGGCCATCATCAAGGAGTTCATGCGCTTCAAGGTGCACATGGAGGGCTCCGTGAACGGCCACGAGTTCGAG
481 K G E E D N M A I I K E F M R F K V H M E G S V N G H E F E 1531 ATCGAGGGCGAGGGCGAGGGCCGCCCCTACGAGGGCACCCAGACCGCCAAGCTGAAGGTGACCAAGGGTGGCCCCCTGCCCTTCGCCTGG
511 I E G E G E G R P Y E G T Q T A K L K V T K G G P L P F A W 1621 GACATCCTGTCCCCTCAGTTCATGTACGGCTCCAAGGCCTACGTGAAGCACCCCGCCGACATCCCCGACTACTTGAAGCTGTCCTTCCCC
541 D I L S P Q F M Y G S K A Y V K H P A D I P D Y L K L S F P 1711 GAGGGCTTCAAGTGGGAGCGCGTGATGAACTTCGAGGACGGCGGCGTGGTGACCGTGACCCAGGACTCCTCCCTGCAGGACGGCGAGTTC
571 E G F K W E R V M N F E D G G V V T V T Q D S S L Q D G E F 1801 ATCTACAAGGTGAAGCTGCGCGGCACCAACTTCCCCTCCGACGGCCCCGTAATGCAGAAGAAGACCATGGGCTGGGAGGCCTCCTCCGAG
601 I Y K V K L R G T N F P S D G P V M Q K K T M G W E A S S E 1891 CGGATGTACCCCGAGGACGGCGCCCTGAAGGGCGAGATCAAGCAGAGGCTGAAGCTGAAGGACGGCGGCCACTACGACGCTGAGGTCAAG
631 R M Y P E D G A L K G E I K Q R L K L K D G G H Y D A E V K 1981 ACCACCTACAAGGCCAAGAAGCCCGTGCAGCTGCCCGGCGCCTACAACGTCAACATCAAGTTGGACATCACCTCCCACAACGAGGACTAC
661 T T Y K A K K P V Q L P G A Y N V N I K L D I T S H N E D Y 2071 ACCATCGTGGAACAGTACGAACGCGCCGAGGGCCGCCACTCCACCGGCGGCATGGACGAGCTGTACAAGGGTTCTGGATGGTCACATCCT
691 T I V E Q Y E R A E G R H S T G G M D E L Y K G S G W S H P Streptag
2161 CAGTTTGAAAAATGAGAGCTC
721 Q F E K *

Figure 6B: GFP-intein::F2A-mCherry nucleotide sequence

SEQ ID NO: 8

```
GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGAGGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGGAAACATCCTGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAATGTTTGTCCTTCGGAACTGAGATACTTACAGTTGAATATGGACCACTTCCT
ATTGGAAAGATTGTGAGTGAAGAGATCAACTGCAGTGTTTATTCCGTGGATCCAGAGGGTAGAGTTTACACTCAAGCAATT
GCTCAGTGGCATGATAGGGGAGAACAGGAGGTTCTTGAATATGAGTTGGAAGATGGTTCTGTGATAAGAGCTACATCAGAT
CACAGGTTTCTTACTACAGATTACCAACTTTTGGCAATCGAAGAGATTTTCGCTAGACAGCTCGATCTTCTCACTTTGGAA
AATATTAAGCAAACAGAAGAGGCACTTGATAACCATAGGCTTCCATTTCCTCTTTTGGATGCTGGAACTATTAAGATGGTT
AAAGTGATAGGAAGAAGGTCATTGGGTGTTCAAAGAATATTTGATATCGGACTTCCTCAGGATCACAATTTCTTACTCGCA
AACGGTGCTATTGCTGCAGCTTGTTCTTGTGGTTCTGGTTCTAGAGTTACTGAGCTTTTGTATAGGATGAAGAGGGCAGAA
ACATACTGCCCAAGACCTTTACTCGCAATCCATCCAACAGAGGCTAGGCACAAGCAAAAAATTGTTGCTCCTGTGAAACAG
CTTTTGAACTTTGATCTTCTCAAGCTTGCGGGAGACGTCGAGTCCAACCCTGGGCCCGTGAGCAAGGGCGAGGAGGATAAC
ATGGCCATCATCAAGGAGTTCATGCGCTTCAAGGTGCACATGGAGGGCTCCGTGAACGGCCACGAGTTCGAGATCGAGGGC
GAGGGCGAGGGCCGCCCCTACGAGGGCACCCAGACCGCCAAGCTGAAGGTGACCAAGGGTGGCCCCCTGCCCTTCGCCTGG
GACATCCTGTCCCCTCAGTTCATGTACGGCTCCAAGGCCTACGTGAAGCACCCCGCCGACATCCCCGACTACTTGAAGCTG
TCCTTCCCCGAGGGCTTCAAGTGGGAGCGCGTGATGAACTTCGAGGACGGCGGCGTGGTGACCGTGACCCAGGACTCCTCC
CTGCAGGACGGCGAGTTCATCTACAAGGTGAAGCTGCGCGGCACCAACTTCCCCTCCGACGGCCCCGTAATGCAGAAGAAG
ACCATGGGCTGGGAGGCCTCCTCCGAGCGGATGTACCCCGAGGACGGCGCCCTGAAGGGCGAGATCAAGCAGAGGCTGAAG
CTGAAGGACGGCGGCCACTACGACGCTGAGGTCAAGACCACCTACAAGGCCAAGAAGCCCGTGCAGCTGCCCGGCGCCTAC
AACGTCAACATCAAGTTGGACATCACCTCCCACAACGAGGACTACACCATCGTGGAACAGTACGAACGCGCCGAGGGCCGC
CACTCCACCGGCGGCATGGACGAGCTGTACAAGGGTTCTGGATGGTCACATCCTCAGTTTGAAAAATGAGAGCTC
```

Figure 7A: SP1-GFP-intein::F2A-SP2-mCherry sequence

Figure 7B: SP1-GFP-intein::F2A-SP2-mCherry sequence - nucleotide sequence

SEQ ID NO: 6

GGTACCGTCGACCAAGGAGATATAACAATGAAGACTAATCTTTTTCTCTTTCTCATCTTTTCACTTCTCCTATCATTATCC
TCGGCCGAATTCAGTAAAGGAGAAGAACTTTTCACTGGAGTTGTCCCAATTCTTGTTGAATTAGATGGTGATGTTAATGGG
CACAAATTTTCTGTCAGTGGAGAGGGTGAAGGTGATGCAACATACGGAAAACTTACCCTTAAATTTATTTGCACTACTGGA
AAACTACCTGTTCCTTGGCCAACACTTGTCACTACTTTCACTTATGGTGTTCAATGCTTTTCAAGATACCCAGATCATATG
AAGCGGCACGACTTCTTCAAGAGCGCCATGCCTGAGGGATACGTGCAGGAGAGGACCATCTTCTTCAAGGACGACGGGAAC
TACAAGACACGTGCTGAAGTCAAGTTTGAGGGAGACACCCTCGTCAACAGGATCGAGCTTAAGGGAATCGATTTCAAGGAG
GACGGAAACATCCTCGGCCACAAGTTGGAATACAACTACAACTCCCACAACGTATACATCATGGCCGACAAGCAAAAGAAC
GGCATCAAAGCCAACTTCAAGACCCGCCACAACATCGAACACCATCACCATCACCATGACGGCGGCGTGCAACTCGCTGAT
CATTATCAACAAAATACTCCAATTGGCGATGGCCCTGTCCTTTTACCAGACAACCATTACCTGTCCACACAATCTGCCCTT
TCGAAAGATCCCAACGAAAAGAGAGACCACATGGTCCTTCTTGAGTTTGTAACAGCTGCTGGGATTACACATGGCATGGAT
GAACTATACAAACTCGAGGGAGGATCTAAGTTTGCAAATGATTGTTTGTCCTTCGGAACTGAGATACTTACAGTTGAATAT
GGACCACTTCCTATTGGAAAGATTGTGAGTGAAGAGATCAACTGCAGTGTTTATTCCGTGGATCCAGAGGGTAGAGTTTAC
ACTCAAGCAATTGCTCAGTGGCATGATAGGGGAGAACAGGAGGTTCTTGAATATGAGTTGGAAGATGGTTCTGTGATAAGA
GCTACATCAGATCACAGGTTTCTTACTACAGATTACCAACTTTTGGCAATCGAAGAGATTTTCGCTAGACAGCTCGATCTT
CTCACTTTGGAAAATATTAAGCAAACAGAAGAGGCACTTGATAACCATAGGCTTCCATTTCCTCTTTTGGATGCTGGAACT
ATTAAGATGGTTAAAGTGATAGGAAGAAGGTCATTGGGTGTTCAAAGAATATTTGATATCGGACTTCCTCAGGATCACAAT
TTCTTACTCGCAAACGGTGCTATTGCTGCAGCTTGTTTCAATGGTTCTGGTTCTAGAGTTACTGAGCTTTTGTATAGGATG
AAGAGGGCAGAAACATACTGCCCAAGACCTTTACTCGCAATCCATCCAACAGAGGCTAGGCACAAGCAAAAATTGTTGCT
CCTGTGAAACAGCTTTTGAACTTTGATCTTCTCAAGCTTGCGGGAGACGTCGAGTCCAACCCTGGGCCCCAGGTGCTGAAC
ACCATGGTGAACAAACACTTCTTGTCCCTTTCGGTCCTCATCGTCCTCCTTGGCCTCTCCTCCAACTTGACAGCCGGCATG
CTGAGCAAGGGCGAGGAGGATAACATGGCCATCATCAAGGAGTTCATGCGCTTCAAGGTGCACATGGAGGGCTCCGTGAAC
GGCCACGAGTTCGAGATCGAGGGCGAGGGCGAGGGCCGCCCCTACGAGGGCACCCAGACCGCCAAGCTGAAGGTGACCAAG
GGTGGCCCCCTGCCCTTCGCCTGGGACATCCTGTCCCCTCAGTTCATGTACGGCTCCAAGGCCTACGTGAAGCACCCCGCC
GACATCCCCGACTACTTGAAGCTGTCCTTCCCCGAGGGCTTCAAGTGGGAGCGCGTGATGAACTTCGAGGACGGCGGCGTG
GTGACCGTGACCCAGGACTCCTCCCTGCAGGACGGCGAGTTCATCTACAAGGTGAAGCTGCGCGGCACCAACTTCCCCTCC
GACGGCCCCGTAATGCAGAAGAAGACCATGGGCTGGGAGGCCTCCTCCGAGCGGATGTACCCCGAGGACGGCGCCCTGAAG
GGCGAGATCAAGCAGAGGCTGAAGCTGAAGGACGGCGGCCACTACGACGCTGAGGTCAAGACCACCTACAAGGCCAAGAAG
CCCGTGCAGCTGCCCGGCGCCTACAACGTCAACATCAAGTTGGACATCACCTCCCACAACGAGGACTACACCATCGTGGAA
CAGTACGAACGCCGAGGGCCGCCACTCCACCGGCGGCATGGACGAGCTGTACAAGGGTTCTGGATGGTCACATCCTCAG
TTTGAAAAATGAGAGCTC

Figure 8A: SP-GFP-intein::F2A-mCherry sequence

Figure 8B: SP-GFP-intein::F2A-mCherry nucleotide sequence

SEQ ID NO: 18

GTCGACCAAGGAGATATAACAATGAAGACTAATCTTTTTCTCTTTCTCATCTTTTCACTTCTCCTATCATTATCCTCGGCC
GAATTCAGTAAAGGAGAAGAACTTTTCACTGGAGTTGTCCCAATTCTTGTTGAATTAGATGGTGATGTTAATGGGCACAAA
TTTTCTGTCAGTGGAGAGGGTGAAGGTGATGCAACATACGGAAAACTTACCCTTAAATTTATTTGCACTACTGGAAAACTA
CCTGTTCCTTGGCCAACACTTGTCACTACTTTCACTTATGGTGTTCAATGCTTTTCAAGATACCCAGATCATATGAAGCGG
CACGACTTCTTCAAGAGCGCCATGCCTGAGGGATACGTGCAGGAGAGGACCATCTTCTTCAAGGACGACGGGAACTACAAG
ACACGTGCTGAAGTCAAGTTTGAGGGAGACACCCTCGTCAACAGGATCGAGCTTAAGGGAATCGATTTCAAGGAGGACGGA
AACATCCTCGGCCACAAGTTGGAATACAACTACAACTCCCACAACGTATACATCATGGCCGACAAGCAAAAGAACGGCATC
AAAGCCAACTTCAAGACCCGCCACAACATCGAACACCATCACCATCACCATGACGGCGGCGTGCAACTCGCTGATCATTAT
CAACAAAATACTCCAATTGGCGATGGCCCTCTCCTTTTACCAGACAACCATTACCTGTCCACACAATCTGCCCTTTCGAAA
GATCCCAACGAAAAGAGAGACCACATGGTCCTTCTTGAGTTTGTAACAGCTGCTGGGATTACACATGGCATGGATGAACTA
TACAAACTCGAGGGAGGATCTAAGTTTGCAAATGATTGTTTGTCCTTCGGAACTGAGATACTTACAGTTGAATATGGACCA
CTTCCTATTGGAAAGATTGTGAGTGAAGAGATCAACTGCAGTGTTTATTCCGTGGATCCAGAGGGTAGAGTTTACACTCAA
GCAATTGCTCAGTGGCATGATAGGGGAGAACAGGAGGTTCTTGAATATGAGTTGGAAGATGGTTCTGTGATAAGAGCTACA
TCAGATCACAGGTTTCTTACTACAGATTACCAACTTTTGGCAATCGAAGAGATTTTCGCTAGACAGCTCGATCTTCTCACT
TTGGAAAATATTAAGCAAACAGAAGAGGCACTTGATAACCATAGGCTTCCATTTCCTCTTTTGGATGCTGGAACTATTAAG
ATGGTTAAAGTGATAGGAAGAAGGTCATTGGGTGTTCAAAGAATATTTGATATCGGACTTCCTCAGGATCACAATTTCTTA
CTCGCAAACGGTGCTATTGCTGCAGCTTGTTTCAATGGTTCTGGTTCTAGAGTTACTGAGCTTTTGTATAGGATGAAGAGG
GCAGAAACATACTGCCCAAGACCTTTACTCGCAATCCATCCAACAGAGGCTAGGCACAAGCAAAAAATTGTTGCTCCTGTG
AAACAGCTTTTGAACTTTGATCTTCTCAAGCTTGCGGGAGACGTCGAGTCCAACCCTGGGCCCGTGAGCAAGGGCGAGGAG
GATAACATGGCCATCATCAAGGAGTTCATGCGCTTCAAGGTGCACATGGAGGGCTCCGTGAACGGCCACGAGTTCGAGATC
GAGGGCGAGGGCGAGGGCCGCCCCTACGAGGGCACCCAGACCGCCAAGCTGAAGGTGACCAAGGGTGGCCCCCTGCCCTTC
GCCTGGGACATCCTGTCCCCTCAGTTCATGTACGGCTCCAAGGCCTACGTGAAGCACCCCGCCGACATCCCCGACTACTTG
AAGCTGTCCTTCCCCGAGGGCTTCAAGTGGGAGCGCGTGATGAACTTCGAGGACGGCGGCGTGGTGACCGTGACCAAGACC
ATGGGCTGGGAGGCCTCCTCCGAGCGGATGTACCCCGAGGACGGCGCCCTGAAGGGCGAGATCAAGCAGAGGCTGAAGCTG
AAGCAGGACTCCTCCCTGCAGGACGGCGAGTTCATCTACAAGGTGAAGCTGCGCGGCACCAACTTCCCCTCCGACGGCCCC
GTAATGCAGAAGGACGGCGGCCACTACGACGCTGAGGTCAAGACCACCTACAAGGCCAAGAAGCCCGTGCAGCTGCCCGGC
GCCTACAACGTCAACATCAAGTTGGACATCACCTCCCACAACGAGGACTACACCATCGTGGAACAGTACGAACGCGCCGAG
GGCCGCCACTCCACCGGCGGCATGGACGAGCTGTACAAGGGTTCTGGATGGTCACATCCTCAGTTTGAAAAATGAGAGCTC

Figure 9A: GFP-intein::Sea urchin 2A-mCherry sequence

Figure 9B: GFP-intein::Sea urchin 2A-mCherry sequence

SEQ ID NO: 12

```
GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGACGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGAAACATCCTCGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAATGTTTGTCCTTCGGAACTGAGATACTTACAGTTGAATATGGACCACTTCCT
ATTGGAAAGATTGTGAGTGAAGAGATCAACTGCAGTGTTTATTCCGTGGATCCAGAGGGTAGAGTTTACACTCAAGCAATT
GCTCAGTGGCATGATAGGGGAGAACAGGAGGTTCTTGAATATGAGTTGGAAGATGGTTCTGTGATAAGAGCTACATCAGAT
CACAGGTTTCTTACTACAGATTACCAACTTTTGGCAATCGAAGAGATTTTCGCTAGACAGCTCGATCTTCTCACTTTGGAA
AATATTAAGCAAACAGAAGAGGCACTTGATAACCATAGGCTTCCATTTCCTCTTTTGGATGCTGGAACTATTAAGATGGTT
AAAGTGATAGGAAGAAGGTCATTGGGTGTTCAAAGAATATTTGATATCGGACTTCCTCAGGATCACAATTTCTTACTCGCA
AACGGTGCTATTGCTGCAGCTTGTTCTTGTGGTTCTGGTTCTAGAGATGGATTCTGCATTCTCTATCTGCTCCTGATCCTC
TTGATGAGATCTGGTGACGTTGAAACCAATCCAGGGCCCGTGAGCAAGGGCGAGGAGGATAACATGGCCATCATCAAGGAG
TTCATGCGCTTCAAGGTGCACATGGAGGGCTCCGTGAACGGCCACGAGTTCGAGATCGAGGGCGAGGGCGAGGGCCGCCCC
TACGAGGGCACCCAGACCGCCAAGCTGAAGGTGACCAAGGGTGGCCCCCTGCCCTTCGCCTGGGACATCCTGTCCCCTCAG
TTCATGTACGGCTCCAAGGCCTACGTGAAGCACCCCGCCGACATCCCCGACTACTTGAAGCTGTCCTTCCCCGAGGGCTTC
AAGTGGGAGCGCGTGATGAACTTCGAGGACGGCGGCGTGGTGACCGTGACCCAGGACTCCTCCCTGCAGGACGGCGAGTTC
ATCTACAAGGTGAAGCTGCGCGGCACCAACTTCCCCTCCGACGGCCCCGTAATGCAGAAGAAGACCATGGGCTGGGAGGCC
TCCTCCGAGCGGATGTACCCCGAGGACGGCGCCCTGAAGGGCGAGATCAAGCAGAGGCTGAAGCTGAAGGACGGCGGCCAC
TACGACGCTGAGGTCAAGACCACCTACAAGGCCAAGAAGCCCGTGCAGCTGCCCGGCGCCTACAACGTCAACATCAAGTTG
GACATCACCTCCCACAACGAGGACTACACCATCGTGGAACAGTACGAACGCGCCGAGGGCCGCCACTCCACCGGCGGCATG
GACGAGCTGTACAAGGGTTCTGGATGGTCACATCCTCAGTTTGAAAAATGAGAGCTC
```

Figure 10A: GFP-Intein-Intein-mCherry (Ssp DnaE intein - Ssp DnaB intein) sequence Figure 10B: GFP-Intein-Intein-mCherry (Ssp DnaE intein - Ssp DnaB intein)
- nucleotide sequence >DI-1 (2520 bp)

(SEQ ID NO: 14)

```
GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGAGGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGAAACATCCTCGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAACTCGAGGGAGGATCTAAGTTTGCAAATGATTGTTTGTCCTTCGGAACTGAG
ATACTTACAGTTGAATATGGACCACTTCCTATTGGAAAGATTGTGAGTGAAGAGATCAACTGCAGTGTTTATTCCGTGGAT
CCAGAGGGTAGAGTTTACACTCAAGCAATTGCTCAGTGGCATGATAGGGGAGAACAGGAGGTTCTTGAATATGAGTTGGAA
GATGGTTCTGTGATAAGAGCTACATCAGATCACAGGTTTCTTACTACAGATTACCAACTTTTGGCAATCGAAGAGATTTTC
GCTAGACAGCTCGATCTTCTCACTTTGGAAAATATTAAGCAACAGAAGAGGCACTTGATAACCATAGGCTTCCATTTCCT
CTTTTGGATGCTGGAACTATTAAGATGGTTAAAGTGATAGGAAGAAGGTCATTGGGTGTTCAAAGAATATTTGATATCGGA
CTTCCTCAGGATCACAATTTCTTACTCGCAAACGGTGCTATTGCTGCAGCTTGTTTCAATGGTTCTGGTTCTAGAGAGTCT
GGAGCTATCTCTGGCGATAGTCTGATCAGCCTGGCTAGCACAGGAAAAAGAGTTTCTATTAAAGATTTGTTAGATGAAAAA
GATTTTGAAATATGGGCAATTAATGAACAGACGATGAAGCTAGAATCAGCTAAAGTTAGTCGTGTATTTTGTACTGGCAAA
AAGCTAGTTTATATTCTAAAAACTCGACTAGGTAGAACTATCAAGGCAACAGCAAATCATAGATTTTTAACTATTGATGGT
TGGAAAAGATTAGATGAGCTATCTTTAAAAGAGCATATTGCTCTACCCCGTAAACTAGAAAGCTCCTCTTTACAATTGTCA
CCAGAAATAGAAAAGTTGTCTCAGAGTGATATTTACTGGGACTCCATCGTTTCTATTACGGAGACTGGAGTCGAAGAGGTT
TTTGATTTGACTGTGCCAGGACCACATAACTTTGTCGCGAATGACATCATTGTACACAACAGCCGCGGGCCCGTGAGCAAG
GGCGAGGAGGATAACATGGCCATCATCAAGGAGTTCATGCGCTTCAAGGTGCACATGGAGGGCTCCGTGAACGGCCACGAG
TTCGAGATCGAGGGCGAGGGCGAGGGCCGCCCCTACGAGGGCACCCAGACCGCCAAGCTGAAGGTGACCAAGGGTGGCCCC
CTGCCCTTCGCCTGGGACATCCTGTCCCCTCAGTTCATGTACGGCTCCAAGGCCTACGTGAAGCACCCCGCCGACATCCCC
GACTACTTGAAGCTGTCCTTCCCCGAGGGCTTCAAGTGGGAGCGCGTGATGAACTTCGAGGACGGCGGCGTGGTGACCGTG
ACCCAGGACTCCTCCCTGCAGGACGGCGAGTTCATCTACAAGGTGAAGCTGCGCGGCACCAACTTCCCCTCCGACGGCCCC
GTAATGCAGAAGAAGACCATGGGCTGGGAGGCCTCCTCCGAGCGGATGTACCCCGAGGACGGCGCCCTGAAGGGCGAGATC
AAGCAGAGGCTGAAGCTGAAGGACGGCGGCCACTACGACGCTGAGGTCAAGACCACCTACAAGGCCAAGAAGCCCGTGCAG
CTGCCCGGCGCCTACAACGTCAACATCAAGTTGGACATCACCTCCCACAACGAGGACTACACCATCGTGGAACAGTACGAA
CGCGCCGAGGGCCGCCACTCCACCGGCGGCATGGACGAGCTGTACAAGGGTTCTGGATGGTCACATCCTCAGTTTGAAAAA
TGAGAGCTC
```

Figure 11A: GFP-Intein-Intein-mCherry (Ssp DnaE intein - Ssp DnaB intein) (inactive DnaE) sequence

```
            Kpn I   Sal I    RBS                         GFP-172
(SEQ ID NO:16) GGTACCGTCGACCAAGGAGATATAACAATGAGTAAAGGAGAAGAACTTTTCACTGGAGTTGTCCCAATTCTTGTTGAATTAGATGGTGAT
(SEQ ID NO: 17)                        M  S  K  G  E  E  L  F  T  G  V  V  P  I  L  V  E  L  D  G  D

GTTAATGGGCACAAATTTTCTGTCAGTGGAGAGGGTGAAGGTGATGCAACATACGGAAAACTTACCCTTAAATTTATTTGCACTACTGGA  180
 V  N  G  H  K  F  S  V  S  G  E  G  D  A  T  Y  G  K  L  T  L  K  F  I  C  T  T  G

AAACTACCTGTTCCATGGCCAACACTTGTCACTACTTTCTCTTATGGTGTTCAATGCTTTTCAAGATACCCAGATCATATGAAGCGGCAC  270
 K  L  P  V  P  W  P  T  L  V  T  T  F  S  Y  G  V  Q  C  F  S  R  Y  P  D  H  M  K  R  H

GACTTCTTCAAGAGCGCCATGCCTGAGGGATACGTGCAGGAGAGGACCATCTTCTTCAAGGACGACGGGAACTACAAGACACGTGCTGAA  360
 D  F  F  K  S  A  M  P  E  G  Y  V  Q  E  R  T  I  F  F  K  D  D  G  N  Y  K  T  R  A  E

GTCAAGTTTGAGGGAGACACCCTCGTCAACAGGATCGAGCTTAAGGGAATCGATTTCAAGGAGGACGGAAACATCCTCGGCCACAAGTTG  450
 V  K  F  E  G  D  T  L  V  N  R  I  E  L  K  G  I  D  F  K  E  D  G  N  I  L  G  H  K  L

GAATACAACTACAACTCCCACAACGTATACATCATGGCCGACAAGCAAAAGAACGGCATCAAAGCCAACTTCAAGACCCGCCACAACATC  540
 E  Y  N  Y  N  S  H  N  V  Y  I  M  A  D  K  Q  K  N  G  I  K  A  N  F  K  T  R  H  N  I
                    His₆ Tag
GAACACCATCACCATCACCATGACGGCGGCGTGCAACTCGCTGATCATTATCAACAAAATACTCCAATTGGCGATGGCCCTGTCCTTTTA  630
 E  H  H  H  H  H  H  D  G  G  V  Q  L  A  D  H  Y  Q  Q  N  T  P  I  G  D  G  P  V  L  L

CCAGACAACCATTACCTGTCCACACAATCTGCCCTTTCGAAAGATCCCAACGAAAAGAGAGACCACATGGTCCTTCTTGAGTTTGTAACA  720
 P  D  N  H  Y  L  S  T  Q  S  A  L  S  K  D  P  N  E  K  R  D  H  M  V  L  L  E  F  V  T
                              Xho I                         DnaE intein (159 aa)
GCTGCTGGGATTACACATGGCATGGATGAACTATACAAACTCGAGTATGCATTGTCCTTCGGAACTGAGATACTTACAGTTGAATATGGA  810
 A  A  G  I  T  H  C  M  D  E  L  Y  K  L  E  Y  A  L  S  F  G  T  E  I  L  T  V  E  Y  G CCACTTCCTATTGGAAAGATTGTGAGTGAAGAGATCAACTGCAGTGTTTATTCCGTGGATCCAGAGGGTAGAGTTTACACTCAAGCAATT  900
 P  L  P  I  G  K  I  V  S  E  E  I  N  C  S  V  Y  S  V  D  P  E  G  R  V  Y  T  Q  A  I GCTCAGTGGCATGATAGGGGAGAACAGGAGGTTCTTGAATATGAGTTGGAAGATGGTCTGTGATAAGAGCTACATCAGATCACAGGTTT  990
 A  Q  W  H  D  R  G  E  Q  E  V  L  E  Y  E  L  E  D  G  S  V  I  R  A  T  S  D  H  R  F CTTACTACAGATTACCAACTTTTGGCAATCGAAGAGATTTTCGCTAGACAGCTCGATCTTCTCACTTTGGAAAATATTAAGCAAACAGAA  1080
 L  T  T  D  Y  Q  L  L  A  I  E  E  I  F  A  R  Q  L  D  L  L  T  L  E  N  I  K  Q  T  E GAGGCACTTGATAACCATAGGCTTCCATTTCCTCTTTTGGATGCTGGAACTATTAAGATGGTTAAAGTGATAGGAAGAAGGTCATTGGGT  1170
 E  A  L  D  N  H  R  L  P  F  P  L  L  D  A  G  T  I  K  M  V  K  V  I  G  R  R  S  L  G
                                                                                    Xba I
GTTCAAAGAATATTTGATATCGGACTTCCTCAGGATCACAATTTCTTACTCGCAAACGGTGCTATTGCTGCAGCTGGTGGTTCTAGAGAG  1260
 V  Q  R  I  F  D  I  G  L  P  Q  D  H  N  F  L  L  A  N  G  A  I  A  A  A  G  G  S  R  E
DnaB intein (154 aa)
TCTGGAGCTATCTCTGGCGATAGTCTGATCAGCCTGGCTAGCaCAGGAAAAAGAGTTTCTATTAAAGATTTGTtagatGAAAAAGATTTT  1350
 S  G  A  I  S  G  D  S  L  I  S  L  A  S  T  G  K  R  V  S  I  K  D  L  L  D  E  K  D  F GAAATATGGGCAATTAATGAACAGACGATGAAGCTAGAATCAGCTAAAGTTAGTCGTGTATTTTGTACTGGCAAAAAGCTAGTTTATATT  1440
 E  I  W  A  I  N  E  Q  T  M  K  L  E  S  A  K  V  S  R  V  F  C  T  G  K  K  L  V  Y  I CTAAAAACTCGACTAGGTAGAACTATCAAGGCAACACGAAATCATGATTTTTAACTATTGATGGTTGGAAAAGATTAGATGAGCTATCT  1530
 L  K  T  R  L  G  R  T  I  K  A  T  A  N  H  R  F  L  T  I  D  G  W  K  R  L  D  E  L  S TTAAAAGAGCATATTGCTCTACCCCGTAAACTAGAAAGCTCCTCTCTTtaCAATTGTCaCCAGAAATAGAAAAGTTGTCTCAGAGTGATATT  1620
 L  K  E  H  I  A  L  P  R  K  L  E  S  S  S  L  Q  L  S  P  E  I  E  K  L  S  Q  S  D  I TACTGGGACTCCATCGTTTCTATTACGGAGACTGGAGTCGAAGAGGTTTTTGATTTGACTGTGCCAGGACCACATAACTTTGTCGCGAAT  1710
 Y  W  D  S  I  V  S  I  T  E  T  G  V  E  E  V  F  D  L  T  V  P  G  P  H  N  F  V  A  N
                                      Apa I           mCherry (235 aa)
GACATCATTGTACACAACAGCCGCGGGCCCGTGAGCAAGGGCGAGGAGGATAACATGGCCATCATCAAGGAGTTCATGCGCTTCAAGGTG  1800
 D  I  I  V  H  N  S  R  G  P  V  S  K  G  E  E  D  N  M  A  I  I  K  E  F  M  R  F  K  V CACATGGAGGGCTCCGTGAACGGCCACGAGTTCGAGATCGAGGGCGAGGGCGAGGGCCGCCCCTACGAGGGCACCCAGACCGCCAAGCTG  1890
 H  M  E  G  S  V  N  G  H  E  F  E  I  E  G  E  G  E  G  R  P  Y  E  G  T  Q  T  A  K  L AAGGTGACCAAGGGTGGCCCCCTGCCCTTCGCCTGGGACATCCTGTCCCCTCAGTTCATGTACGGCTCCAAGGCCTACGTGAAGCACCCC  1980
 K  V  T  K  G  G  P  L  P  F  A  W  D  I  L  S  P  Q  F  M  Y  G  S  K  A  Y  V  K  H  P GCCGACATCCCCGACTACTTGAAGCTGTCCTTCCCCGAGGGCTTCAAGTGGGAGCGCGTGATGAACTTCGAGGACGGCGGCGTGGTGACC  2070
 A  D  I  P  D  Y  L  K  L  S  F  P  E  G  F  K  W  E  R  V  M  N  F  E  D  G  G  V  V  T GTGACCCAGGACTCCTCCCTGCAGGACGGCGAGTTCATCTACAAGGTGAAGCTGCGCGGCACCAACTTCCCCTCCGACGGCCCCGTAATG  2160
 V  T  Q  D  S  S  L  Q  D  G  E  F  I  Y  K  V  K  L  R  G  T  N  F  P  S  D  G  P  V  M CAGAAGAAGACCATGGGCTGGGAGGCCTCCTCCGAGCGGATGTACCCCGAGGACGGCGCCCTGAAGGGCGAGATCAAGCAGAGGCTGAAG  2250
 Q  K  K  T  M  G  W  E  A  S  S  E  R  M  Y  P  E  D  G  A  L  K  G  E  I  K  Q  R  L  K CTGAAGGACGGCGGCCACTACGACGCTGAGGTCAAGACCACCTACAAGGCCAAGAAGCCCGTGCAGCTGCCCGGCGCCTACAACGTCAAC  2340
 L  K  D  G  G  H  Y  D  A  E  V  K  T  T  Y  K  A  K  K  P  V  Q  L  P  G  A  Y  N  V  N ATCAAGTTGGACATCACCTCCCACAACGAGGACTACACCATCGTGGAACAGTACGAACGCGCCGAGGGCCGCCACTCCACCGGCGGCATG  2430
 I  K  L  D  I  T  S  H  N  E  D  Y  T  I  V  E  Q  Y  E  R  A  E  G  R  H  S  T  G  G  M
                                          Strep Tag              Sac I
GACGAGCTGTACAAGGGGTTCTGGATGGTCACATCCTCAGTTTGAAAAATGAGAGCTC  2487
 D  E  L  Y  K  G  S  G  W  S  H  P  Q  F  E  K  *
```

Figure 11B: GFP-Intein-Intein-mCherry (Ssp DnaE intein - Ssp DnaB intein) (inactive DnaE) – nucleotide sequence >DI-1C (2487 bp)

SEQ ID NO: 16

```
GGTACCGTCGACCAAGGAGATATAACAATGAGTAAAGGAGAAGAACTTTTCACTGGAGTTGTCCCAATTCTTGTTGAATTAGATGGTGA
TGTTAATGGGCACAAATTTTCTGTCAGTGGAGAGGGTGAAGGTGATGCAACATACGGAAAACTTACCCTTAAATTTATTTGCACTACTG
GAAAACTACCTGTTCCTTGGCCAACACTTGTCACTACTTTCACTTATGGTGTTCAATGCTTTTCAAGATACCCAGATCATATGAAGCGG
CACGACTTCTTCAAGAGCGCCATGCCTGAGGGATACGTGCAGGAGAGGACCATCTTCTTCAAGGACGACGGGAACTACAAGACACGTGC
TGAAGTCAAGTTTGAGGGAGACACCCTCGTCAACAGGATCGAGCTTAAGGGAATCGATTTCAAGGAGGACGGAAACATCCTCGGCCACA
AGTTGGAATACAACTACAACTCCCACAACGTATACATCATGGCCGACAAGCAAAAGAACGGCATCAAAGCCAACTTCAAGACCCGCCAC
AACATCGAACACCATCACCATCACCATGACGGCGGCGTGCAACTCGCTGATCATTATCAACAAAATACTCCAATTGGCGATGGCCCTGT
CCTTTTACCAGACAACCATTACCTGTCCACACAATCTGCCCTTTCGAAAGATCCCAACGAAAAGAGAGACCACATGGTCCTTCTTGAGT
TTGTAACAGCTGCTGGGATTACACATGGCATGGATGAACTATACAAACTCGAGTATGCATTGTCCTTCGGAACTGAGATACTTACAGTT
GAATATGGACCACTTCCTATTGGAAAGATTGTGAGTGAAGAGATCAACTGCAGTGTTTATTCCGTGGATCCAGAGGGTAGAGTTTACAC
TCAAGCAATTGCTCAGTGGCATGATAGGGGAGAACAGGAGGTTCTTGAATATGAGTTGGAAGATGGTTCTGTGATAAGAGCTACATCAG
ATCACAGGTTTCTTACTACAGATTACCAACTTTTGGCAATCGAAGAGATTTTCGCTAGACAGCTCGATCTTCTCACTTTGGAAAATATT
AAGCAAACAGAAGAGGCACTTGATAACCATAGGCTTCCATTTCCTCTTTTGGATGCTGGAACTATTAAGATGGTTAAAGTGATAGGAAG
AAGGTCATTGGGTGTTCAAAGAATATTTGATATCGGACTTCCTCAGGATCACAATTTCTTACTCGCAAACGGTGCTATTGCTGCAGCTG
GTGGTTCTAGAGAGTCTGGAGCTATCTCTGGCGATAGTCTGATCAGCCTGGCTAGCaCAGGGAAAAAGAGTTTCTATTAAAGATTTGTta
gatGAAAAAGATTTTGAAATATGGGCAATTAATGAACAGACGATGAAGCTAGAATCAGCTAAAGTTAGTCGTGTATTTTGTACTGGCAA
AAAGCTAGTTTATATTCTAAAAACTCGACTAGGTAGAACTATCAAGGCAACAGCAAATCATAGATTTTTAACTATTGATGGTTGGAAAA
GATTAGATGAGCTATCTTTAAAAGAGCATATTGCTCTACCCCGTAAACTAGAAAGCTCCTCTTtaCAATTGTCaCCAGAAATAGAAAAG
TTGTCTCAGAGTGATATTTACTGGGACTCCATCGTTTCTATTACGGAGACTGGAGTCGAAGAGGTTTTTGATTTGACTGTGCCAGGACC
ACATAACTTTGTCGCGAATGACATCATTGTACACAACTGCCGCGGGCCCGTGAGCAAGGGCGAGGAGGATAACATGGCCATCATCAAGG
AGTTCATGCGCTTCAAGGTGCACATGGAGGGCTCCGTGAACGGCCACGAGTTCGAGATCGAGGGCGAGGGCGAGGGCCGCCCCTACGAG
GGCACCCAGACCGCCAAGCTGAAGGTGACCAAGGGTGGCCCCCTGCCCTTCGCCTGGGACATCCTGTCCCCTCAGTTCATGTACGGCTC
CAAGGCCTACGTGAAGCACCCCGCCGACATCCCCGACTACTTGAAGCTGTCCTTCCCCGAGGGCTTCAAGTGGGAGCGCGTGATGAACT
TCGAGGACGGCGGCGTGGTGACCGTGACCCAGGACTCCTCCCTGCAGGACGGCGAGTTCATCTACAAGGTGAAGCTGCGCGGCACCAAC
TTCCCCTCCGACGGCCCCGTAATGCAGAAGAAGACCATGGGCTGGGAGGCCTCCTCCGAGCGGATGTACCCCGAGGACGGCGCCCTGAA
GGGCGAGATCAAGCAGAGGCTGAAGCTGAAGGACGGCGGCCACTACGACGCTGAGGTCAAGACCACCTACAAGGCCAAGAAGCCCGTGC
AGCTGCCCGGCGCCTACAACGTCAACATCAAGTTGGACATCACCTCCCACAACGAGGACTACACCATCGTGGAACAGTACGAACGCGCC
GAGGGCCGCCACTCCACCGGCGGCATGGACGAGCTGTACAAGGGGTTCTGGATGGTCACATCCTCAGTTTGAAAAATGAGAGCTC
```

Figure 12A: GFP-intein-UB-mCherry sequence

Figure 12B: GFP-intein-UB-mCherry sequence

SEQ ID NO: 10

GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGAGGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGAAACATCCTCGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAATGTTTGTCCTTCGGAACTGAGATACTTACAGTTGAATATGGACCACTTCCT
ATTGGAAAGATTGTGAGTGAAGAGATCAACTGCAGTGTTTATTCCGTGGATCCAGAGGGTAGAGTTTACACTCAAGCAATT
GCTCAGTGGCATGATAGGGGAGAACAGGAGGTTCTTGAATATGAGTTGGAAGATGGTTCTGTGATAAGAGCTACATCAGAT
CACAGGTTTCTTACTACAGATTACCAACTTTTGGCAATCGAAGACATTTTCGCTAGACAGCTCGATCTTCTCACTTTGGAA
AATATTAAGCAAACAGAAGAGGCACTTGATAACCATAGGCTTCCATTTCCTCTTTTGGATGCTGGAACTATTAAGATGGTT
AAAGTGATAGGAAGAAGGTCATTGGGTGTTCAAAGAATATTTGATATCGGACTTCCTCAGGATCACAATTTCTTACTCGCA
AACGGTGCTATTGCTGCAGCTTGTTCTTGTGGTTCTGGTATGCAGATCTTCGTAAAGACTTTGACCGGAAAGACCATCACT
CTTGAAGTTGAAAGCTCCGACACCATTGATAACGTGAAGGCTAAGATCCAGGACAAGGAAGGCATTCCTCCGGACCAGCAG
CGTCTCATCTTCGCTGGAAGGCAGCTTGAGGATGGACGTACTTTGGCCGACTACAACATCCAGAAGGAGTCCACTCTTCAC
TTGGTCCTCCGTCTCCGCGGCGGTGTGAGCAAGGGCGAGGAGGATAACATGGCCATCATCAAGGAGTTCATGCGCTTCAAG
GTGCACATGGAGGGCTCCGTGAACGGCCACGAGTTCGAGATCGAGGGCGAGGGCGAGGGCCGCCCCTACGAGGGCACCCAG
ACCGCCAAGCTGAAGGTGACCAAGGGTGGCCCCCTGCCCTTCGCCTGGGACATCCTGTCCCCTCAGTTCATGTACGGCTCC
AAGGCCTACGTGAAGCACCCCGCCGACATCCCCGACTACTTGAAGCTGTCCTTCCCCGAGGGCTTCAAGTGGGAGCGCGTG
ATGAACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCGGATG
TACCCCGAGGACGGCGCCCTGAAGGGCGAGATCAAGCAGAGGCTGAAGCTGAAGGACGGCGGCCACTACGACGCTGAGGTC
AAGACCACCTACAAGGCCAAGAAGCCCGTGCAGCTGCCCGGCGCCTACAACGTCAACATCAAGTTGGACATCACCTCCCAC
AACGAGGACTACACCATCGTGGAACAGTACGAACGCGCCGAGGGCCGCCACTCCACCGGCGGCATGGACGAGCTGTACAAG
GGTTCTGGATGGTCACATCCTCAGTTTGAAAAATGAGAGCTC

Figure 13A: GFP-intein-SUMO-mCherry sequence

Figure 13B: GFP-intein-SUMO-mCherry – nucleotide sequence

SEQ ID NO: 26

```
GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGAGGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGAAACATCCTCGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAATGTTTGTCCTTCGGAACTGAGATACTTACAGTTGAATATGGACCACTTCCT
ATTGGAAAGATTGTGACTGAAGAGATCAACTGCAGTGTTTATTCCGTGGATCCAGAGGGTAGAGTTTACACTCAAGCAATT
GCTCAGTGGCATCATAGGGGAGAACAGGAGGTTCTTGAATATGAGTTCGAAGATGGTTCTGTGATAAGAGCTACATCAGAT
CACAGGTTTCTTACTACAGATTACCAACTTTTGGCAATCGAAGAGATTTTCGCTAGACAGCTCGATCTTCTCACTTTGGAA
AATATTAAGCAAACAGAAGAGGCACTTGATAACCATAGGCTTCCATTTCCTCTTTTGGATGCTGGAACTATTAAGATGGTT
AAAGTGATAGGAAGAAGGTCATTGCGTCTTCAAAGAATATTTGATATCGGACTTCCTCAGGATCACAATTTCTTACTCGCA
AACGGTGCTATTGCTGCAGCTTGTTCTTGTGGTTCTGGTATGTCTGACCAGGAGGCAAAACCTTCAACTGAGGACTTGGGG
GATAAGAAGGAAGGTGAATATATTAAACTCAAAGTCATTGGACAGGATAGCAGTGAGATTCACTTCAAAGTGAAAATGACA
ACACATCTCAAGAAACTCAAAGAATCATACTGTCAAAGACAGGGTGTTCCAATGAATTCACTCAGGTTTCTCTTTGAGGGT
CAGAGAATTGCTGATAATCATACTCCAAAAGAACTGGGAATGGAGGAAGAAGATGTGATTGAAGTTTATCAGGAACAAACG
GGGGGTCATTCAACAGTTGTGAGCAAGGGCGAGGAGGATAACATGGCCATCATCAAGGAGTTCATGCGCTTCAAGGTGCAC
ATGGAGGGCTCCGTGAACGGCCACGAGTTCGAGATCGAGGGCGAGGGCGAGGGCCGCCCCTACGAGGGCACCCAGACCGCC
AAGCTGAAGGTGACCAAGGGTGGCCCCCTGCCCTTCGCCTGGGACATCCTGTCCCCTCAGTTCATGTACGGCTCCAAGGCC
TACGTGAAGCACCCCGCCGACATCCCCGACTACTTGAAGCTGTCCTTCCCCGAGGGCTTCAAGTGGGAGCGCGTGATGAAC
TTCGAGGACGGCGGCGTGGTGACCGTGACCCAGGACTCCTCCCTGCAGGACGGCGAGTTCATCTACAAGGTGAAGCTGCGC
GGCACCAACTTCCCCTCCGACGGCCCCGTAATGCAGAAGAAGACCATGGGCTGGGAGGCCTCCTCCGAGCGGATGTACCCC
GAGGACGGCGCCCTGAAGGGCGAGATCAAGCAGAGGCTGAAGCTGAAGGACGGCGGCCACTACGACGCTGAGGTCAAGACC
ACCTACAAGGCCAAGAAGCCCGTGCAGCTGCCCGGCGCCTACAACGTCAACATCAAGTTGGACATCACCTCCCACAACGAG
GACTACACCATCGTGGAACAGTACGAACGCGCCGAGGGCCGCCACTCCACCGGCGGCATGGACGAGCTGTACAAGGGTTCT
GGATGGTCACATCCTCAGTTTGAAAAATGAGAGCTC
```

Figure 14A: GFP-Intein::2A-UBQ-mCherry sequence

Figure 14B: GFP-Intein::2A-UBQ-mCherry – nucleotide sequence

SEQ ID NO: 20

```
GGTACCGTCGACCAAGGAGATATAACAATGAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACTTACCCTTAAA
TTTATTTGCACTACTGGAAAACTACCTGTTCCTTGGCCAACACTTGTCACTACTTTCACTTATGGTGTTCAATGCTTTTCA
AGATACCCAGATCATATGAAGCGGCACGACTTCTTCAAGAGCGCCATGCCTGAGGGATACGTGCAGGAGAGGACCATCTTC
TTCAAGGACGACGGGAACTACAAGACACGTGCTGAAGTCAAGTTTGAGGGAGACACCCTCGTCAACAGGATCGAGCTTAAG
GGAATCGATTTCAAGGAGGACGGAAACATCCTCGGCCACAAGTTGGAATACAACTACAACTCCCACAACGTATACATCATG
GCCGACAAGCAAAAGAACGGCATCAAAGCCAACTTCAAGACCCGCCACAACATCGAACACCATCACCATCACCATGACGGC
GGCGTGCAACTCGCTGATCATTATCAACAAAATACTCCAATTGGCGATGGCCCTGTCCTTTTACCAGACAACCATTACCTG
TCCACACAATCTGCCCTTTCGAAAGATCCCAACGAAAAGAGAGACCACATGGTCCTTCTTGAGTTTGTAACAGCTGCTGGG
ATTACACATGGCATGGATGAACTATACAAATGTTTGTCCTTCGGAACTGAGATACTTACAGTTGAATATGGACCACTTCCT
ATTGGAAAGATTGTGAGTGAAGAGATCAACTGCAGTGTTTATTCCGTGGATCCAGAGGGTAGAGTTTACACTCAAGCAATT
GCTCAGTGGCATGATAGGGGAGAACAGGAGGTTCTTGAATATGAGTTGGAAGATGGTTCTGTGATAAGAGCTACATCAGAT
CACAGGTTTCTTACTACAGATTACCAACTTTTGGCAATCGAAGAGATTTTCGCTAGACAGCTCGATCTTCTCACTTTGGAA
AATATTAAGCAAACAGAAGAGGCACTTGATAACCATAGGCTTCCATTTCCTCTTTTGGATGCTGGAACTATTAAGATGGTT
AAAGTGATAGGAAGAAGGTCATTGGGTGTTCAAAGAATATTTGATATCGGACTTCCTCAGGATCACAATTTCTTACTCGCA
AACGGTGCTATTGCTGCAGCTTGTTCTTGTGGTTCTGGTTCTAGAGGATCTGGCGATGGATTCTGCATTCTCTATCTGCTC
CTGATCCTCTTGATGAGGTCTGGTGACGTTGAAACCAACCCTGGGCCCATGCAGATCTTCGTAAAGACTTTGACCGGAAAG
ACCATCACTCTTGAAGTTGAAAGCTCCGACACCATTGATAACGTGAAGGCTAAGATCCAGGACAAGGAAGGCATTCCTCCG
GACCAGCAGCGTCTCATCTTCGCTGGAAGGCAGCTTGAGGATGGACGTACTTTGGCCGACTACAACATCCAGAAGGAGTCC
ACTCTTCACTTGGTCCTCCGTCTCCGCGGCGGTGTGAGCAAGGGCGAGGAGGATAACATGGCCATCATCAAGGAGTTCATG
CGCTTCAAGGTGCACATGGAGGGCTCCGTGAACGGCCACGAGTTCGAGATCGAGGGCGAGGGCGAGGGCCGCCCCTACGAG
GGCACCCAGACCGCCAAGCTGAAGGTGACCAAGGGTGGCCCCCTGCCCTTCGCCTGGGACATCCTGTCCCCTCAGTTCATG
TACGGCTCCAAGGCCTACGTGAAGCACCCCGCCGACATCCCCGACTACTTGAAGCTGTCCTTCCCCGAGGGCTTCAAGTGG
GAGCGCGTGATGAACTTCGAGGACGGCGGCGTGGTGACCGTGACCCAGGACTCCTCCCTGCAGGACGGCGAGTTCATCTAC
AAGGTGAAGCTGCGCGGCACCAACTTCCCCTCCGACGGCCCCGTAATGCAGAAGAAGACCATGGGCTGGGAGGCCTCCTCC
GAGCGGATGTACCCCGAGGACGGCGCCCTGAAGGGCGAGATCAAGCAGAGGCTGAAGCTGAAGGACGGCGGCCACTACGAC
GCTGAGGTCAAGACCACCTACAAGGCCAAGAAGCCCGTGCAGCTGCCCGGCGCCTACAACGTCAACATCAAGTTGGACATC
ACCTCCCACAACGAGGACTACACCATCGTGGAACAGTACGAACGCGCCGAGGGCCGCCACTCCACCGGCGGCATGGACGAG
CTGTACAAGGGTTCTGGATGGTCACATCCTCAGTTTGAAAAATGAGAGCTC
```

FIGURE 16
GFP-Intein::F2A-CAT-strep:
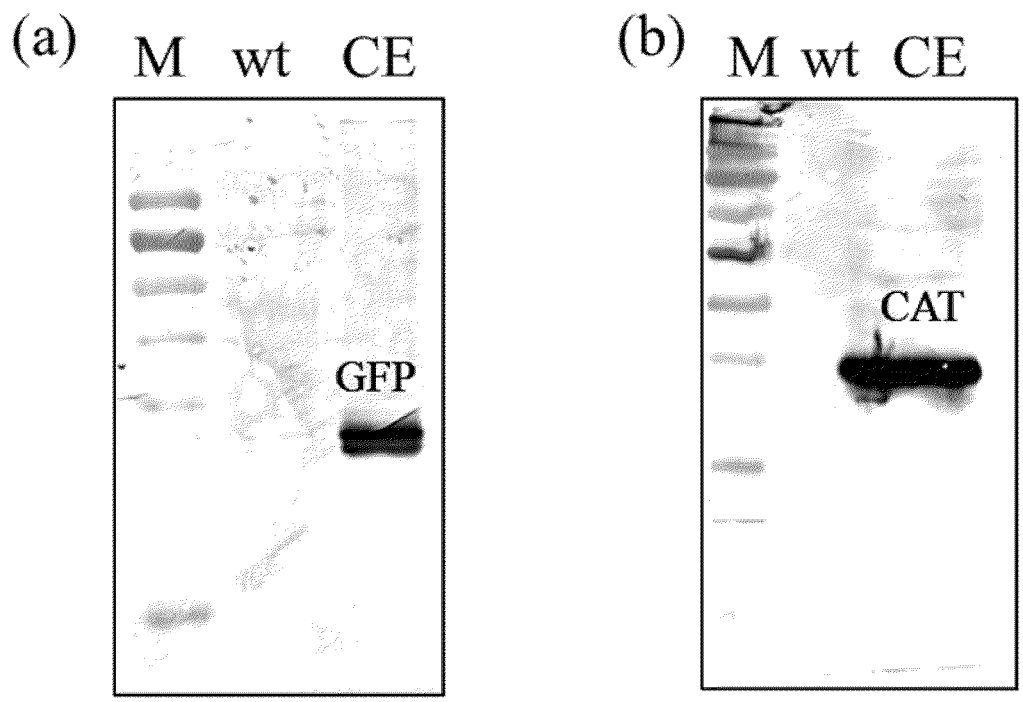
hGMCSF-Intein::F2A-mCherry-strep:
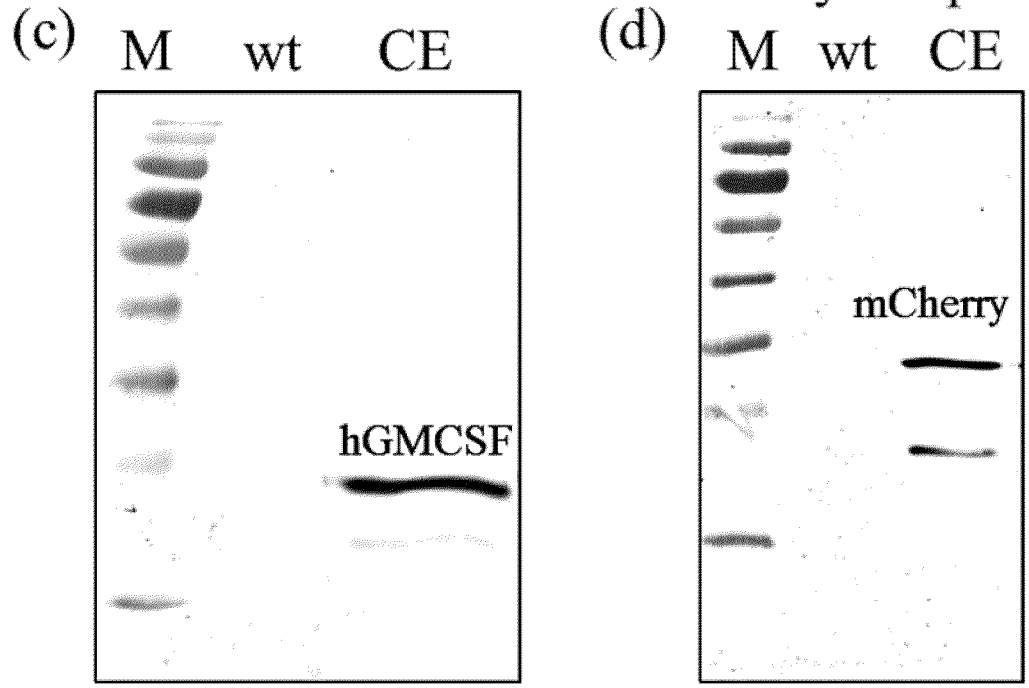

FIGURE 19
(A)
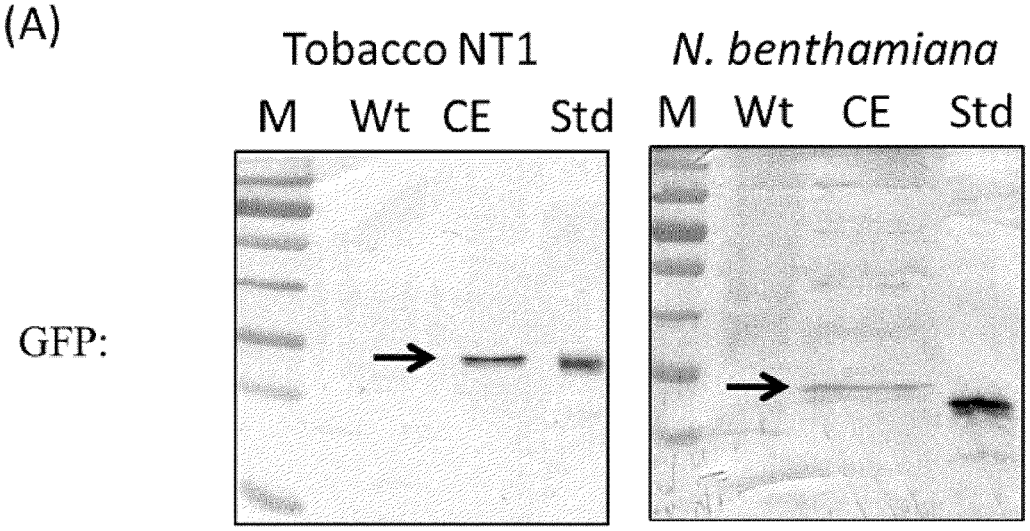
GFP:
(B)
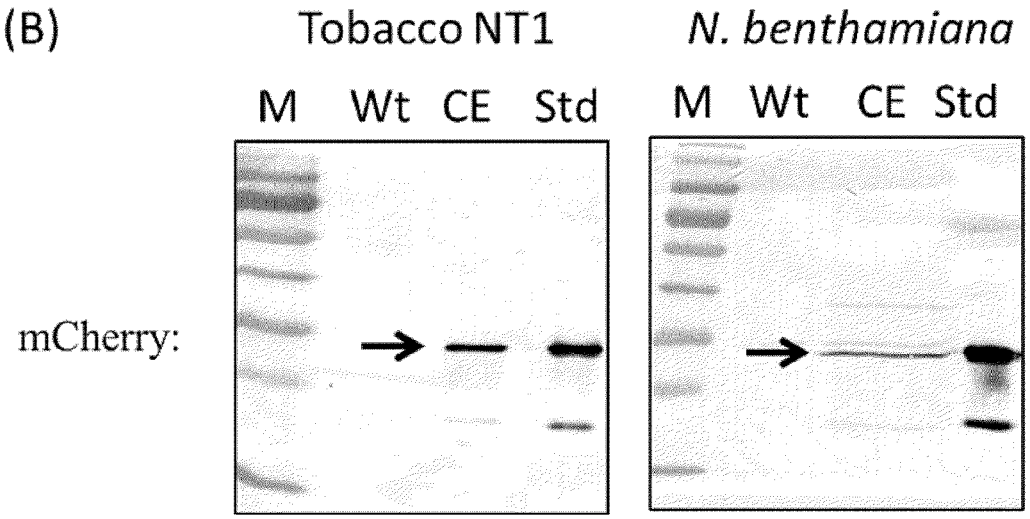
mCherry:

FIGURE 25
(A) N-cleavage active intein     N-cleavage inactive intein
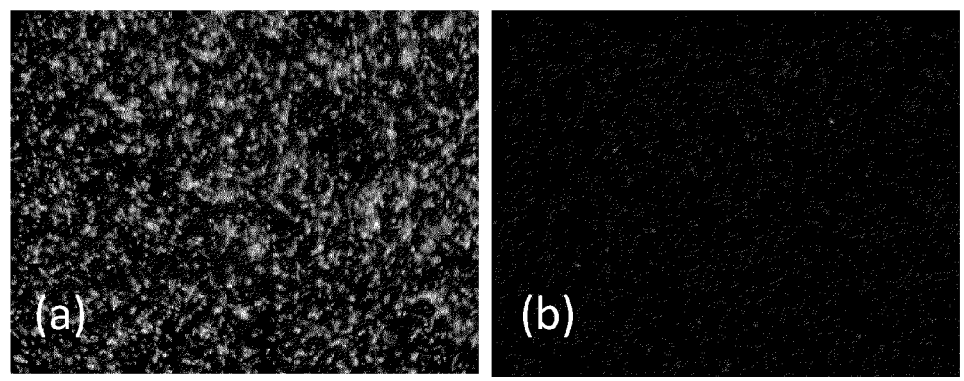
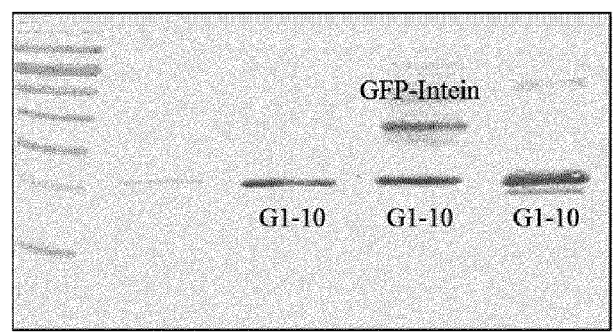

```
                            SEQUENCE LISTING

<160> NUMBER OF SEQ ID NOS: 54

<210> SEQ ID NO 1
<211> LENGTH: 159
<212> TYPE: PRT
<213> ORGANISM: Artificial Sequence
<220> FEATURE:
<223> OTHER INFORMATION: Ssp DnaE intein

<400> SEQUENCE: 1

Cys Leu Ser Phe Gly Thr Glu Ile Leu Thr Val Glu Tyr Gly Pro Leu
 1               5                   10                  15

Pro Ile Gly Lys Ile Val Ser Glu Glu Ile Asn Cys Ser Val Tyr Ser
                20                  25                  30

Val Asp Pro Glu Gly Arg Val Tyr Thr Gln Ala Ile Ala Gln Trp His
            35                  40                  45

Asp Arg Gly Glu Gln Glu Val Leu Glu Tyr Glu Leu Glu Asp Gly Ser
        50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
                100                 105                 110

Pro Phe Pro Leu Leu Asp Ala Gly Thr Ile Lys Met Val Lys Val Ile
            115                 120                 125

Gly Arg Arg Ser Leu Gly Val Gln Arg Ile Phe Asp Ile Gly Leu Pro
        130                 135                 140

Gln Asp His Asn Phe Leu Leu Ala Asn Gly Ala Ile Ala Ala Asn
145                 150                 155

<210> SEQ ID NO 2
<211> LENGTH: 76
<212> TYPE: PRT
<213> ORGANISM: Artificial Sequence
<220> FEATURE:
<223> OTHER INFORMATION: UB polypeptide

<400> SEQUENCE: 2

Met Gln Ile Phe Val Lys Thr Leu Thr Gly Lys Thr Ile Thr Leu Glu
 1               5                   10                  15

Val Glu Ser Ser Asp Thr Ile Asp Asn Val Lys Ala Lys Ile Gln Asp
                20                  25                  30

Lys Glu Gly Ile Pro Pro Asp Gln Gln Arg Leu Ile Phe Ala Gly Arg
            35                  40                  45
```

-continued

```
Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly
65                  70                  75

<210> SEQ ID NO 3
<211> LENGTH: 103
<212> TYPE: PRT
<213> ORGANISM: Artificial Sequence
<220> FEATURE:
<223> OTHER INFORMATION: SUMO polypeptide

<400> SEQUENCE: 3

Gly Ser Met Ser Asp Gln Glu Ala Lys Pro Ser Thr Glu Asp Leu Gly
1               5                   10                  15

Asp Lys Lys Glu Gly Glu Tyr Ile Lys Leu Lys Val Ile Gly Gln Asp
            20                  25                  30

Ser Ser Glu Ile His Phe Lys Val Lys Met Thr Thr His Leu Lys Lys
        35                  40                  45

Leu Lys Glu Ser Tyr Cys Gln Arg Gln Gly Val Pro Met Asn Ser Leu
    50                  55                  60

Arg Phe Leu Phe Glu Gly Gln Arg Ile Ala Asp Asn His Thr Pro Lys
65                  70                  75                  80

Glu Leu Gly Met Glu Glu Glu Asp Val Ile Glu Val Tyr Gln Glu Gln
                85                  90                  95

Thr Gly Gly His Ser Thr Val
            100

<210> SEQ ID NO 4
<211> LENGTH: 63
<212> TYPE: PRT
<213> ORGANISM: Artificial Sequence
<220> FEATURE:
<223> OTHER INFORMATION: FMDV 2A sequence

<400> SEQUENCE: 4

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 5
<211> LENGTH: 25
<212> TYPE: PRT
<213> ORGANISM: Artificial Sequence
<220> FEATURE:
<223> OTHER INFORMATION: (Strongylocentrotus purpuratus) 2A sequence

<400> SEQUENCE: 5

Asp Gly Phe Cys Ile Leu Tyr Leu Leu Leu Ile Leu Leu Met Arg Ser
1               5                   10                  15

Gly Asp Val Glu Thr Asn Pro Gly Pro
            20                  25

<210> SEQ ID NO 6
<211> LENGTH: 2367
<212> TYPE: DNA
```

<213> ORGANISM: Artificial Sequence
<220> FEATURE:
<223> OTHER INFORMATION: Intein 190 (pE1775-mGFP172-DnaE
    Intein-2A-mCherry-streptag)

<400> SEQUENCE: 6

```
ggtaccgtcg accaaggaga tataacaatg aagactaatc tttttctctt tctcatcttt      60
tcacttctcc tatcattatc ctcggccgaa ttcagtaaag gagaagaact tttcactgga     120
gttgtcccaa ttcttgttga attagatggt gatgttaatg gcacaaatt ttctgtcagt      180 ggagagggtg aaggtgatgc aacatacgga aaacttaccc ttaaatttat ttgcactact     240
ggaaaactac ctgttccttg gccaacactt gtcactactt tcacttatgg tgttcaatgc     300
ttttcaagat acccagatca tatgaagcgg cacgacttct tcaagagcgc catgcctgag     360
ggatacgtgc aggagaggac catcttcttc aaggacgacg gaactacaa gacacgtgct      420 gaagtcaagt ttgagggaga caccctcgtc aacaggatcg agcttaaggg aatcgatttc     480
aaggaggacg gaaacatcct cggccacaag ttgaatacaa ctacaactc ccacaacgta      540 tacatcatgg ccgacaagca aaagaacggc atcaaagcca acttcaagac ccgccacaac     600
atcgaacacc atcaccatca ccatgacggc ggcgtgcaac tcgctgatca ttatcaacaa     660
aatactccaa ttggcgatgg ccctgtcctt ttaccagaca accattacct gtccacacaa     720
tctgcccttt cgaaagatcc caacgaaaag agagaccaca tggtccttct tgagtttgta     780
acagctgctg ggattacaca tggcatggat gaactataca aactcgaggg aggatctaag     840
tttgcaaatg attgtttgtc cttcggaact gagatactta cagttgaata tggaccactt     900
cctattggaa agattgtgag tgaagagatc aactgcagtg tttattccgt ggatccagag     960
ggtagagttt acactcaagc aattgctcag tggcatgata ggggagaaca ggaggttctt    1020
gaatatgagt tggaagatgg ttctgtgata agagctacat cagatcacag gtttcttact    1080
acagattacc aacttttggc aatcgaagag attttcgcta gacagctcga tcttctcact    1140
ttggaaaata ttaagcaaac agaagaggca cttgataacc ataggcttcc atttcctctt    1200
ttggatgctg gaactattaa gatggttaaa gtgataggaa gaaggtcatt gggtgttcaa    1260
agaatatttg atatcggact tcctcaggat cacaatttct tactcgcaaa cggtgctatt    1320
gctgcagctt gtttcaatgg ttctggttct agagttactg agcttttgta taggatgaag    1380
agggcagaaa catactgccc aagaccttta ctcgcaatcc atccaacaga ggctaggcac    1440
aagcaaaaaa ttgttgctcc tgtgaaacag cttttgaact tgatcttct caagcttgcg     1500 ggagacgtcg agtccaaccc tgggcccag gtgctgaaca ccatggtgaa caaacacttc      1560
ttgtcccttt cggtcctcat cgtcctcctt ggcctctcct ccaacttgac agccggcatg    1620
ctgagcaagg gcgaggagga taacatggcc atcatcaagg agttcatgcg cttcaaggtg    1680
cacatggagg gctccgtgaa cggccacgag ttcgagatcg agggcgaggg cgagggccgc    1740
ccctacgagg caccagac cgccaagctg aaggtgacca agggtggccc cctgcccttc       1800
gcctgggaca tcctgtcccc tcagttcatg tacggctcca aggcctacgt gaagcacccc    1860
gccgacatcc ccgactactt gaagctgtcc ttccccgagg gcttcaagtg ggagcgcgtg    1920
atgaacttcg aggacggcgg cgtggtgacc gtgacccagg actcctccct gcaggacggc    1980
gagttcatct acaaggtgaa gctgcgcggc accaacttcc cctccgacgg ccccgtaatg    2040
cagaagaaga ccatgggctg ggaggcctcc tccgagcgga tgtaccccga ggacggcgcc    2100
ctgaagggcg agatcaagca gaggctgaag ctgaaggacg gcggccacta cgacgctgag    2160
```

```
gtcaagacca cctacaaggc caagaagccc gtgcagctgc ccggcgccta caacgtcaac    2220
atcaagttgg acatcacctc ccacaacgag gactacacca tcgtggaaca gtacgaacgc    2280
gccgagggcc gccactccac cggcggcatg gacgagctgt acaagggttc tggatggtca    2340
catcctcagt ttgaaaaatg agagctc                                        2367
```

<210> SEQ ID NO 7
<211> LENGTH: 777
<212> TYPE: PRT
<213> ORGANISM: Artificial Sequence
<220> FEATURE:
<223> OTHER INFORMATION: Intein 190 (pE1775-mGFP172-DnaE
      Intein-2A-mCherry-streptag)

<400> SEQUENCE: 7

```
Met Lys Thr Asn Leu Phe Leu Phe Leu Ile Phe Ser Leu Leu Leu Ser
  1               5                  10                  15

Leu Ser Ser Ala Glu Phe Ser Lys Gly Glu Glu Leu Phe Thr Gly Val
             20                  25                  30

Val Pro Ile Leu Val Glu Leu Asp Gly Asp Val Asn Gly His Lys Phe
         35                  40                  45

Ser Val Ser Gly Glu Gly Glu Gly Asp Ala Thr Tyr Gly Lys Leu Thr
     50                  55                  60

Leu Lys Phe Ile Cys Thr Thr Gly Lys Leu Pro Val Pro Trp Pro Thr
 65                  70                  75                  80

Leu Val Thr Thr Phe Thr Tyr Gly Val Gln Cys Phe Ser Arg Tyr Pro
                 85                  90                  95

Asp His Met Lys Arg His Asp Phe Phe Lys Ser Ala Met Pro Glu Gly
            100                 105                 110

Tyr Val Gln Glu Arg Thr Ile Phe Phe Lys Asp Asp Gly Asn Tyr Lys
        115                 120                 125

Thr Arg Ala Glu Val Lys Phe Glu Gly Asp Thr Leu Val Asn Arg Ile
    130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Ala Asn Phe Lys Thr Arg His Asn Ile
            180                 185                 190

Glu His His His His His His Asp Gly Gly Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr His Gly Met Asp Glu Leu Tyr Lys Leu Glu Gly Gly Ser Lys Phe
            260                 265                 270

Ala Asn Asp Cys Leu Ser Phe Gly Thr Glu Ile Leu Thr Val Glu Tyr
        275                 280                 285

Gly Pro Leu Pro Ile Gly Lys Ile Val Ser Glu Glu Ile Asn Cys Ser
    290                 295                 300

Val Tyr Ser Val Asp Pro Glu Gly Arg Val Tyr Thr Gln Ala Ile Ala
305                 310                 315                 320
```

-continued

```
Gln Trp His Asp Arg Gly Glu Gln Glu Val Leu Glu Tyr Glu Leu Glu
                325                 330                 335

Asp Gly Ser Val Ile Arg Ala Thr Ser Asp His Arg Phe Leu Thr Thr
            340                 345                 350

Asp Tyr Gln Leu Leu Ala Ile Glu Glu Ile Phe Ala Arg Gln Leu Asp
        355                 360                 365

Leu Leu Thr Leu Glu Asn Ile Lys Gln Thr Glu Glu Ala Leu Asp Asn
    370                 375                 380

His Arg Leu Pro Phe Pro Leu Leu Asp Ala Gly Thr Ile Lys Met Val
385                 390                 395                 400

Lys Val Ile Gly Arg Arg Ser Leu Gly Val Gln Arg Ile Phe Asp Ile
                405                 410                 415

Gly Leu Pro Gln Asp His Asn Phe Leu Leu Ala Asn Gly Ala Ile Ala
            420                 425                 430

Ala Ala Cys Phe Asn Gly Ser Gly Ser Arg Val Thr Glu Leu Leu Tyr
        435                 440                 445

Arg Met Lys Arg Ala Glu Thr Tyr Cys Pro Arg Pro Leu Leu Ala Ile
    450                 455                 460

His Pro Thr Glu Ala Arg His Lys Gln Lys Ile Val Ala Pro Val Lys
465                 470                 475                 480

Gln Leu Leu Asn Phe Asp Leu Leu Lys Leu Ala Gly Asp Val Glu Ser
                485                 490                 495

Asn Pro Gly Pro Gln Val Leu Asn Thr Met Val Asn Lys His Phe Leu
            500                 505                 510

Ser Leu Ser Val Leu Ile Val Leu Leu Gly Leu Ser Ser Asn Leu Thr
        515                 520                 525

Ala Gly Met Leu Ser Lys Gly Glu Glu Asp Asn Met Ala Ile Ile Lys
    530                 535                 540

Glu Phe Met Arg Phe Lys Val His Met Glu Gly Ser Val Asn Gly His
545                 550                 555                 560

Glu Phe Glu Ile Glu Gly Glu Gly Glu Gly Arg Pro Tyr Glu Gly Thr
                565                 570                 575

Gln Thr Ala Lys Leu Lys Val Thr Lys Gly Gly Pro Leu Pro Phe Ala
            580                 585                 590

Trp Asp Ile Leu Ser Pro Gln Phe Met Tyr Gly Ser Lys Ala Tyr Val
        595                 600                 605

Lys His Pro Ala Asp Ile Pro Asp Tyr Leu Lys Leu Ser Phe Pro Glu
    610                 615                 620

Gly Phe Lys Trp Glu Arg Val Met Asn Phe Glu Asp Gly Gly Val Val
625                 630                 635                 640

Thr Val Thr Gln Asp Ser Ser Leu Gln Asp Gly Glu Phe Ile Tyr Lys
                645                 650                 655

Val Lys Leu Arg Gly Thr Asn Phe Pro Ser Asp Gly Pro Val Met Gln
            660                 665                 670

Lys Lys Thr Met Gly Trp Glu Ala Ser Ser Glu Arg Met Tyr Pro Glu
        675                 680                 685

Asp Gly Ala Leu Lys Gly Glu Ile Lys Gln Arg Leu Lys Leu Lys Asp
    690                 695                 700

Gly Gly His Tyr Asp Ala Glu Val Lys Thr Thr Tyr Lys Ala Lys Lys
705                 710                 715                 720

Pro Val Gln Leu Pro Gly Ala Tyr Asn Val Asn Ile Lys Leu Asp Ile
                725                 730                 735

Thr Ser His Asn Glu Asp Tyr Thr Ile Val Glu Gln Tyr Glu Arg Ala
```

Glu Gly Arg His Ser Thr Gly Gly Met Asp Glu Leu Tyr Lys Gly Ser
         740             745                 750
Gly Trp Ser His Pro Gln Phe Glu Lys
    755                 760                         765
770                 775

<210> SEQ ID NO 8
<211> LENGTH: 2181
<212> TYPE: DNA
<213> ORGANISM: Artificial Sequence
<220> FEATURE:
<223> OTHER INFORMATION: Intein-26: pE1775-KpnI-SalI-mGFP172-DnaE
      intein-SC-2A-mCherry-Streptag

<400> SEQUENCE: 8

```
ggtaccgtcg accaaggaga tataacaatg agtaaaggag aagaactttt cactggagtt      60
gtcccaattc ttgttgaatt agatggtgat gttaatgggc acaaattttc tgtcagtgga     120
gagggtgaag gtgatgcaac atacggaaaa cttacccctta aatttatttg cactactgga    180
aaactacctg ttccttggcc aacacttgtc actactttca cttatggtgt tcaatgcttt     240
tcaagatacc cagatcatat gaagcggcac gacttcttca agagcgccat gcctgaggga     300
tacgtgcagg agaggaccat cttcttcaag gacgacggga actacaagac acgtgctgaa     360
gtcaagtttg agggagacac cctcgtcaac aggatcgagc ttaagggaat cgatttcaag     420
gaggacggaa acatcctcgg ccacaagttg gaatacaact acaactccca acgtatac      480
atcatggccg acaagcaaaa gaacggcatc aaagccaact tcaagacccg ccacaacatc     540
gaacaccatc accatcacca tgacggcggc gtgcaactcg ctgatcatta tcaacaaaat     600
actccaattg gcgatggccc tgtccttta ccagacaacc attacctgtc cacacaatct     660
gcccttcga aagatcccaa cgaaaagaga ccacatgg tccttcttga gtttgtaaca       720
gctgctggga ttacacatgg catgatgaa ctatacaaat gtttgtcctt cggaactgag      780
atacttacag ttgaatatgg accacttcct attggaaaga ttgtgagtga agagatcaac     840
tgcagtgttt attccgtgga tccagagggt agagtttaca ctcaagcaat tgctcagtgg     900
catgataggg agaacagga ggttcttgaa tatgagttgg aagatggttc tgtgataaga     960
gctacatcag atcacaggtt tcttactaca gattaccaac ttttggcaat cgaagagatt    1020
ttcgctagac agctcgatct tctcactttg gaaaatatta gcaaacaga gaggcactt     1080
gataaccata ggcttccatt tcctcttttg gatgctggaa ctattaagat ggttaaagtg    1140
ataggaagaa ggtcattggg tgttcaaaga atatttgata tcggacttcc tcaggatcac    1200
aatttcttac tcgcaaacgg tgctattgct gcagcttgtt cttgtggttc tggttctaga    1260
gttactgagc ttttgtatag gatgaagagg gcagaaacat actgcccaag acctttactc    1320
gcaatccatc aacagaggc taggcacaag caaaaaattg ttgctcctgt gaaacagctt    1380
ttgaactttg atcttctcaa gcttgcggga gacgtcgagt ccaaccctgg gcccgtgagc    1440
aagggcgagg aggataacat ggccatcatc aaggagttca tgcgcttcaa ggtgcacatg    1500
gagggctccg tgaacggcca cgagttcgag atcgagggcg agggcgaggg ccgcccctac    1560
gagggcaccc agaccgccaa gctgaaggtg accaaggtg gccccctgcc cttcgcctgg    1620
gacatcctgt cccctcagtt catgtacggc tccaaggcct acgtgaagca ccccgccgac    1680
atccccgact acttgaagct gtccttcccc gagggcttca gtgggagcg cgtgatgaac    1740
ttcgaggacg gcggcgtggt gaccgtgacc caggactcct ccctgcagga cggcgagttc    1800
```

```
atctacaagg tgaagctgcg cggcaccaac ttcccctccg acggcccccgt aatgcagaag   1860 aagaccatgg gctgggaggc ctcctccgag cggatgtacc ccgaggacgg cgccctgaag   1920
ggcgagatca agcagaggct gaagctgaag gacggcggcc actacgacgc tgaggtcaag   1980
accacctaca aggccaagaa gcccgtgcag ctgcccggcg cctacaacgt caacatcaag   2040
ttggacatca cctcccacaa cgaggactac accatcgtgg aacagtacga acgcgccgag   2100
ggccgccact ccaccggcgg catggacgag ctgtacaagg ttctggatgg gtcacatcct   2160
cagtttgaaa aatgagagct c                                              2181

<210> SEQ ID NO 9
<211> LENGTH: 715
<212> TYPE: PRT
<213> ORGANISM: Artificial Sequence
<220> FEATURE:
<223> OTHER INFORMATION: Intein-26: pE1775-KpnI-SalI-mGFP172-DnaE
      intein-SC-2A-mCherry-Streptag

<400> SEQUENCE: 9
```

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
    210                 215                 220

Val Leu Leu Glu Phe Val Thr Ala Ala Gly Ile Thr His Gly Met Asp
225                 230                 235                 240

Glu Leu Tyr Lys Cys Leu Ser Phe Gly Thr Glu Ile Leu Thr Val Glu
                245                 250                 255

Tyr Gly Pro Leu Pro Ile Gly Lys Ile Val Ser Glu Glu Ile Asn Cys
            260                 265                 270

Ser Val Tyr Ser Val Asp Pro Glu Gly Arg Val Tyr Thr Gln Ala Ile
        275                 280                 285

```
Ala Gln Trp His Asp Arg Gly Glu Gln Glu Val Leu Glu Tyr Glu Leu
    290                 295                 300

Glu Asp Gly Ser Val Ile Arg Ala Thr Ser Asp His Arg Phe Leu Thr
305                 310                 315                 320

Thr Asp Tyr Gln Leu Leu Ala Ile Glu Ile Phe Ala Arg Gln Leu
            325                 330                 335

Asp Leu Leu Thr Leu Glu Asn Ile Lys Gln Thr Glu Ala Leu Asp
            340                 345                 350

Asn His Arg Leu Pro Phe Pro Leu Asp Ala Gly Thr Ile Lys Met
        355                 360                 365

Val Lys Val Ile Gly Arg Arg Ser Leu Gly Val Gln Arg Ile Phe Asp
    370                 375                 380

Ile Gly Leu Pro Gln Asp His Asn Phe Leu Leu Ala Asn Gly Ala Ile
385                 390                 395                 400

Ala Ala Ala Cys Ser Cys Gly Ser Gly Ser Arg Val Thr Glu Leu Leu
                405                 410                 415

Tyr Arg Met Lys Arg Ala Glu Thr Tyr Cys Pro Arg Pro Leu Leu Ala
            420                 425                 430

Ile His Pro Thr Glu Ala Arg His Lys Gln Lys Ile Val Ala Pro Val
        435                 440                 445

Lys Gln Leu Leu Asn Phe Asp Leu Leu Lys Leu Ala Gly Asp Val Glu
    450                 455                 460

Ser Asn Pro Gly Pro Val Ser Lys Gly Glu Glu Asp Asn Met Ala Ile
465                 470                 475                 480

Ile Lys Glu Phe Met Arg Phe Lys Val His Met Glu Gly Ser Val Asn
                485                 490                 495

Gly His Glu Phe Glu Ile Glu Gly Glu Gly Glu Gly Arg Pro Tyr Glu
            500                 505                 510

Gly Thr Gln Thr Ala Lys Leu Lys Val Thr Lys Gly Gly Pro Leu Pro
        515                 520                 525

Phe Ala Trp Asp Ile Leu Ser Pro Gln Phe Met Tyr Gly Ser Lys Ala
    530                 535                 540

Tyr Val Lys His Pro Ala Asp Ile Pro Asp Tyr Leu Lys Leu Ser Phe
545                 550                 555                 560

Pro Glu Gly Phe Lys Trp Glu Arg Val Met Asn Phe Glu Asp Gly Gly
                565                 570                 575

Val Val Thr Val Thr Gln Asp Ser Ser Leu Gln Asp Gly Glu Phe Ile
            580                 585                 590

Tyr Lys Val Lys Leu Arg Gly Thr Asn Phe Pro Ser Asp Gly Pro Val
        595                 600                 605

Met Gln Lys Lys Thr Met Gly Trp Glu Ala Ser Ser Glu Arg Met Tyr
    610                 615                 620

Pro Glu Asp Gly Ala Leu Lys Gly Glu Ile Lys Gln Arg Leu Lys Leu
625                 630                 635                 640

Lys Asp Gly Gly His Tyr Asp Ala Glu Val Lys Thr Thr Tyr Lys Ala
                645                 650                 655

Lys Lys Pro Val Gln Leu Pro Gly Ala Tyr Asn Val Asn Ile Lys Leu
            660                 665                 670

Asp Ile Thr Ser His Asn Glu Asp Tyr Thr Ile Val Glu Gln Tyr Glu
        675                 680                 685

Arg Ala Glu Gly Arg His Ser Thr Gly Gly Met Asp Glu Leu Tyr Lys
    690                 695                 700

Gly Ser Gly Trp Ser His Pro Gln Phe Glu Lys
```

<210> SEQ ID NO 10
<211> LENGTH: 2229
<212> TYPE: DNA
<213> ORGANISM: Artificial Sequence
<220> FEATURE:
<223> OTHER INFORMATION: mGFP172-DnaE intein w/o
    N-extein-UBQ11-mCherry-streptag

<400> SEQUENCE: 10

```
ggtaccgtcg accaaggaga tataacaatg agtaaaggag aagaactttt cactggagtt      60
gtcccaattc ttgttgaatt agatggtgat gttaatgggc acaaattttc tgtcagtgga     120
gagggtgaag gtgatgcaac atacggaaaa cttaccctta aatttatttg cactactgga     180
aaactacctg ttccttggcc aacacttgtc actactttca cttatggtgt tcaatgcttt     240
tcaagatacc cagatcatat gaagcggcac gacttcttca gagcgccat gcctgaggga     300
tacgtgcagg agaggaccat cttcttcaag gacgacggga actacaagac acgtgctgaa     360
gtcaagtttg agggagacac cctcgtcaac aggatcgagc ttaagggaat cgatttcaag     420
gaggacggaa acatcctcgg ccacaagttg aatacaact acaactccca caacgtatac     480
atcatggccg acaagcaaaa gaacggcatc aaagccaact caagacccg ccacaacatc     540
gaacaccatc accatcacca tgacggcggc gtgcaactcg ctgatcatta tcaacaaaat     600
actccaattg gcgatggccc tgtccttta ccagacaacc attacctgtc cacacaatct     660
gccctttcga agatcccaa cgaaaagaga gaccacatgg tccttcttga gtttgtaaca     720
gctgctggga ttacacatgg catggatgaa ctatacaaat gttgtccttt cggaactgag     780
atacttacag ttgaatatgg accacttcct attggaaaga ttgtgagtga agatcaac     840
tgcagtgttt attccgtgga tccagagggt agagtttaca ctcaagcaat gctcagtgg     900
catgataggg gagaacagga ggttcttgaa tatgagttgg aagatggttc tgtgataaga     960
gctacatcag atcacaggtt tcttactaca gattaccaac ttttggcaat cgaagagatt    1020
ttcgctagac agctcgatct ctcactttg gaaaatatta agcaaacaga gaggcactt     1080
gataaccata ggcttccatt tcctctttg gatgctggaa ctattaagat ggttaaagtg    1140
ataggaagaa ggtcattggg tgttcaaaga atatttgata tcggacttcc tcaggatcac    1200
aatttcttac tcgcaaacgg tgctattgct gcagcttgtt cttgtggttc tggtatgcag    1260
atcttcgtaa agactttgac cggaaagacc atcactcttg aagttgaaag ctccgacacc    1320
attgataacg tgaaggctaa gatccaggac aaggaaggca ttcctccgga ccagcagcgt    1380
ctcatcttcg ctggaaggca gcttgaggat ggacgtactt tggccgacta caacatccag    1440
aaggagtcca ctcttcactt ggtcctccgt ctccgcggcg gtgtgagcaa gggcgaggag    1500
gataacatgg ccatcatcaa ggagttcatg cgcttcaagg tgcacatgga gggctccgtg    1560
aacggccacg agttcgagat cgagggcgag ggcgagggcc gcccctacga gggcacccag    1620
accgccaagc tgaaggtgac caagggtggc cccctgccct cgcctggga catcctgtcc    1680
cctcagttca tgtacggctc caaggcctac gtgaagcacc ccgccgacat ccccgactac    1740
ttgaagctgt ccttccccga gggcttcaag tgggagcgcg tgatgaactt cgaggacggc    1800
ggcgtggtga ccgtgaccca ggactcctcc ctgcaggacg gcgagttcat ctacaaggtg    1860
aagctgcgcg gcaccaactt cccctccgac ggccccgtaa tgcagaagaa gaccatgggc    1920
tgggaggcct cctccgagcg gatgtacccc gaggacggcg ccctgaaggg cgagatcaag    1980
```

US 8,945,876 B2

| | | | | |
|---|---|---|---|---|
| cagaggctga | agctgaagga | cggcggccac | tacgacgctg | aggtcaagac cacctacaag | 2040 |
| gccaagaagc | ccgtgcagct | gcccggcgcc | tacaacgtca | acatcaagtt ggacatcacc | 2100 |
| tcccacaacg | aggactacac | catcgtggaa | cagtacgaac | gcgccgaggg ccgccactcc | 2160 |
| accggcggca | tggacgagct | gtacaagggt | tctggatggt | cacatcctca gtttgaaaaa | 2220 |
| tgagagctc | | | | | 2229 |

<210> SEQ ID NO 11
<211> LENGTH: 731
<212> TYPE: PRT
<213> ORGANISM: Artificial Sequence
<220> FEATURE:
<223> OTHER INFORMATION: mGFP172-DnaE intein w/o
    N-extein-UBQ11-mCherry-streptag

<400> SEQUENCE: 11

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
    210                 215                 220

Val Leu Leu Glu Phe Val Thr Ala Ala Gly Ile Thr His Gly Met Asp
225                 230                 235                 240

Glu Leu Tyr Lys Cys Leu Ser Phe Gly Thr Glu Ile Leu Thr Val Glu
                245                 250                 255

Tyr Gly Pro Leu Pro Ile Gly Lys Ile Val Ser Glu Glu Ile Asn Cys
            260                 265                 270

Ser Val Tyr Ser Val Asp Pro Glu Gly Arg Val Tyr Thr Gln Ala Ile
        275                 280                 285

Ala Gln Trp His Asp Arg Gly Glu Gln Glu Val Leu Glu Tyr Glu Leu
    290                 295                 300

Glu Asp Gly Ser Val Ile Arg Ala Thr Ser Asp His Arg Phe Leu Thr

```
305                 310                 315                 320
Thr Asp Tyr Gln Leu Leu Ala Ile Glu Glu Ile Phe Ala Arg Gln Leu
                325                 330                 335

Asp Leu Leu Thr Leu Glu Asn Ile Lys Gln Thr Glu Ala Leu Asp
                340                 345                 350

Asn His Arg Leu Pro Phe Pro Leu Asp Ala Gly Thr Ile Lys Met
                355                 360                 365

Val Lys Val Ile Gly Arg Arg Ser Leu Gly Val Gln Arg Ile Phe Asp
370                 375                 380

Ile Gly Leu Pro Gln Asp His Asn Phe Leu Leu Ala Asn Gly Ala Ile
385                 390                 395                 400

Ala Ala Ala Cys Ser Cys Gly Ser Gly Met Gln Ile Phe Val Lys Thr
                405                 410                 415

Leu Thr Gly Lys Thr Ile Thr Leu Glu Val Glu Ser Ser Asp Thr Ile
                420                 425                 430

Asp Asn Val Lys Ala Lys Ile Gln Asp Lys Glu Gly Ile Pro Pro Asp
                435                 440                 445

Gln Gln Arg Leu Ile Phe Ala Gly Arg Gln Leu Glu Asp Gly Arg Thr
                450                 455                 460

Leu Ala Asp Tyr Asn Ile Gln Lys Glu Ser Thr Leu His Leu Val Leu
465                 470                 475                 480

Arg Leu Arg Gly Gly Val Ser Lys Gly Glu Glu Asp Asn Met Ala Ile
                485                 490                 495

Ile Lys Glu Phe Met Arg Phe Lys Val His Met Glu Gly Ser Val Asn
                500                 505                 510

Gly His Glu Phe Glu Ile Glu Gly Glu Gly Glu Gly Arg Pro Tyr Glu
                515                 520                 525

Gly Thr Gln Thr Ala Lys Leu Lys Val Thr Lys Gly Gly Pro Leu Pro
                530                 535                 540

Phe Ala Trp Asp Ile Leu Ser Pro Gln Phe Met Tyr Gly Ser Lys Ala
545                 550                 555                 560

Tyr Val Lys His Pro Ala Asp Ile Pro Asp Tyr Leu Lys Leu Ser Phe
                565                 570                 575

Pro Glu Gly Phe Lys Trp Glu Arg Val Met Asn Phe Glu Asp Gly Gly
                580                 585                 590

Val Val Thr Val Thr Gln Asp Ser Ser Leu Gln Asp Gly Glu Phe Ile
                595                 600                 605

Tyr Lys Val Lys Leu Arg Gly Thr Asn Phe Pro Ser Asp Gly Pro Val
                610                 615                 620

Met Gln Lys Lys Thr Met Gly Trp Glu Ala Ser Ser Glu Arg Met Tyr
625                 630                 635                 640

Pro Glu Asp Gly Ala Leu Lys Gly Glu Ile Lys Gln Arg Leu Lys Leu
                645                 650                 655

Lys Asp Gly Gly His Tyr Asp Ala Glu Val Lys Thr Thr Tyr Lys Ala
                660                 665                 670

Lys Lys Pro Val Gln Leu Pro Gly Ala Tyr Asn Val Asn Ile Lys Leu
                675                 680                 685

Asp Ile Thr Ser His Asn Glu Asp Tyr Thr Ile Val Glu Gln Tyr Glu
                690                 695                 700

Arg Ala Glu Gly Arg His Ser Thr Gly Gly Met Asp Glu Leu Tyr Lys
705                 710                 715                 720

Gly Ser Gly Trp Ser His Pro Gln Phe Glu Lys
                725                 730
```

<210> SEQ ID NO 12
<211> LENGTH: 2082
<212> TYPE: DNA
<213> ORGANISM: Artificial Sequence
<220> FEATURE:
<223> OTHER INFORMATION: pE1775-Int261 (KpnISalI-GFP172-DnaE Intein w/o
      N-exteins-Sea urchin 2A-mCherry-streptag)

<400> SEQUENCE: 12

```
ggtaccgtcg accaaggaga tataacaatg agtaaaggag aagaactttt cactggagtt      60
gtcccaattc ttgttgaatt agatggtgat gttaatgggc acaaattttc tgtcagtgga     120
gagggtgaag gtgatgcaac atacggaaaa cttacccta  aatttatttg cactactgga     180
aaactacctg ttccttggcc aacacttgtc actactttca cttatggtgt tcaatgcttt     240
tcaagatacc cagatcatat gaagcggcac gacttcttca agagcgccat gcctgaggga     300
tacgtgcagg agaggaccat cttcttcaag gacgacggga actacaagac acgtgctgaa     360
gtcaagtttg agggagacac cctcgtcaac aggatcgagc ttaagggaat cgatttcaag     420
gaggacggaa acatcctcgg ccacaagttg gaatacaact acaactccca caacgtatac     480
atcatggccg acaagcaaaa gaacggcatc aaagccaact caagacccg  ccacaacatc     540
gaacaccatc accatcacca tgacggcggc gtgcaactcg ctgatcatta tcaacaaaat     600
actccaattg gcgatggccc tgtccttta  ccagacaacc attacctgtc cacacaatct     660
gccctttcga aagatcccaa cgaaaagaga gaccacatgg tccttcttga gtttgtaaca     720
gctgctggga ttacacatgg catggatgaa ctatacaaat gtttgtcctt cggaactgag     780
atacttacag ttgaatatgg accacttcct attggaaaga ttgtgagtga agagatcaac     840
tgcagtgttt attccgtgga tccagagggt agagtttaca ctcaagcaat tgctcagtgg     900
catgataggg gagaacagga ggttcttgaa tatgagttgg aagatggttc tgtgataaga     960
gctacatcag atcacaggtt tcttactaca gattaccaac ttttggcaat cgaagagatt    1020
ttcgctagac agctcgatct tctcactttg gaaaatatta gcaaacaga  agaggcactt    1080
gataaccata ggcttccatt tcctcttttg gatgctggaa ctattaagat ggttaaagtg    1140
ataggaagaa ggtcattggg tgttcaaaga atatttgata tcggacttcc tcaggatcac    1200
aatttcttac tcgcaaacgg tgctattgct gcagcttgtt cttgtggttc tggttctaga    1260
gatggattct gcattctcta tctgctcctg atcctcttga tgagatctgg tgacgttgaa    1320
accaatccag ggcccgtgag caagggcgag gaggataaca tggccatcat caaggagttc    1380
atgcgcttca aggtgcacat ggagggctcc gtgaacggcc acgagttcga gatcgagggc    1440
gagggcgagg gccgcccta  cgagggcacc cagaccgcca agctgaaggt gaccaagggt    1500
ggccccctgc ccttcgcctg gacatcctg  tcccctcagt tcatgtacgg ctccaaggcc    1560
tacgtgaagc accccgccga catccccgac tacttgaagc tgtccttccc cgagggcttc    1620
aagtgggagc gcgtgatgaa cttcgaggac ggcggcgtgg tgaccgtgac ccaggactcc    1680
tccctgcagg acggcgagtt catctacaag gtgaagctgc gcggcaccaa cttcccctcc    1740
gacggccccg taatgcagaa gaagaccatg ggctgggagg cctcctccga gcggatgtac    1800
cccgaggacg gcgccctgaa gggcgagatc aagcagaggc tgaagctgaa ggacggcggc    1860
cactacgacg ctgaggtcaa gaccacctac aaggccaaga gcccgtgca  gctgcccggc    1920
gcctacaact caacatcaa  gttggacatc acctcccaca acgaggacta caccatcgtg    1980
gaacagtacg aacgcgccga gggccgccac tccaccggcg gcatggacga gctgtacaag    2040
```

```
ggttctggat ggtcacatcc tcagtttgaa aaatgagagc tc                    2082
```

<210> SEQ ID NO 13
<211> LENGTH: 682
<212> TYPE: PRT
<213> ORGANISM: Artificial Sequence
<220> FEATURE:
<223> OTHER INFORMATION: pE1775-Int261 (KpnISalI-GFP172-DnaE Intein w/o
      N-exteins-Sea urchin 2A-mCherry-streptag)

<400> SEQUENCE: 13

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
    210                 215                 220

Val Leu Leu Glu Phe Val Thr Ala Ala Gly Ile Thr His Gly Met Asp
225                 230                 235                 240

Glu Leu Tyr Lys Cys Leu Ser Phe Gly Thr Glu Ile Leu Thr Val Glu
                245                 250                 255

Tyr Gly Pro Leu Pro Ile Gly Lys Ile Val Ser Glu Glu Ile Asn Cys
            260                 265                 270

Ser Val Tyr Ser Val Asp Pro Glu Gly Arg Val Tyr Thr Gln Ala Ile
        275                 280                 285

Ala Gln Trp His Asp Arg Gly Glu Gln Glu Val Leu Glu Tyr Glu Leu
    290                 295                 300

Glu Asp Gly Ser Val Ile Arg Ala Thr Ser Asp His Arg Phe Leu Thr
305                 310                 315                 320

Thr Asp Tyr Gln Leu Leu Ala Ile Glu Glu Ile Phe Ala Arg Gln Leu
                325                 330                 335

Asp Leu Leu Thr Leu Glu Asn Ile Lys Gln Thr Glu Glu Ala Leu Asp
            340                 345                 350
```

Asn His Arg Leu Pro Phe Pro Leu Leu Asp Ala Gly Thr Ile Lys Met
        355                 360                 365

Val Lys Val Ile Gly Arg Arg Ser Leu Gly Val Gln Arg Ile Phe Asp
    370                 375                 380

Ile Gly Leu Pro Gln Asp His Asn Phe Leu Leu Ala Asn Gly Ala Ile
385                 390                 395                 400

Ala Ala Ala Cys Ser Cys Gly Ser Gly Ser Arg Asp Gly Phe Cys Ile
                405                 410                 415

Leu Tyr Leu Leu Leu Ile Leu Leu Met Arg Ser Gly Asp Val Glu Thr
            420                 425                 430

Asn Pro Gly Pro Val Ser Lys Gly Glu Glu Asp Asn Met Ala Ile Ile
                435                 440                 445

Lys Glu Phe Met Arg Phe Lys Val His Met Glu Gly Ser Val Asn Gly
450                 455                 460

His Glu Phe Glu Ile Glu Gly Glu Gly Glu Gly Arg Pro Tyr Glu Gly
465                 470                 475                 480

Thr Gln Thr Ala Lys Leu Lys Val Thr Lys Gly Gly Pro Leu Pro Phe
                    485                 490                 495

Ala Trp Asp Ile Leu Ser Pro Gln Phe Met Tyr Gly Ser Lys Ala Tyr
                500                 505                 510

Val Lys His Pro Ala Asp Ile Pro Asp Tyr Leu Lys Leu Ser Phe Pro
            515                 520                 525

Glu Gly Phe Lys Trp Glu Arg Val Met Asn Phe Glu Asp Gly Gly Val
530                 535                 540

Val Thr Val Thr Gln Asp Ser Ser Leu Gln Asp Gly Glu Phe Ile Tyr
545                 550                 555                 560

Lys Val Lys Leu Arg Gly Thr Asn Phe Pro Ser Asp Gly Pro Val Met
                565                 570                 575

Gln Lys Lys Thr Met Gly Trp Glu Ala Ser Ser Glu Arg Met Tyr Pro
                580                 585                 590

Glu Asp Gly Ala Leu Lys Gly Glu Ile Lys Gln Arg Leu Lys Leu Lys
            595                 600                 605

Asp Gly Gly His Tyr Asp Ala Glu Val Lys Thr Thr Tyr Lys Ala Lys
610                 615                 620

Lys Pro Val Gln Leu Pro Gly Ala Tyr Asn Val Asn Ile Lys Leu Asp
625                 630                 635                 640

Ile Thr Ser His Asn Glu Asp Tyr Thr Ile Val Glu Gln Tyr Glu Arg
                645                 650                 655

Ala Glu Gly Arg His Ser Thr Gly Gly Met Asp Glu Leu Tyr Lys Gly
            660                 665                 670

Ser Gly Trp Ser His Pro Gln Phe Glu Lys
            675                 680

<210> SEQ ID NO 14
<211> LENGTH: 2520
<212> TYPE: DNA
<213> ORGANISM: Artificial Sequence
<220> FEATURE:
<223> OTHER INFORMATION: Intein-Intein: DI-2 (GFP-172(His)6-Ssp DnaE
      intein - Ssp DnaB intein-mCherry-Strep Tag

<400> SEQUENCE: 14
ggtaccgtcg accaaggaga tataacaatg agtaaaggag aagaactttt cactggagtt      60
gtcccaattc ttgttgaatt agatggtgat gttaatgggc acaaattttc tgtcagtgga     120

| | |
|---|---|
| gagggtgaag gtgatgcaac atacggaaaa cttaccctta aatttatttg cactactgga | 180 |
| aaactacctg ttccttggcc aacacttgtc actactttca cttatggtgt tcaatgcttt | 240 |
| tcaagatacc cagatcatat gaagcggcac gacttcttca agagcgccat gcctgaggga | 300 |
| tacgtgcagg agaggaccat cttcttcaag gacgacggga actacaagac acgtgctgaa | 360 |
| gtcaagtttg agggagacac cctcgtcaac aggatcgagc ttaagggaat cgatttcaag | 420 |
| gaggacggaa acatcctcgg ccacaagttg aatacaact acaactccca caacgtatac | 480 |
| atcatggccg acaagcaaaa gaacggcatc aaagccaact tcaagacccg ccacaacatc | 540 |
| gaacaccatc accatcacca tgacggcggc gtgcaactcg ctgatcatta tcaacaaaat | 600 |
| actccaattg gcgatggccc tgtccttta ccagacaacc attacctgtc cacacaatct | 660 |
| gccctttcga aagatcccaa cgaaaagaga gaccacatgg tccttcttga gtttgtaaca | 720 |
| gctgctggga ttacacatgg catggatgaa ctatacaaac tcgagggagg atctaagttt | 780 |
| gcaaatgatt gtttgtcctt cggaactgag atacttacag ttgaatatgg accacttcct | 840 |
| attggaaaga ttgtgagtga agagatcaac tgcagtgttt attccgtgga tccagagggt | 900 |
| agagtttaca ctcaagcaat tgctcagtgg catgataggg gagaacagga ggttcttgaa | 960 |
| tatgagttgg aagatggttc tgtgataaga gctacatcag atcacaggtt tcttactaca | 1020 |
| gattaccaac ttttggcaat cgaagagatt ttcgctagac agctcgatct tctcactttg | 1080 |
| gaaaatatta agcaaacaga gaggcacttt gataaccata ggcttccatt tcctcttttg | 1140 |
| gatgctggaa ctattaagat ggttaaagtg ataggaagaa ggtcattggg tgttcaaaga | 1200 |
| atatttgata tcggacttcc tcaggatcac aatttcttac tcgcaaacgg tgctattgct | 1260 |
| gcagcttgtt tcaatggttc tggttctaga gagtctggag ctatctctgg cgatagtctg | 1320 |
| atcagcctgg ctagcacagg aaaaagagtt tctattaaag atttgttaga tgaaaaagat | 1380 |
| tttgaaatat gggcaattaa tgaacagacg atgaagctag aatcagctaa agttagtcgt | 1440 |
| gtattttgta ctggcaaaaa gctagtttat attctaaaaa ctcgactagg tagaactatc | 1500 |
| aaggcaacag caaatcatag attttaact attgatggtt ggaaaagatt agatgagcta | 1560 |
| tctttaaaag agcatattgc tctacccccgt aaactagaaa gctcctcttt acaattgtca | 1620 |
| ccagaaatag aaaagttgtc tcagagtgat atttactggg actccatcgt ttctattacg | 1680 |
| gagactggag tcgaagaggt ttttgatttg actgtgccag gaccacataa ctttgtcgcg | 1740 |
| aatgacatca ttgtacacaa cagccgcggg cccgtgagca agggcgagga ggataacatg | 1800 |
| gccatcatca aggagttcat gcgcttcaag gtgcacatgg agggctccgt gaacggccac | 1860 |
| gagttcgaga tcgagggcga gggcgagggc cgcccctacg agggcaccca gaccgccaag | 1920 |
| ctgaaggtga ccaagggtgg ccccctgccc ttcgcctggg acatcctgtc ccctcagttc | 1980 |
| atgtacggct ccaaggccta cgtgaagcac cccgccgaca tccccgacta cttgaagctg | 2040 |
| tccttccccg agggcttcaa gtgggagcgc gtgatgaact tcgaggacgg cggcgtggtg | 2100 |
| accgtgaccc aggactcctc cctgcaggac ggcgagttca tctacaaggt gaagctgcgc | 2160 |
| ggcaccaact tcccctccga cggccccgta atgcagaaga gaccatgggg ctgggaggcc | 2220 |
| tcctccgagc ggatgtaccc cgaggacggc gccctgaagg gcgagatcaa gcagaggctg | 2280 |
| aagctgaagg acggcggcca ctacgacgct gaggtcaaga ccacctacaa ggccaagaag | 2340 |
| cccgtgcagc tgcccggcgc ctacaacgtc aacatcaagt tggacatcac ctcccacaac | 2400 |
| gaggactaca ccatcgtgga acagtacgaa cgcgccgagg gccgccactc caccggcggc | 2460 |
| atggacgagc tgtacaaggg ttctggatgg tcacatcctc agtttgaaaa atgagagctc | 2520 |

<210> SEQ ID NO 15
<211> LENGTH: 828
<212> TYPE: PRT
<213> ORGANISM: Artificial Sequence
<220> FEATURE:
<223> OTHER INFORMATION: Intein-Intein: DI-2 (GFP-172(His)6-Ssp DnaE intein - Ssp DnaB intein-mCherry-Strep Tag

<400> SEQUENCE: 15

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
    210                 215                 220

Val Leu Leu Glu Phe Val Thr Ala Ala Gly Ile Thr His Gly Met Asp
225                 230                 235                 240

Glu Leu Tyr Lys Leu Glu Gly Gly Ser Lys Phe Ala Asn Asp Cys Leu
                245                 250                 255

Ser Phe Gly Thr Glu Ile Leu Thr Val Glu Tyr Gly Pro Leu Pro Ile
            260                 265                 270

Gly Lys Ile Val Ser Glu Glu Ile Asn Cys Ser Val Tyr Ser Val Asp
        275                 280                 285

Pro Glu Gly Arg Val Tyr Thr Gln Ala Ile Ala Gln Trp His Asp Arg
    290                 295                 300

Gly Glu Gln Glu Val Leu Glu Tyr Glu Leu Glu Asp Gly Ser Val Ile
305                 310                 315                 320

Arg Ala Thr Ser Asp His Arg Phe Leu Thr Thr Asp Tyr Gln Leu Leu
                325                 330                 335

Ala Ile Glu Glu Ile Phe Ala Arg Gln Leu Asp Leu Leu Thr Leu Glu
            340                 345                 350

Asn Ile Lys Gln Thr Glu Glu Ala Leu Asp Asn His Arg Leu Pro Phe
```

```
            355                 360                 365
Pro Leu Leu Asp Ala Gly Thr Ile Lys Met Val Lys Val Ile Gly Arg
370                 375                 380

Arg Ser Leu Gly Val Gln Arg Ile Phe Asp Ile Gly Leu Pro Gln Asp
385                 390                 395                 400

His Asn Phe Leu Leu Ala Asn Gly Ala Ile Ala Ala Ala Cys Phe Asn
                    405                 410                 415

Gly Ser Gly Ser Arg Glu Ser Gly Ala Ile Ser Gly Asp Ser Leu Ile
                420                 425                 430

Ser Leu Ala Ser Thr Gly Lys Arg Val Ser Ile Lys Asp Leu Leu Asp
                435                 440                 445

Glu Lys Asp Phe Glu Ile Trp Ala Ile Asn Glu Gln Thr Met Lys Leu
450                 455                 460

Glu Ser Ala Lys Val Ser Arg Val Phe Cys Thr Gly Lys Lys Leu Val
465                 470                 475                 480

Tyr Ile Leu Lys Thr Arg Leu Gly Arg Thr Ile Lys Ala Thr Ala Asn
                    485                 490                 495

His Arg Phe Leu Thr Ile Asp Gly Trp Lys Arg Leu Asp Glu Leu Ser
                500                 505                 510

Leu Lys Glu His Ile Ala Leu Pro Arg Lys Leu Glu Ser Ser Ser Leu
                515                 520                 525

Gln Leu Ser Pro Glu Ile Glu Lys Leu Ser Gln Ser Asp Ile Tyr Trp
530                 535                 540

Asp Ser Ile Val Ser Ile Thr Glu Thr Gly Val Glu Glu Val Phe Asp
545                 550                 555                 560

Leu Thr Val Pro Gly Pro His Asn Phe Val Ala Asn Asp Ile Ile Val
                    565                 570                 575

His Asn Ser Arg Gly Pro Val Ser Lys Gly Glu Glu Asp Asn Met Ala
                580                 585                 590

Ile Ile Lys Glu Phe Met Arg Phe Lys Val His Met Glu Gly Ser Val
                595                 600                 605

Asn Gly His Glu Phe Glu Ile Glu Gly Glu Gly Glu Gly Arg Pro Tyr
610                 615                 620

Glu Gly Thr Gln Thr Ala Lys Leu Lys Val Thr Lys Gly Gly Pro Leu
625                 630                 635                 640

Pro Phe Ala Trp Asp Ile Leu Ser Pro Gln Phe Met Tyr Gly Ser Lys
                    645                 650                 655

Ala Tyr Val Lys His Pro Ala Asp Ile Pro Asp Tyr Leu Lys Leu Ser
                660                 665                 670

Phe Pro Glu Gly Phe Lys Trp Glu Arg Val Met Asn Phe Glu Asp Gly
                675                 680                 685

Gly Val Val Thr Val Thr Gln Asp Ser Ser Leu Gln Asp Gly Glu Phe
                690                 695                 700

Ile Tyr Lys Val Lys Leu Arg Gly Thr Asn Phe Pro Ser Asp Gly Pro
705                 710                 715                 720

Val Met Gln Lys Lys Thr Met Gly Trp Glu Ala Ser Ser Glu Arg Met
                    725                 730                 735

Tyr Pro Glu Asp Gly Ala Leu Lys Gly Glu Ile Lys Gln Arg Leu Lys
                740                 745                 750

Leu Lys Asp Gly Gly His Tyr Asp Ala Glu Val Lys Thr Thr Tyr Lys
                755                 760                 765

Ala Lys Lys Pro Val Gln Leu Pro Gly Ala Tyr Asn Val Asn Ile Lys
770                 775                 780
```

Leu Asp Ile Thr Ser His Asn Glu Asp Tyr Thr Ile Val Glu Gln Tyr
785                 790                 795                 800

Glu Arg Ala Glu Gly Arg His Ser Thr Gly Gly Met Asp Glu Leu Tyr
            805                 810                 815

Lys Gly Ser Gly Trp Ser His Pro Gln Phe Glu Lys
            820                 825

<210> SEQ ID NO 16
<211> LENGTH: 2487
<212> TYPE: DNA
<213> ORGANISM: Artificial Sequence
<220> FEATURE:
<223> OTHER INFORMATION: DI-2C GFP-172(His)6-DnaE intein -DnaB
      intein-mCherry-Strep Tag)

<400> SEQUENCE: 16

| | | | | | |
|---|---|---|---|---|---|
| ggtaccgtcg | accaaggaga | tataacaatg | agtaaaggag | aagaactttt | cactggagtt | 60 |
| gtcccaattc | ttgttgaatt | agatggtgat | gttaatgggc | acaaattttc | tgtcagtgga | 120 |
| gagggtgaag | gtgatgcaac | atacggaaaa | cttaccctta | aatttatttg | cactactgga | 180 |
| aaactacctg | ttccttggcc | aacacttgtc | actactttca | cttatggtgt | tcaatgcttt | 240 |
| tcaagatacc | cagatcatat | gaagcggcac | gacttcttca | agagcgccat | gcctgaggga | 300 |
| tacgtgcagg | agaggaccat | cttcttcaag | gacgacggga | actacaagac | acgtgctgaa | 360 |
| gtcaagtttg | agggagacac | cctcgtcaac | aggatcgagc | ttaagggaat | cgatttcaag | 420 |
| gaggacggaa | acatcctcgg | ccacaagttg | gaatacaact | acaactccca | caacgtatac | 480 |
| atcatggccg | acaagcaaaa | gaacggcatc | aaagccaact | tcaagacccg | ccacaacatc | 540 |
| gaacaccatc | accatcacca | tgacggcggc | gtgcaactcg | ctgatcatta | tcaacaaaat | 600 |
| actccaattg | gcgatggccc | tgtccttta | ccagacaacc | attacctgtc | cacacaatct | 660 |
| gcccttttcga | aagatcccaa | cgaaaagaga | gaccacatgg | tccttcttga | gtttgtaaca | 720 |
| gctgctggga | ttacacatgg | catggatgaa | ctatacaaac | tcgagtatgc | attgtccttc | 780 |
| ggaactgaga | tacttacagt | tgaatatgga | ccacttccta | ttggaaagat | tgtgagtgaa | 840 |
| gagatcaact | gcagtgttta | ttccgtggat | ccagagggta | gagtttacac | tcaagcaatt | 900 |
| gctcagtggc | atgataggg | agaacaggag | gttcttgaat | atgagttgga | agatggttct | 960 |
| gtgataagag | ctcatcaga | tcacaggttt | cttactacag | attaccaact | tttggcaatc | 1020 |
| gaagagattt | cgctagaca | gctcgatctt | ctcactttgg | aaaatattaa | gcaaacagaa | 1080 |
| gaggcacttg | ataaccatag | gcttccattt | cctctttgg | atgctggaac | tattaagatg | 1140 |
| gttaaagtga | taggaagaag | gtcattgggt | gttcaaagaa | tatttgatat | cggacttcct | 1200 |
| caggatcaca | atttcttact | cgcaaacggt | gctattgctg | cagctggtgg | ttctagagag | 1260 |
| tctggagcta | tctctggcga | tagtctgatc | agcctggcta | gcacaggaaa | aagagtttct | 1320 |
| attaaagatt | tgttagatga | aaagatttt | gaaatatggg | caattaatga | acagacgatg | 1380 |
| aagctagaat | cagctaaagt | tagtcgtgta | ttttgtactg | gcaaaaagct | agtttatatt | 1440 |
| ctaaaaactc | gactaggtag | aactatcaag | gcaacagcaa | atcatagatt | tttaactatt | 1500 |
| gatggttgga | aaagattaga | tgagctatct | ttaaagagc | atattgctct | accccgtaaa | 1560 |
| ctagaaagct | cctcttttaca | attgtcacca | gaaatagaaa | agttgtctca | gagtgatatt | 1620 |
| tactgggact | ccatcgtttc | tattacgag | actggagtcg | aagaggtttt | tgatttgact | 1680 |
| gtgccaggac | cacataactt | tgtcgcgaat | gacatcattg | tacacaacag | ccgcgggccc | 1740 |

-continued

```
gtgagcaagg gcgaggagga taacatggcc atcatcaagg agttcatgcg cttcaaggtg      1800
cacatggagg gctccgtgaa cggccacgag ttcgagatcg agggcgaggg cgagggccgc      1860
ccctacgagg gcacccagac cgccaagctg aaggtgacca agggtggccc cctgcccttc      1920
gcctgggaca tcctgtcccc tcagttcatg tacggctcca aggcctacgt gaagcacccc      1980
gccgacatcc ccgactactt gaagctgtcc ttccccgagg gcttcaagtg ggagcgcgtg      2040
atgaacttcg aggacggcgg cgtggtgacc gtgacccagg actcctccct gcaggacggc      2100
gagttcatct acaaggtgaa gctgcgcggc accaacttcc cctccgacgg ccccgtaatg      2160
cagaagaaga ccatgggctg ggaggcctcc tccgagcgga tgtacccga ggacggcgcc       2220 ctgaagggcg agatcaagca gaggctgaag ctgaaggacg gcggccacta cgacgctgag      2280
gtcaagacca cctacaaggc caagaagccc gtgcagctgc ccggcgccta caacgtcaac      2340
atcaagttgg acatcacctc ccacaacgag gactacacca tcgtggaaca gtacgaacgc     2400
gccgagggcc gccactccac cggcggcatg gacgagctgt acaagggttc tggatggtca     2460
catcctcagt ttgaaaaatg agagctc                                          2487
```

<210> SEQ ID NO 17
<211> LENGTH: 817
<212> TYPE: PRT
<213> ORGANISM: Artificial Sequence
<220> FEATURE:
<223> OTHER INFORMATION: DI-2C GFP-172(His)6-DnaE intein -DnaB intein-mCherry-Strep Tag)

<400> SEQUENCE: 17

```
Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
    210                 215                 220
```

-continued

```
Val Leu Leu Glu Phe Val Thr Ala Ala Gly Ile Thr His Gly Met Asp
225                 230                 235                 240

Glu Leu Tyr Lys Leu Glu Tyr Ala Leu Ser Phe Gly Thr Glu Ile Leu
            245                 250                 255

Thr Val Glu Tyr Gly Pro Leu Pro Ile Gly Lys Ile Val Ser Glu Glu
        260                 265                 270

Ile Asn Cys Ser Val Tyr Ser Val Asp Pro Glu Gly Arg Val Tyr Thr
    275                 280                 285

Gln Ala Ile Ala Gln Trp His Asp Arg Gly Glu Gln Val Leu Glu
290                 295                 300

Tyr Glu Leu Glu Asp Gly Ser Val Ile Arg Ala Thr Ser Asp His Arg
305                 310                 315                 320

Phe Leu Thr Thr Asp Tyr Gln Leu Leu Ala Ile Glu Glu Ile Phe Ala
                325                 330                 335

Arg Gln Leu Asp Leu Leu Thr Leu Glu Asn Ile Lys Gln Thr Glu Glu
            340                 345                 350

Ala Leu Asp Asn His Arg Leu Pro Phe Pro Leu Leu Asp Ala Gly Thr
        355                 360                 365

Ile Lys Met Val Lys Val Ile Gly Arg Arg Ser Leu Gly Val Gln Arg
    370                 375                 380

Ile Phe Asp Ile Gly Leu Pro Gln Asp His Asn Phe Leu Leu Ala Asn
385                 390                 395                 400

Gly Ala Ile Ala Ala Ala Gly Gly Ser Arg Glu Ser Gly Ala Ile Ser
                405                 410                 415

Gly Asp Ser Leu Ile Ser Leu Ala Ser Thr Gly Lys Arg Val Ser Ile
            420                 425                 430

Lys Asp Leu Leu Asp Glu Lys Asp Phe Glu Ile Trp Ala Ile Asn Glu
        435                 440                 445

Gln Thr Met Lys Leu Glu Ser Ala Lys Val Ser Arg Val Phe Cys Thr
    450                 455                 460

Gly Lys Lys Leu Val Tyr Ile Leu Lys Thr Arg Leu Gly Arg Thr Ile
465                 470                 475                 480

Lys Ala Thr Ala Asn His Arg Phe Leu Thr Ile Asp Gly Trp Lys Arg
                485                 490                 495

Leu Asp Glu Leu Ser Leu Lys Glu His Ile Ala Leu Pro Arg Lys Leu
            500                 505                 510

Glu Ser Ser Ser Leu Gln Leu Ser Pro Glu Ile Glu Lys Leu Ser Gln
        515                 520                 525

Ser Asp Ile Tyr Trp Asp Ser Ile Val Ser Ile Thr Glu Thr Gly Val
    530                 535                 540

Glu Glu Val Phe Asp Leu Thr Val Pro Gly Pro His Asn Phe Val Ala
545                 550                 555                 560

Asn Asp Ile Ile Val His Asn Ser Arg Gly Pro Val Ser Lys Gly Glu
                565                 570                 575

Glu Asp Asn Met Ala Ile Ile Lys Glu Phe Met Arg Phe Lys Val His
            580                 585                 590

Met Glu Gly Ser Val Asn Gly His Glu Phe Glu Ile Glu Gly Glu Gly
        595                 600                 605

Glu Gly Arg Pro Tyr Glu Gly Thr Gln Thr Ala Lys Leu Lys Val Thr
    610                 615                 620

Lys Gly Gly Pro Leu Pro Phe Ala Trp Asp Ile Leu Ser Pro Gln Phe
625                 630                 635                 640

Met Tyr Gly Ser Lys Ala Tyr Val Lys His Pro Ala Asp Ile Pro Asp
```

|   |   |   | 645 |   |   |   | 650 |   |   |   | 655 |   |
|---|---|---|---|---|---|---|---|---|---|---|---|---|
| Tyr | Leu | Lys | Leu | Ser | Phe | Pro | Glu | Gly | Phe | Lys | Trp | Glu | Arg | Val | Met |
|   |   |   | 660 |   |   |   | 665 |   |   |   | 670 |   |

Asn Phe Glu Asp Gly Gly Val Val Thr Val Thr Gln Asp Ser Ser Leu
            675                 680                 685

Gln Asp Gly Glu Phe Ile Tyr Lys Val Lys Leu Arg Gly Thr Asn Phe
        690                 695                 700

Pro Ser Asp Gly Pro Val Met Gln Lys Lys Thr Met Gly Trp Glu Ala
705                 710                 715                 720

Ser Ser Glu Arg Met Tyr Pro Glu Asp Gly Ala Leu Lys Gly Glu Ile
                725                 730                 735

Lys Gln Arg Leu Lys Leu Lys Asp Gly Gly His Tyr Asp Ala Glu Val
            740                 745                 750

Lys Thr Thr Tyr Lys Ala Lys Lys Pro Val Gln Leu Pro Gly Ala Tyr
        755                 760                 765

Asn Val Asn Ile Lys Leu Asp Ile Thr Ser His Asn Glu Asp Tyr Thr
770                 775                 780

Ile Val Glu Gln Tyr Glu Arg Ala Glu Gly Arg His Ser Thr Gly Gly
785                 790                 795                 800

Met Asp Glu Leu Tyr Lys Gly Ser Gly Trp Ser His Pro Gln Phe Glu
                805                 810                 815

Lys

<210> SEQ ID NO 18
<211> LENGTH: 2268
<212> TYPE: DNA
<213> ORGANISM: Artificial Sequence
<220> FEATURE:
<223> OTHER INFORMATION: Intein 70: (pE1775-SP-mGFP172-DnaE Intein-2A
      ver.3-mCherry-streptag)

<400> SEQUENCE: 18

```
gtcgaccaag gagatataac aatgaagact aatcttttc tctttctcat ctttttcactt        60 ctcctatcat tatcctcggc cgaattcagt aaaggagaag aacttttcac tggagttgtc       120
ccaattcttg ttgaattaga tggtgatgtt aatgggcaca attttctgt cagtggagag       180 ggtgaaggtg atgcaacata cggaaaactt acccttaaat ttatttgcac tactggaaaa       240
ctacctgttc cttggccaac acttgtcact actttcactt atggtgttca atgcttttca       300 agataccag atcatatgaa gcggcacgac ttcttcaaga gcgccatgcc tgagggatac       360
gtgcaggaga ggaccatctt cttcaaggac gacgggaact acaagacacg tgctgaagtc       420
aagtttgagg gagacaccct cgtcaacagg atcgagctta agggaatcga tttcaaggag       480
gacggaaaca tcctcggcca aagttggaa tacaactaca actcccacaa cgtatacatc       540
atggccgaca gcaaaagaa cggcatcaaa gccaacttca gacccgcca acatcgaa          600 caccatcacc atcaccatga cggcggcgtg caactcgctg atcattatca acaaaatact       660
ccaattggcg atggccctgt cctttacca gacaaccatt acctgtccac acaatctgcc       720
ctttcgaaag atcccaacga aaagagagac cacatggtcc ttcttgagtt tgtaacagct       780
gctgggatta cacatggcat ggatgaacta tacaaactcg agggaggatc taagtttgca       840
aatgattgtt tgtccttcgg aactgagata cttacagttg aatatggacc acttcctatt       900
ggaaagattg tgagtgaaga gatcaactgc agtgttatt ccgtggatcc agagggtaga       960
gtttacactc aagcaattgc tcagtggcat gatagggag aacaggaggt tcttgaatat      1020
```

```
gagttggaag atggttctgt gataagagct acatcagatc acaggtttct tactacagat    1080
taccaacttt tggcaatcga agagattttc gctagacagc tcgatcttct cactttggaa    1140
aatattaagc aaacagaaga ggcacttgat aaccataggc ttccatttcc tcttttggat    1200
gctggaacta ttaagatggt taaagtgata ggaagaaggt cattgggtgt caaagaata    1260 tttgatatcg gacttcctca ggatcacaat ttcttactcg caaacggtgc tattgctgca    1320
gcttgtttca atggttctgg ttctagagtt actgagcttt tgtataggat gaagagggca    1380
gaaacatact gcccaagacc tttactcgca atccatccaa cagaggctag cacaagcaa    1440 aaaattgttg ctcctgtgaa acagcttttg aactttgatc ttctcaagct tgcgggagac    1500
gtcgagtcca accctgggcc cgtgagcaag ggcgaggag ataacatggc catcatcaag    1560
gagttcatgc gcttcaaggt gcacatggag ggctccgtga acggccacga gttcgagatc    1620
gagggcgagg gcgagggccg cccctacgag ggcacccaga ccgccaagct gaaggtgacc    1680
aagggtggcc ccctgccctt cgcctgggac atcctgtccc ctcagttcat gtacggctcc    1740
aaggcctacg tgaagcaccc cgccgacatc cccgactact gaagctgtc cttccccgag    1800 ggcttcaagt gggagcgcgt gatgaacttc gaggacggcg gcgtggtgac cgtgaccaag    1860
accatgggct gggaggcctc ctccgagcgg atgtaccccg aggacggcgc cctgaagggc    1920
gagatcaagc agaggctgaa gctgaagcag actcctcccc tgcaggacgg cgagttcatc    1980
tacaaggtga agctgcgcgg caccaacttc ccctccgacg gccccgtaat gcagaaggac    2040
ggcggccact acgacgctga ggtcaagacc acctacaagg ccaagaagcc cgtgcagctg    2100
cccggcgcct acaacgtcaa catcaagttg gacatcacct cccacaacga ggactacacc    2160
atcgtggaac agtacgaacg cgccgagggc cgccactcca ccggcggcat ggacgagctg    2220
tacaagggtt ctggatggtc acatcctcag tttgaaaaat gagagctc                2268
```

<210> SEQ ID NO 19
<211> LENGTH: 746
<212> TYPE: PRT
<213> ORGANISM: Artificial Sequence
<220> FEATURE:
<223> OTHER INFORMATION: Intein 70: (pE1775-SP-mGFP172-DnaE Intein-2A ver.3-mCherry-streptag)

<400> SEQUENCE: 19

```
Met Lys Thr Asn Leu Phe Leu Phe Leu Ile Phe Ser Leu Leu Leu Ser
 1               5                  10                  15

Leu Ser Ser Ala Glu Phe Ser Lys Gly Glu Glu Leu Phe Thr Gly Val
                20                  25                  30

Val Pro Ile Leu Val Glu Leu Asp Gly Asp Val Asn Gly His Lys Phe
            35                  40                  45

Ser Val Ser Gly Glu Gly Glu Gly Asp Ala Thr Tyr Gly Lys Leu Thr
        50                  55                  60

Leu Lys Phe Ile Cys Thr Thr Gly Lys Leu Pro Val Pro Trp Pro Thr
65                  70                  75                  80

Leu Val Thr Thr Phe Thr Tyr Gly Val Gln Cys Phe Ser Arg Tyr Pro
                85                  90                  95

Asp His Met Lys Arg His Asp Phe Phe Lys Ser Ala Met Pro Glu Gly
                100                 105                 110

Tyr Val Gln Glu Arg Thr Ile Phe Phe Lys Asp Asp Gly Asn Tyr Lys
            115                 120                 125

Thr Arg Ala Glu Val Lys Phe Glu Gly Asp Thr Leu Val Asn Arg Ile
        130                 135                 140
```

```
Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Ala Asn Phe Lys Thr Arg His Asn Ile
            180                 185                 190

Glu His His His His His Asp Gly Gly Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr His Gly Met Asp Glu Leu Tyr Lys Leu Glu Gly Gly Ser Lys Phe
                260                 265                 270

Ala Asn Asp Cys Leu Ser Phe Gly Thr Glu Ile Leu Thr Val Glu Tyr
            275                 280                 285

Gly Pro Leu Pro Ile Gly Lys Ile Val Ser Glu Glu Ile Asn Cys Ser
290                 295                 300

Val Tyr Ser Val Asp Pro Glu Gly Arg Val Tyr Thr Gln Ala Ile Ala
305                 310                 315                 320

Gln Trp His Asp Arg Gly Glu Gln Glu Val Leu Glu Tyr Glu Leu Glu
                325                 330                 335

Asp Gly Ser Val Ile Arg Ala Thr Ser Asp His Arg Phe Leu Thr Thr
                340                 345                 350

Asp Tyr Gln Leu Leu Ala Ile Glu Ile Phe Ala Arg Gln Leu Asp
    355                 360                 365

Leu Leu Thr Leu Glu Asn Ile Lys Gln Thr Glu Glu Ala Leu Asp Asn
    370                 375                 380

His Arg Leu Pro Phe Pro Leu Leu Asp Ala Gly Thr Ile Lys Met Val
385                 390                 395                 400

Lys Val Ile Gly Arg Arg Ser Leu Gly Val Gln Arg Ile Phe Asp Ile
                405                 410                 415

Gly Leu Pro Gln Asp His Asn Phe Leu Leu Ala Asn Gly Ala Ile Ala
            420                 425                 430

Ala Ala Cys Phe Asn Gly Ser Gly Ser Arg Val Thr Glu Leu Leu Tyr
        435                 440                 445

Arg Met Lys Arg Ala Glu Thr Tyr Cys Pro Arg Pro Leu Leu Ala Ile
    450                 455                 460

His Pro Thr Glu Ala Arg His Lys Gln Lys Ile Val Ala Pro Val Lys
465                 470                 475                 480

Gln Leu Leu Asn Phe Asp Leu Leu Lys Leu Ala Gly Asp Val Glu Ser
                485                 490                 495

Asn Pro Gly Pro Val Ser Lys Gly Glu Glu Asp Asn Met Ala Ile Ile
            500                 505                 510

Lys Glu Phe Met Arg Phe Lys Val His Met Glu Gly Ser Val Asn Gly
                515                 520                 525

His Glu Phe Glu Ile Glu Gly Glu Gly Glu Gly Arg Pro Tyr Glu Gly
        530                 535                 540

Thr Gln Thr Ala Lys Leu Lys Val Thr Lys Gly Gly Pro Leu Pro Phe
545                 550                 555                 560
```

```
Ala Trp Asp Ile Leu Ser Pro Gln Phe Met Tyr Gly Ser Lys Ala Tyr
            565                 570                 575

Val Lys His Pro Ala Asp Ile Pro Asp Tyr Leu Lys Leu Ser Phe Pro
        580                 585                 590

Glu Gly Phe Lys Trp Glu Arg Val Met Asn Phe Glu Asp Gly Gly Val
            595                 600                 605

Val Thr Val Thr Lys Thr Met Gly Trp Glu Ala Ser Ser Glu Arg Met
    610                 615                 620

Tyr Pro Glu Asp Gly Ala Leu Lys Gly Glu Ile Lys Gln Arg Leu Lys
625                 630                 635                 640

Leu Lys Gln Asp Ser Ser Leu Gln Asp Gly Glu Phe Ile Tyr Lys Val
                645                 650                 655

Lys Leu Arg Gly Thr Asn Phe Pro Ser Asp Gly Pro Val Met Gln Lys
            660                 665                 670

Asp Gly Gly His Tyr Asp Ala Glu Val Lys Thr Thr Tyr Lys Ala Lys
        675                 680                 685

Lys Pro Val Gln Leu Pro Gly Ala Tyr Asn Val Asn Ile Lys Leu Asp
    690                 695                 700

Ile Thr Ser His Asn Glu Asp Tyr Thr Ile Val Glu Gln Tyr Glu Arg
705                 710                 715                 720

Ala Glu Gly Arg His Ser Thr Gly Gly Met Asp Glu Leu Tyr Lys Gly
                725                 730                 735

Ser Gly Trp Ser His Pro Gln Phe Glu Lys
            740                 745

<210> SEQ ID NO 20
<211> LENGTH: 2319
<212> TYPE: DNA
<213> ORGANISM: Artificial Sequence
<220> FEATURE:
<223> OTHER INFORMATION: Intein-2A-UBQ-1 (GFP172-DnaE intein w/o
      overhang-sea urchin 2A-Arabidopsis
      UBQ11-mCherry-streptag)

<400> SEQUENCE: 20
ggtaccgtcg accaaggaga tataacaatg agtaaaggag aagaactttt cactggagtt      60
gtcccaattc ttgttgaatt agatggtgat gttaatgggc acaaattttc tgtcagtgga     120
gagggtgaag gtgatgcaac atacggaaaa cttacccttaa aatttatttg cactactgga    180
aaactacctg ttccttggcc aacacttgtc actactttca cttatggtgt tcaatgcttt     240
tcaagatacc cagatcatat gaagcggcac gacttcttca gagcgccat gcctgaggga     300 tacgtgcagg agaggaccat cttcttcaag gacgacggga actacaagac acgtgctgaa    360
gtcaagtttg agggagacac cctcgtcaac aggatcgagc ttaagggaat cgatttcaag    420
gaggacggaa acatcctcgg ccacaagttg gaatacaact acaactccca caacgtatac    480
atcatggccg acaagcaaaa gaacggcatc aaagccaact tcaagacccg ccacaacatc    540
gaacaccatc accatcacca tgacggcggc gtgcaactcg ctgatcatta tcaacaaaat    600
actccaattg gcgatggccc tgtcctttta ccagacaacc attacctgtc cacacaatct    660
gccctttcga aagatcccaa cgaaaagaga gaccacatgg tccttcttga gtttgtaaca    720
gctgctggga ttacacatgg catggatgaa ctatacaaat gtttgtcctt cggaactgag    780
atacttacag ttgaatatgg accacttcct attggaaaga ttgtgagtga agagatcaac    840
tgcagtgttt attccgtgga tccagagggt agagtttaca ctcaagcaat tgctcagtgg    900
catgataggg gagaacagga ggttcttgaa tatgagttgg aagatggttc tgtgataaga    960
```

```
gctacatcag atcacaggtt tcttactaca gattaccaac ttttggcaat cgaagagatt    1020
ttcgctagac agctcgatct tctcactttg gaaaatatta agcaaacaga agaggcactt    1080
gataaccata ggcttccatt tcctcttttg gatgctggaa ctattaagat ggttaaagtg    1140
ataggaagaa ggtcattggg tgttcaaaga atatttgata tcggacttcc tcaggatcac    1200
aatttcttac tcgcaaacgg tgctattgct gcagcttgtt cttgtggttc tggttctaga    1260
ggatctggcg atggattctg cattctctat ctgctcctga tcctcttgat gaggtctggt    1320
gacgttgaaa ccaaccctgg gcccatgcag atcttcgtaa agactttgac cggaaagacc    1380
atcactcttg aagttgaaag ctccgacacc attgataacg tgaaggctaa gatccaggac    1440
aaggaaggca ttcctccgga ccagcagcgt ctcatcttcg ctggaaggca gcttgaggat    1500
ggacgtactt tggccgacta caacatccag aaggagtcca ctcttcactt ggtcctccgt    1560
ctccgcggcg gtgtgagcaa gggcgaggag ataacatgg ccatcatcaa ggagttcatg    1620
cgcttcaagg tgcacatgga gggctccgtg aacggccacg agttcgagat cgagggcgag    1680
ggcgagggcc gcccctacga gggcacccag accgccaagc tgaaggtgac caagggtggc    1740
cccctgccct cgcctgggga catcctgtcc cctcagttca gtacggctc caaggcctac    1800 gtgaagcacc ccgccgacat ccccgactac ttgaagctgt ccttccccga gggcttcaag    1860
tgggagcgcg tgatgaactt cgaggacggc ggcgtggtga ccgtgaccca ggactcctcc    1920
ctgcaggacg gcgagttcat ctacaaggtg aagctgcgcg caccaacctt ccctccgac    1980 ggccccgtaa tgcagaagaa gaccatgggc tgggaggcct cctccgagcg gatgtacccc    2040
gaggacggcg ccctgaaggg cgagatcaag cagaggctga agctgaagga cggcggccac    2100
tacgacgctg aggtcaagac cacctacaag gccaagaagc ccgtgcagct gcccggcgcc    2160
tacaacgtca acatcaagtt ggacatcacc tcccacaacg aggactacac catcgtggaa    2220
cagtacgaac gcgccgaggg ccgccactcc accggcggca tggacgagct gtacaagggt    2280
tctggatggt cacatcctca gtttgaaaaa tgagagctc                          2319
```

<210> SEQ ID NO 21
<211> LENGTH: 761
<212> TYPE: PRT
<213> ORGANISM: Artificial Sequence
<220> FEATURE:
<223> OTHER INFORMATION: Intein-2A-UBQ-1 (GFP172-DnaE intein w/o
      overhang-sea urchin 2A-Arabidopsis
      UBQ11-mCherry-streptag)

<400> SEQUENCE: 21

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
            195                 200                 205

Thr Gln Ser Ala Leu Ser Lys Asp Pro Asn Glu Lys Arg Asp His Met
            210                 215                 220

Val Leu Leu Glu Phe Val Thr Ala Ala Gly Ile Thr His Gly Met Asp
225                 230                 235                 240

Glu Leu Tyr Lys Cys Leu Ser Phe Gly Thr Glu Ile Leu Thr Val Glu
                245                 250                 255

Tyr Gly Pro Leu Pro Ile Gly Lys Ile Val Ser Glu Glu Ile Asn Cys
            260                 265                 270

Ser Val Tyr Ser Val Asp Pro Glu Gly Arg Val Tyr Thr Gln Ala Ile
        275                 280                 285

Ala Gln Trp His Asp Arg Gly Glu Gln Glu Val Leu Glu Tyr Glu Leu
        290                 295                 300

Glu Asp Gly Ser Val Ile Arg Ala Thr Ser Asp His Arg Phe Leu Thr
305                 310                 315                 320

Thr Asp Tyr Gln Leu Leu Ala Ile Glu Ile Phe Ala Arg Gln Leu
                325                 330                 335

Asp Leu Leu Thr Leu Glu Asn Ile Lys Gln Thr Glu Glu Ala Leu Asp
            340                 345                 350

Asn His Arg Leu Pro Phe Pro Leu Leu Asp Ala Gly Thr Ile Lys Met
        355                 360                 365

Val Lys Val Ile Gly Arg Arg Ser Leu Gly Val Gln Arg Ile Phe Asp
        370                 375                 380

Ile Gly Leu Pro Gln Asp His Asn Phe Leu Leu Ala Asn Gly Ala Ile
385                 390                 395                 400

Ala Ala Ala Cys Ser Cys Gly Ser Gly Ser Arg Gly Ser Gly Asp Gly
                405                 410                 415

Phe Cys Ile Leu Tyr Leu Leu Leu Ile Leu Leu Met Arg Ser Gly Asp
            420                 425                 430

Val Glu Thr Asn Pro Gly Pro Met Gln Ile Phe Val Lys Thr Leu Thr
        435                 440                 445

Gly Lys Thr Ile Thr Leu Glu Val Glu Ser Ser Asp Thr Ile Asp Asn
    450                 455                 460

Val Lys Ala Lys Ile Gln Asp Lys Glu Gly Ile Pro Pro Asp Gln Gln
465                 470                 475                 480

Arg Leu Ile Phe Ala Gly Arg Gln Leu Glu Asp Gly Arg Thr Leu Ala
            485                 490                 495

Asp Tyr Asn Ile Gln Lys Glu Ser Thr Leu His Leu Val Leu Arg Leu
            500                 505                 510

Arg Gly Gly Val Ser Lys Gly Glu Glu Asp Asn Met Ala Ile Ile Lys
        515                 520                 525
```

```
Glu Phe Met Arg Phe Lys Val His Met Glu Gly Ser Val Asn Gly His
            530                 535                 540
Glu Phe Glu Ile Glu Gly Gly Glu Gly Arg Pro Tyr Glu Gly Thr
545                 550                 555                 560
Gln Thr Ala Lys Leu Lys Val Thr Lys Gly Gly Pro Leu Pro Phe Ala
                565                 570                 575
Trp Asp Ile Leu Ser Pro Gln Phe Met Tyr Gly Ser Lys Ala Tyr Val
            580                 585                 590
Lys His Pro Ala Asp Ile Pro Asp Tyr Leu Lys Leu Ser Phe Pro Glu
        595                 600                 605
Gly Phe Lys Trp Glu Arg Val Met Asn Phe Glu Asp Gly Gly Val Val
    610                 615                 620
Thr Val Thr Gln Asp Ser Ser Leu Gln Asp Gly Glu Phe Ile Tyr Lys
625                 630                 635                 640
Val Lys Leu Arg Gly Thr Asn Phe Pro Ser Asp Gly Pro Val Met Gln
                645                 650                 655
Lys Lys Thr Met Gly Trp Glu Ala Ser Ser Glu Arg Met Tyr Pro Glu
            660                 665                 670
Asp Gly Ala Leu Lys Gly Glu Ile Lys Gln Arg Leu Lys Leu Lys Asp
        675                 680                 685
Gly Gly His Tyr Asp Ala Glu Val Lys Thr Thr Tyr Lys Ala Lys Lys
    690                 695                 700
Pro Val Gln Leu Pro Gly Ala Tyr Asn Val Asn Ile Lys Leu Asp Ile
705                 710                 715                 720
Thr Ser His Asn Glu Asp Tyr Thr Ile Val Glu Gln Tyr Glu Arg Ala
                725                 730                 735
Glu Gly Arg His Ser Thr Gly Gly Met Asp Glu Leu Tyr Lys Gly Ser
            740                 745                 750
Gly Trp Ser His Pro Gln Phe Glu Lys
        755                 760

<210> SEQ ID NO 22
<211> LENGTH: 4
<212> TYPE: PRT
<213> ORGANISM: Artificial Sequence
<220> FEATURE:
<223> OTHER INFORMATION: Furin target site
<220> FEATURE:
<221> NAME/KEY: VARIANT
<222> LOCATION: (2)...(3)
<223> OTHER INFORMATION: Xaa = any amino acid

<400> SEQUENCE: 22

Arg Xaa Xaa Arg
 1

<210> SEQ ID NO 23
<211> LENGTH: 4
<212> TYPE: PRT
<213> ORGANISM: Artificial Sequence
<220> FEATURE:
<223> OTHER INFORMATION: Furin target site
<220> FEATURE:
<221> NAME/KEY: VARIANT
<222> LOCATION: 2
<223> OTHER INFORMATION: Xaa = any amino acid residue
<220> FEATURE:
<221> NAME/KEY: VARIANT
<222> LOCATION: 3
<223> OTHER INFORMATION: Xaa = Lys or Arg

<400> SEQUENCE: 23
```

Arg Xaa Xaa Arg
 1

<210> SEQ ID NO 24
<211> LENGTH: 97
<212> TYPE: PRT
<213> ORGANISM: Homo sapiens

<400> SEQUENCE: 24

Glu Ala Lys Pro Ser Thr Glu Asp Leu Gly Asp Lys Lys Glu Gly Glu
 1               5                  10                  15

Tyr Ile Lys Leu Lys Val Ile Gly Gln Asp Ser Ser Glu Ile His Phe
            20                  25                  30

Lys Val Lys Met Thr Thr His Leu Lys Lys Leu Lys Glu Ser Tyr Cys
        35                  40                  45

Gln Arg Gln Gly Val Pro Met Asn Ser Leu Arg Phe Leu Phe Glu Gly
    50                  55                  60

Gln Arg Ile Ala Asp Asn His Thr Pro Lys Glu Leu Gly Met Glu Glu
65                  70                  75                  80

Glu Asp Val Ile Glu Val Tyr Gln Glu Gln Thr Gly Gly His Ser Thr
                85                  90                  95

Val

<210> SEQ ID NO 25
<211> LENGTH: 303
<212> TYPE: DNA
<213> ORGANISM: Homo sapiens

<400> SEQUENCE: 25
atgtctgacc aggaggcaaa accttcaact gaggacttgg gggataagaa ggaaggtgaa      60
tatattaaac tcaaagtcat tggacaggat agcagtgaga ttcacttcaa agtgaaaatg     120
acaacacatc tcaagaaact caaagaatca tactgtcaaa gacagggtgt tccaatgaat     180
tcactcaggt ttctctttga gggtcagaga attgctgata atcatactcc aaaagaactg     240
ggaatggagg aagaagatgt gattgaagtt tatcaggaac aaacgggggg tcattcaaca     300
gtt                                                                   303

<210> SEQ ID NO 26
<211> LENGTH: 2304
<212> TYPE: DNA
<213> ORGANISM: Artificial Sequence
<220> FEATURE:
<223> OTHER INFORMATION: Ssp DnaE intein-2A-SUMO

<400> SEQUENCE: 26
ggtaccgtcg accaaggaga tataacaatg agtaaaggag aagaacttttt cactggagtt      60 gtcccaattc ttgttgaatt agatggtgat gttaatgggc acaaattttc tgtcagtgga     120
gagggtgaag gtgatgcaac atacggaaaa cttacccctta aatttatttg cactactgga     180
aaactacctg ttccttggcc aacacttgtc actactttca cttatggtgt tcaatgcttt     240
tcaagatacc cagatcatat gaagcggcac gacttcttca agagcgccat gcctgaggga     300
tacgtgcagg agaggaccat cttcttcaag gacgacggga actacaagac acgtgctgaa     360
gtcaagtttg agggagacac cctcgtcaac aggatcgagc ttaagggaat cgatttcaag     420
gaggacggaa acatcctcgg ccacaagttg gaatacaact acaactccca caacgtatac     480
atcatggccg acaagcaaaa gaacggcatc aaagccaact tcaagacccg ccacaacatc     540

```
gaacaccatc accatcacca tgacggcggc gtgcaactcg ctgatcatta tcaacaaaat    600
actccaattg gcgatggccc tgtccttta ccagacaacc attacctgtc cacacaatct    660 gcccttcga agatcccaa cgaaaagaga gaccacatgg tccttcttga gtttgtaaca    720
gctgctggga ttacacatgg catggatgaa ctatacaaat gtttgtcctt cggaactgag    780
atacttacag ttgaatatgg accacttcct attggaaaga ttgtgagtga agagatcaac    840
tgcagtgttt attccgtgga tccagagggt agagtttaca ctcaagcaat tgctcagtgg    900
catgataggg gagaacagga ggttcttgaa tatgagttgg aagatggttc tgtgataaga    960
gctacatcag atcacaggtt tcttactaca gattaccaac ttttggcaat cgaagagatt   1020
ttcgctagac agctcgatct tctcactttg gaaaatatta gcaaacaga agaggcactt   1080 gataaccata ggcttccatt tcctcttttg gatgctggaa ctattaagat ggttaaagtg   1140
ataggaagaa ggtcattggg tgttcaaaga atatttgata tcggacttcc tcaggatcac   1200
aatttcttac tcgcaaacgg tgctattgct gcagcttgtt cttgtggttc tggtatgtct   1260
gaccaggagg caaaaccttc aactgaggac ttggggata agaaggaagg tgaatatatt   1320
aaactcaaag tcattggaca ggatagcagt gagattcact tcaaagtgaa aatgacaaca   1380
catctcaaga aactcaaaga atcatactgt caaagacagg gtgttccaat gaattcactc   1440
aggtttctct ttgagggtca gagaattgct gataatcata ctccaaaaga actgggaatg   1500
gaggaagaag atgtgattga agtttatcag gaacaaacgg ggggtcattc aacagttgtg   1560
agcaagggcg aggaggataa catggccatc atcaaggagt tcatgcgctt caaggtgcac   1620
atggagggct ccgtgaacgg ccacgagttc gagatcgagg gcgagggcga gggccgcccc   1680
tacgagggca cccagaccgc caagctgaag gtgaccaagg gtggccccct gcccttcgcc   1740
tgggacatcc tgtcccctca gttcatgtac ggctccaagg cctacgtgaa gcaccccgcc   1800
gacatccccg actacttgaa gctgtccttc cccgagggct tcaagtggga gcgcgtgatg   1860
aacttcgagg acggcggcgt ggtgaccgtg acccaggact cctccctgca ggacggcgag   1920
ttcatctaca aggtgaagct gcgcggcacc aacttcccct ccgacggccc cgtaatgcag   1980
aagaagacca tgggctggga ggcctcctcc gagcggatgt accccgagga cggcgccctg   2040
aagggcgaga tcaagcagag gctgaagctg aaggacggcg gccactacga cgctgaggtc   2100
aagaccacct acaaggccaa gaagcccgtg cagctgcccg gcgcctacaa cgtcaacatc   2160
aagttggaca tcacctccca caacgaggac tacaccatcg tggaacagta cgaacgcgcc   2220
gagggccgcc actccaccgg cggcatggac gagctgtaca agggtctgg atggtcacat   2280 cctcagtttg aaaaatgaga gctc                                         2304
```

<210> SEQ ID NO 27
<211> LENGTH: 756
<212> TYPE: PRT
<213> ORGANISM: Artificial Sequence
<220> FEATURE:
<223> OTHER INFORMATION: Ssp DnaE intein-2A-SUMO

<400> SEQUENCE: 27

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

```
Thr Thr Gly Lys Leu Pro Val Pro Trp Pro Thr Leu Val Thr Thr Phe
 50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu His His His His
                165                 170                 175

His His Asp Gly Gly Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Ala Leu Ser Lys Asp Pro Asn Glu Lys Arg Asp His Met
210                 215                 220

Val Leu Leu Glu Phe Val Thr Ala Ala Gly Ile Thr His Gly Met Asp
225                 230                 235                 240

Glu Leu Tyr Lys Cys Leu Ser Phe Gly Thr Glu Ile Leu Thr Val Glu
                245                 250                 255

Tyr Gly Pro Leu Pro Ile Gly Lys Ile Val Ser Glu Glu Ile Asn Cys
            260                 265                 270

Ser Val Tyr Ser Val Asp Pro Glu Gly Arg Val Tyr Thr Gln Ala Ile
        275                 280                 285

Ala Gln Trp His Asp Arg Gly Glu Gln Glu Val Leu Glu Tyr Glu Leu
290                 295                 300

Glu Asp Gly Ser Val Ile Arg Ala Thr Ser Asp His Arg Phe Leu Thr
305                 310                 315                 320

Thr Asp Tyr Gln Leu Leu Ala Ile Glu Glu Ile Phe Ala Arg Gln Leu
                325                 330                 335

Asp Leu Leu Thr Leu Glu Asn Ile Lys Gln Thr Glu Glu Ala Leu Asp
            340                 345                 350

Asn His Arg Leu Pro Phe Pro Leu Leu Asp Ala Gly Thr Ile Lys Met
        355                 360                 365

Val Lys Val Ile Gly Arg Arg Ser Leu Gly Val Gln Arg Ile Phe Asp
370                 375                 380

Ile Gly Leu Pro Gln Asp His Asn Phe Leu Leu Ala Asn Gly Ala Ile
385                 390                 395                 400

Ala Ala Ala Cys Ser Cys Gly Ser Gly Met Ser Asp Gln Glu Ala Lys
                405                 410                 415

Pro Ser Thr Glu Asp Leu Gly Asp Lys Lys Glu Gly Glu Tyr Ile Lys
            420                 425                 430

Leu Lys Val Ile Gly Gln Asp Ser Ser Glu Ile His Phe Lys Val Lys
        435                 440                 445

Met Thr Thr His Leu Lys Lys Leu Lys Glu Ser Tyr Cys Gln Arg Gln
450                 455                 460
```

Gly Val Pro Met Asn Ser Leu Arg Phe Leu Phe Glu Gly Gln Arg Ile
465                 470                 475                 480

Ala Asp Asn His Thr Pro Lys Glu Leu Gly Met Glu Glu Glu Asp Val
                485                 490                 495

Ile Glu Val Tyr Gln Glu Gln Thr Gly Gly His Ser Thr Val Val Ser
            500                 505                 510

Lys Gly Glu Glu Asp Asn Met Ala Ile Ile Lys Glu Phe Met Arg Phe
        515                 520                 525

Lys Val His Met Glu Gly Ser Val Asn Gly His Glu Phe Glu Ile Glu
    530                 535                 540

Gly Glu Gly Glu Gly Arg Pro Tyr Glu Gly Thr Gln Thr Ala Lys Leu
545                 550                 555                 560

Lys Val Thr Lys Gly Gly Pro Leu Pro Phe Ala Trp Asp Ile Leu Ser
                565                 570                 575

Pro Gln Phe Met Tyr Gly Ser Lys Ala Tyr Val Lys His Pro Ala Asp
                580                 585                 590

Ile Pro Asp Tyr Leu Lys Leu Ser Phe Pro Glu Gly Phe Lys Trp Glu
            595                 600                 605

Arg Val Met Asn Phe Glu Asp Gly Gly Val Val Thr Val Thr Gln Asp
            610                 615                 620

Ser Ser Leu Gln Asp Gly Glu Phe Ile Tyr Lys Val Lys Leu Arg Gly
625                 630                 635                 640

Thr Asn Phe Pro Ser Asp Gly Pro Val Met Gln Lys Lys Thr Met Gly
                645                 650                 655

Trp Glu Ala Ser Ser Glu Arg Met Tyr Pro Glu Asp Gly Ala Leu Lys
                660                 665                 670

Gly Glu Ile Lys Gln Arg Leu Lys Leu Lys Asp Gly Gly His Tyr Asp
                675                 680                 685

Ala Glu Val Lys Thr Thr Tyr Lys Ala Lys Lys Pro Val Gln Leu Pro
            690                 695                 700

Gly Ala Tyr Asn Val Asn Ile Lys Leu Asp Ile Thr Ser His Asn Glu
705                 710                 715                 720

Asp Tyr Thr Ile Val Glu Gln Tyr Glu Arg Ala Glu Gly Arg His Ser
                725                 730                 735

Thr Gly Gly Met Asp Glu Leu Tyr Lys Gly Ser Gly Trp Ser His Pro
                740                 745                 750

Gln Phe Glu Lys
            755

<210> SEQ ID NO 28
<211> LENGTH: 159
<212> TYPE: PRT
<213> ORGANISM: Artificial Sequence
<220> FEATURE:
<223> OTHER INFORMATION: Ssp modified DnaE intein

<400> SEQUENCE: 28

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

```
Val Ile Arg Ala Thr Ser Asp His Arg Phe Leu Thr Thr Asp Tyr Gln
 65                  70                  75                  80

Leu Leu Ala Ile Glu Glu Ile Phe Ala Arg Gln Leu Asp Leu Leu Thr
                 85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
    130                 135                 140

Gln Asp His Asn Phe Leu Leu Ala Asn Gly Ala Ile Ala Ala Ala
145                 150                 155

<210> SEQ ID NO 29
<211> LENGTH: 159
<212> TYPE: PRT
<213> ORGANISM: Artificial Sequence
<220> FEATURE:
<223> OTHER INFORMATION: Ssp modified DnaE intein

<400> SEQUENCE: 29

Ala Leu Ser Phe Gly Thr Glu Ile Leu Thr Val Glu Tyr Gly Pro Leu
  1               5                  10                  15

Pro Ile Gly Lys Ile Val Ser Glu Glu Ile Asn Cys Ser Val Tyr Ser
             20                  25                  30

Val Asp Pro Glu Gly Arg Val Tyr Thr Gln Ala Ile Ala Gln Trp His
         35                  40                  45

Asp Arg Gly Glu Gln Glu Val Leu Glu Tyr Glu Leu Glu Asp Gly Ser
 50                  55                  60

Val Ile Arg Ala Thr Ser Asp His Arg Phe Leu Thr Thr Asp Tyr Gln
 65                  70                  75                  80

Leu Leu Ala Ile Glu Glu Ile Phe Ala Arg Gln Leu Asp Leu Leu Thr
                 85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
    130                 135                 140

Gln Asp His Asn Phe Leu Leu Ala Asn Gly Ala Ile Ala Ala Ala
145                 150                 155

<210> SEQ ID NO 30
<211> LENGTH: 12
<212> TYPE: PRT
<213> ORGANISM: Artificial Sequence
<220> FEATURE:
<223> OTHER INFORMATION: Mutant GFP

<400> SEQUENCE: 30

Asp His Met Val Leu His Glu Ser Val Asn Ala Ala
  1               5                  10

<210> SEQ ID NO 31
<211> LENGTH: 7
<212> TYPE: PRT
<213> ORGANISM: Artificial Sequence
<220> FEATURE:
<223> OTHER INFORMATION: Mutant GFP
```

```
<400> SEQUENCE: 31

Asp His Met Val Leu His Glu
1               5

<210> SEQ ID NO 32
<211> LENGTH: 5
<212> TYPE: PRT
<213> ORGANISM: Artificial Sequence
<220> FEATURE:
<223> OTHER INFORMATION: Mutant GFP

<400> SEQUENCE: 32

Ser Val Asn Ala Ala
1               5

<210> SEQ ID NO 33
<211> LENGTH: 20
<212> TYPE: PRT
<213> ORGANISM: Amphimedon queenslandica

<400> SEQUENCE: 33

Leu Leu Cys Phe Met Leu Leu Leu Leu Ser Gly Asp Val Glu Leu
1               5                   10                  15

Asn Pro Gly Pro
            20

<210> SEQ ID NO 34
<211> LENGTH: 20
<212> TYPE: PRT
<213> ORGANISM: Amphimedon queenslandica

<400> SEQUENCE: 34

His His Phe Met Phe Leu Leu Leu Leu Ala Gly Asp Ile Glu Leu
1               5                   10                  15

Asn Pro Gly Pro
            20

<210> SEQ ID NO 35
<211> LENGTH: 20
<212> TYPE: PRT
<213> ORGANISM: Saccoglossus kowalevskii

<400> SEQUENCE: 35

Trp Phe Leu Val Leu Leu Ser Phe Ile Leu Ser Gly Asp Ile Glu Val
1               5                   10                  15

Asn Pro Gly Pro
            20

<210> SEQ ID NO 36
<211> LENGTH: 20
<212> TYPE: PRT
<213> ORGANISM: Branchiostoma floridae

<400> SEQUENCE: 36

Lys Asn Cys Ala Met Tyr Met Leu Leu Leu Ser Gly Asp Val Glu Thr
1               5                   10                  15

Asn Pro Gly Pro
            20

<210> SEQ ID NO 37
<211> LENGTH: 20
<212> TYPE: PRT
<213> ORGANISM: Branchiostoma floridae
```

<400> SEQUENCE: 37

Met Val Ile Ser Gln Leu Met Leu Lys Leu Ala Gly Asp Val Glu Glu
1               5                   10                  15

Asn Pro Gly Pro
            20

<210> SEQ ID NO 38
<211> LENGTH: 8
<212> TYPE: PRT
<213> ORGANISM: Artificial Sequence
<220> FEATURE:
<223> OTHER INFORMATION: 2A consensus sequence
<220> FEATURE:
<221> NAME/KEY: VARIANT
<222> LOCATION: 2, 4
<223> OTHER INFORMATION: Xaa = any amino acid residue

<400> SEQUENCE: 38

Asp Xaa Glu Xaa Asn Pro Gly Pro
1               5

<210> SEQ ID NO 39
<211> LENGTH: 795
<212> TYPE: DNA
<213> ORGANISM: Artificial Sequence
<220> FEATURE:
<223> OTHER INFORMATION: Processing domain

<400> SEQUENCE: 39

| | | | | | |
|---|---|---|---|---|---|
| ctcgagggag | gatctaagtt | tgcaaatgat | tgtttgtcct | tcggaactga | gatacttaca | 60 |
| gttgaatatg | gaccacttcc | tattggaaag | attgtgagtg | aagagatcaa | ctgcagtgtt | 120 |
| tattccgtgg | atccagaggg | tagagtttac | actcaagcaa | ttgctcagtg | gcatgatagg | 180 |
| ggagaacagg | aggttcttga | atatgagttg | gaagatggtt | ctgtgataag | agctacatca | 240 |
| gatcacaggt | ttcttactac | agattaccaa | cttttggcaa | tcgaagagat | tttcgctaga | 300 |
| cagctcgatc | ttctcacttt | ggaaaatatt | aagcaaacag | aagaggcact | tgataaccat | 360 |
| aggcttccat | ttcctctttt | ggatgctgga | actattaaga | tggttaaagt | gataggaaga | 420 |
| aggtcattgg | gtgttcaaag | aatatttgat | atcggacttc | ctcaggatca | caatttctta | 480 |
| ctcgcaaacg | gtgctattgc | tgcagcttgt | ttcaatggtt | ctggttctag | agttactgag | 540 |
| cttttgtata | ggatgaagag | ggcagaaaca | tactgcccaa | gacctttact | cgcaatccat | 600 |
| ccaacagagg | ctaggcacaa | gcaaaaaatt | gttgctcctg | tgaaacagct | tttgaacttt | 660 |
| gatcttctca | agcttgcggg | agacgtcgag | tccaaccctg | gccccaggt | gctgaacacc | 720 |
| atggtgaaca | acacttctt | gtcccttcg | gtcctcatcg | tcctccttgg | cctctcctcc | 780 |
| aacttgacag | ccggc | | | | | 795 |

<210> SEQ ID NO 40
<211> LENGTH: 265
<212> TYPE: PRT
<213> ORGANISM: Artificial Sequence
<220> FEATURE:
<223> OTHER INFORMATION: Processing domain

<400> SEQUENCE: 40

Leu Glu Gly Gly Ser Lys Phe Ala Asn Asp Cys Leu Ser Phe Gly Thr
1               5                   10                  15

Glu Ile Leu Thr Val Glu Tyr Gly Pro Leu Pro Ile Gly Lys Ile Val
                20                  25                  30

```
Ser Glu Glu Ile Asn Cys Ser Val Tyr Ser Val Asp Pro Glu Gly Arg
        35                  40                  45

Val Tyr Thr Gln Ala Ile Ala Gln Trp His Asp Arg Gly Glu Gln Glu
 50                  55                  60

Val Leu Glu Tyr Glu Leu Glu Asp Gly Ser Val Ile Arg Ala Thr Ser
65                  70                  75                  80

Asp His Arg Phe Leu Thr Thr Asp Tyr Gln Leu Leu Ala Ile Glu Glu
                85                  90                  95

Ile Phe Ala Arg Gln Leu Asp Leu Leu Thr Leu Glu Asn Ile Lys Gln
                100                 105                 110

Thr Glu Ala Leu Asp Asn His Arg Leu Pro Phe Pro Leu Leu Asp
            115                 120                 125

Ala Gly Thr Ile Lys Met Val Lys Val Ile Gly Arg Arg Ser Leu Gly
        130                 135                 140

Val Gln Arg Ile Phe Asp Ile Gly Leu Pro Gln Asp His Asn Phe Leu
145                 150                 155                 160

Leu Ala Asn Gly Ala Ile Ala Ala Cys Phe Asn Gly Ser Gly Ser
                165                 170                 175

Arg Val Thr Glu Leu Leu Tyr Arg Met Lys Arg Ala Glu Thr Tyr Cys
            180                 185                 190

Pro Arg Pro Leu Leu Ala Ile His Pro Thr Glu Ala Arg His Lys Gln
        195                 200                 205

Lys Ile Val Ala Pro Val Lys Gln Leu Leu Asn Phe Asp Leu Leu Lys
    210                 215                 220

Leu Ala Gly Asp Val Glu Ser Asn Pro Gly Pro Gln Val Leu Asn Thr
225                 230                 235                 240

Met Val Asn Lys His Phe Leu Ser Leu Ser Val Leu Ile Val Leu Leu
                245                 250                 255

Gly Leu Ser Ser Asn Leu Thr Ala Gly
                260                 265

<210> SEQ ID NO 41
<211> LENGTH: 705
<212> TYPE: DNA
<213> ORGANISM: Artificial Sequence
<220> FEATURE:
<223> OTHER INFORMATION: Processing domain
<220> FEATURE:
<221> NAME/KEY: CDS
<222> LOCATION: (1)...(705)

<400> SEQUENCE: 41 ctc gag gga gga tct aag ttt gca aat gat tgt ttg tcc ttc gga act     48
Leu Glu Gly Gly Ser Lys Phe Ala Asn Asp Cys Leu Ser Phe Gly Thr
1               5                   10                  15 gag ata ctt aca gtt gaa tat gga cca ctt cct att gga aag att gtg    96
Glu Ile Leu Thr Val Glu Tyr Gly Pro Leu Pro Ile Gly Lys Ile Val
                20                  25                  30 agt gaa gag atc aac tgc agt gtt tat tcc gtg gat cca gag ggt aga  144
Ser Glu Glu Ile Asn Cys Ser Val Tyr Ser Val Asp Pro Glu Gly Arg
            35                  40                  45 gtt tac act caa gca att gct cag tgg cat gat agg gga gaa cag gag  192
Val Tyr Thr Gln Ala Ile Ala Gln Trp His Asp Arg Gly Glu Gln Glu
        50                  55                  60 gtt ctt gaa tat gag ttg gaa gat ggt tct gtg ata aga gct aca tca  240
Val Leu Glu Tyr Glu Leu Glu Asp Gly Ser Val Ile Arg Ala Thr Ser
65                  70                  75                  80
```

```
gat cac agg ttt ctt act aca gat tac caa ctt ttg gca atc gaa gag      288
Asp His Arg Phe Leu Thr Thr Asp Tyr Gln Leu Leu Ala Ile Glu Glu
        85                  90                  95 att ttc gct aga cag ctc gat ctt ctc act ttg gaa aat att aag caa      336
Ile Phe Ala Arg Gln Leu Asp Leu Leu Thr Leu Glu Asn Ile Lys Gln
100                 105                 110 aca gaa gag gca ctt gat aac cat agg ctt cca ttt cct ctt ttg gat      384
Thr Glu Glu Ala Leu Asp Asn His Arg Leu Pro Phe Pro Leu Leu Asp
            115                 120                 125 gct gga act att aag atg gtt aaa gtg ata gga aga agg tca ttg ggt      432
Ala Gly Thr Ile Lys Met Val Lys Val Ile Gly Arg Arg Ser Leu Gly
        130                 135                 140 gtt caa aga ata ttt gat atc gga ctt cct cag gat cac aat ttc tta      480
Val Gln Arg Ile Phe Asp Ile Gly Leu Pro Gln Asp His Asn Phe Leu
145                 150                 155                 160 ctc gca aac ggt gct att gct gca gct tgt tct tgt ggt tct ggt tct      528
Leu Ala Asn Gly Ala Ile Ala Ala Ala Cys Ser Cys Gly Ser Gly Ser
                165                 170                 175 aga gtt act gag ctt ttg tat agg atg aag agg gca gaa aca tac tgc      576
Arg Val Thr Glu Leu Leu Tyr Arg Met Lys Arg Ala Glu Thr Tyr Cys
            180                 185                 190 cca aga cct tta ctc gca atc cat cca aca gag gct agg cac aag caa      624
Pro Arg Pro Leu Leu Ala Ile His Pro Thr Glu Ala Arg His Lys Gln
        195                 200                 205 aaa att gtt gct cct gtg aaa cag ctt ttg aac ttt gat ctt ctc aag      672
Lys Ile Val Ala Pro Val Lys Gln Leu Leu Asn Phe Asp Leu Leu Lys
210                 215                 220 ctt gcg gga gac gtc gag tcc aac cct ggg ccc                          705
Leu Ala Gly Asp Val Glu Ser Asn Pro Gly Pro
225                 230                 235

<210> SEQ ID NO 42
<211> LENGTH: 235
<212> TYPE: PRT
<213> ORGANISM: Artificial Sequence
<220> FEATURE:
<223> OTHER INFORMATION: Processing domain

<400> SEQUENCE: 42

Leu Glu Gly Gly Ser Lys Phe Ala Asn Asp Cys Leu Ser Phe Gly Thr
1               5                   10                  15

Glu Ile Leu Thr Val Glu Tyr Gly Pro Leu Pro Ile Gly Lys Ile Val
            20                  25                  30

Ser Glu Glu Ile Asn Cys Ser Val Tyr Ser Val Asp Pro Glu Gly Arg
        35                  40                  45

Val Tyr Thr Gln Ala Ile Ala Gln Trp His Asp Arg Gly Glu Gln Glu
    50                  55                  60

Val Leu Glu Tyr Glu Leu Glu Asp Gly Ser Val Ile Arg Ala Thr Ser
65                  70                  75                  80

Asp His Arg Phe Leu Thr Thr Asp Tyr Gln Leu Leu Ala Ile Glu Glu
                85                  90                  95

Ile Phe Ala Arg Gln Leu Asp Leu Leu Thr Leu Glu Asn Ile Lys Gln
            100                 105                 110

Thr Glu Glu Ala Leu Asp Asn His Arg Leu Pro Phe Pro Leu Leu Asp
        115                 120                 125

Ala Gly Thr Ile Lys Met Val Lys Val Ile Gly Arg Arg Ser Leu Gly
    130                 135                 140

Val Gln Arg Ile Phe Asp Ile Gly Leu Pro Gln Asp His Asn Phe Leu
145                 150                 155                 160
```

```
Leu Ala Asn Gly Ala Ile Ala Ala Ala Cys Ser Cys Gly Ser Gly Ser
                165                 170                 175

Arg Val Thr Glu Leu Leu Tyr Arg Met Lys Arg Ala Glu Thr Tyr Cys
            180                 185                 190

Pro Arg Pro Leu Leu Ala Ile His Pro Thr Glu Ala Arg His Lys Gln
        195                 200                 205

Lys Ile Val Ala Pro Val Lys Gln Leu Leu Asn Phe Asp Leu Leu Lys
    210                 215                 220

Leu Ala Gly Asp Val Glu Ser Asn Pro Gly Pro
225                 230                 235

<210> SEQ ID NO 43
<211> LENGTH: 723
<212> TYPE: DNA
<213> ORGANISM: Artificial Sequence
<220> FEATURE:
<223> OTHER INFORMATION: Processing domain

<400> SEQUENCE: 43
tgtttgtcct tcggaactga gatacttaca gttgaatatg gaccacttcc tattggaaag      60
attgtgagtg aagagatcaa ctgcagtgtt tattccgtgg atccagaggg tagagtttac     120
actcaagcaa ttgctcagtg gcatgatagg ggagaacagg aggttcttga atatgagttg     180
gaagatggtt ctgtgataag agctacatca gatcacaggt ttcttactac agattaccaa     240
cttttggcaa tcgaagagat tttcgctaga cagctcgatc ttctcacttt ggaaaatatt     300
aagcaaacag aagaggcact tgataaccat aggcttccat ttcctctttt ggatgctgga     360
actattaaga tggttaaagt gataggaaga aggtcattgg gtgttcaaag aatatttgat     420
atcggacttc ctcaggatca caatttctta ctcgcaaacg tgctattgc tgcagcttgt     480 tcttgtggtt ctggtatgca gatcttcgta aagactttga ccggaaagac catcactctt     540
gaagttgaaa gctccgacac cattgataac gtgaaggcta agatccagga caaggaaggc     600
attcctccgg accagcagcg tctcatcttc gctggaaggc agcttgagga tggacgtact     660
ttggccgact acaacatcca gaaggagtcc actcttcact ggtcctccg tctccgcggc     720 ggt                                                                   723

<210> SEQ ID NO 44
<211> LENGTH: 241
<212> TYPE: PRT
<213> ORGANISM: Artificial Sequence
<220> FEATURE:
<223> OTHER INFORMATION: Processing domain

<400> SEQUENCE: 44

Cys Leu Ser Phe Gly Thr Glu Ile Leu Thr Val Glu Tyr Gly Pro Leu
  1               5                  10                  15

Pro Ile Gly Lys Ile Val Ser Glu Glu Ile Asn Cys Ser Val Tyr Ser
             20                  25                  30

Val Asp Pro Glu Gly Arg Val Tyr Thr Gln Ala Ile Ala Gln Trp His
         35                  40                  45

Asp Arg Gly Glu Gln Glu Val Leu Glu Tyr Leu Glu Asp Gly Ser
     50                  55                  60

Val Ile Arg Ala Thr Ser Asp His Arg Phe Leu Thr Thr Asp Tyr Gln
 65                  70                  75                  80

Leu Leu Ala Ile Glu Glu Ile Phe Ala Arg Gln Leu Asp Leu Leu Thr
                 85                  90                  95
```

-continued

```
Leu Glu Asn Ile Lys Gln Thr Glu Glu Ala Leu Asp Asn His Arg Leu
            100                 105                 110
Pro Phe Pro Leu Leu Asp Ala Gly Thr Ile Lys Met Val Lys Val Ile
            115                 120                 125
Gly Arg Arg Ser Leu Gly Val Gln Arg Ile Phe Asp Ile Gly Leu Pro
130                 135                 140
Gln Asp His Asn Phe Leu Leu Ala Asn Gly Ala Ile Ala Ala Cys
145                 150                 155                 160
Ser Cys Gly Ser Gly Met Gln Ile Phe Val Lys Thr Leu Thr Gly Lys
                165                 170                 175
Thr Ile Thr Leu Glu Val Glu Ser Ser Asp Thr Ile Asp Asn Val Lys
            180                 185                 190
Ala Lys Ile Gln Asp Lys Glu Gly Ile Pro Pro Asp Gln Gln Arg Leu
        195                 200                 205
Ile Phe Ala Gly Arg Gln Leu Glu Asp Gly Arg Thr Leu Ala Asp Tyr
    210                 215                 220
Asn Ile Gln Lys Glu Ser Thr Leu His Leu Val Leu Arg Leu Arg Gly
225                 230                 235                 240
Gly
```

<210> SEQ ID NO 45
<211> LENGTH: 576
<212> TYPE: DNA
<213> ORGANISM: Artificial Sequence
<220> FEATURE:
<223> OTHER INFORMATION: Processing domain
<220> FEATURE:
<221> NAME/KEY: CDS
<222> LOCATION: (1)...(576)

<400> SEQUENCE: 45

```
tgt ttg tcc ttc gga act gag ata ctt aca gtt gaa tat gga cca ctt      48
Cys Leu Ser Phe Gly Thr Glu Ile Leu Thr Val Glu Tyr Gly Pro Leu
1               5                   10                  15 cct att gga aag att gtg agt gaa gag atc aac tgc agt gtt tat tcc     96
Pro Ile Gly Lys Ile Val Ser Glu Glu Ile Asn Cys Ser Val Tyr Ser
                20                  25                  30 gtg gat cca gag ggt aga gtt tac act caa gca att gct cag tgg cat    144
Val Asp Pro Glu Gly Arg Val Tyr Thr Gln Ala Ile Ala Gln Trp His
            35                  40                  45 gat agg gga gaa cag gag gtt ctt gaa tat gag ttg gaa gat ggt tct    192
Asp Arg Gly Glu Gln Glu Val Leu Glu Tyr Glu Leu Glu Asp Gly Ser
        50                  55                  60 gtg ata aga gct aca tca gat cac agg ttt ctt act aca gat tac caa    240
Val Ile Arg Ala Thr Ser Asp His Arg Phe Leu Thr Thr Asp Tyr Gln
65                  70                  75                  80 ctt ttg gca atc gaa gag att ttc gct aga cag ctc gat ctt ctc act    288
Leu Leu Ala Ile Glu Glu Ile Phe Ala Arg Gln Leu Asp Leu Leu Thr
                85                  90                  95 ttg gaa aat att aag caa aca gag gag gca ctt gat aac cat agg ctt    336
Leu Glu Asn Ile Lys Gln Thr Glu Glu Ala Leu Asp Asn His Arg Leu
            100                 105                 110 cca ttt cct ctt ttg gat gct gga act att aag atg gtt aaa gtg ata    384
Pro Phe Pro Leu Leu Asp Ala Gly Thr Ile Lys Met Val Lys Val Ile
        115                 120                 125 gga aga agg tca ttg ggt gtt caa aga ata ttt gat atc gga ctt cct    432
Gly Arg Arg Ser Leu Gly Val Gln Arg Ile Phe Asp Ile Gly Leu Pro
    130                 135                 140
```

```
cag gat cac aat ttc tta ctc gca aac ggt gct att gct gca gct tgt      480
Gln Asp His Asn Phe Leu Leu Ala Asn Gly Ala Ile Ala Ala Ala Cys
145                 150                 155                 160 tct tgt ggt tct ggt tct aga gat gga ttc tgc att ctc tat ctg ctc      528
Ser Cys Gly Ser Gly Ser Arg Asp Gly Phe Cys Ile Leu Tyr Leu Leu
                165                 170                 175 ctg atc ctc ttg atg aga tct ggt gac gtt gaa acc aat cca ggg ccc      576
Leu Ile Leu Leu Met Arg Ser Gly Asp Val Glu Thr Asn Pro Gly Pro
            180                 185                 190
```

<210> SEQ ID NO 46
<211> LENGTH: 192
<212> TYPE: PRT
<213> ORGANISM: Artificial Sequence
<220> FEATURE:
<223> OTHER INFORMATION: Processing domain

<400> SEQUENCE: 46

```
Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
    130                 135                 140

Gln Asp His Asn Phe Leu Leu Ala Asn Gly Ala Ile Ala Ala Ala Cys
145                 150                 155                 160

Ser Cys Gly Ser Gly Ser Arg Asp Gly Phe Cys Ile Leu Tyr Leu Leu
                165                 170                 175

Leu Ile Leu Leu Met Arg Ser Gly Asp Val Glu Thr Asn Pro Gly Pro
            180                 185                 190
```

<210> SEQ ID NO 47
<211> LENGTH: 1014
<212> TYPE: DNA
<213> ORGANISM: Artificial Sequence
<220> FEATURE:
<223> OTHER INFORMATION: Processing domain
<220> FEATURE:
<221> NAME/KEY: CDS
<222> LOCATION: (1)...(1014)

<400> SEQUENCE: 47

```
ctc gag gga gga tct aag ttt gca aat gat tgt ttg tcc ttc gga act      48
Leu Glu Gly Gly Ser Lys Phe Ala Asn Asp Cys Leu Ser Phe Gly Thr
1               5                   10                  15 gag ata ctt aca gtt gaa tat gga cca ctt cct att gga aag att gtg      96
Glu Ile Leu Thr Val Glu Tyr Gly Pro Leu Pro Ile Gly Lys Ile Val
            20                  25                  30
```

| | |
|---|---|
| agt gaa gag atc aac tgc agt gtt tat tcc gtg gat cca gag ggt aga<br>Ser Glu Glu Ile Asn Cys Ser Val Tyr Ser Val Asp Pro Glu Gly Arg<br>35                       40                     45 | 144 |
| gtt tac act caa gca att gct cag tgg cat gat agg gga gaa cag gag<br>Val Tyr Thr Gln Ala Ile Ala Gln Trp His Asp Arg Gly Glu Gln Glu<br> 50                     55                    60 | 192 |
| gtt ctt gaa tat gag ttg gaa gat ggt tct gtg ata aga gct aca tca<br>Val Leu Glu Tyr Glu Leu Glu Asp Gly Ser Val Ile Arg Ala Thr Ser<br>65                       70                   75               80 | 240 |
| gat cac agg ttt ctt act aca gat tac caa ctt ttg gca atc gaa gag<br>Asp His Arg Phe Leu Thr Thr Asp Tyr Gln Leu Leu Ala Ile Glu Glu<br>               85                    90                   95 | 288 |
| att ttc gct aga cag ctc gat ctc ctc act ttg gaa aat att aag caa<br>Ile Phe Ala Arg Gln Leu Asp Leu Leu Thr Leu Glu Asn Ile Lys Gln<br>             100                 105             110 | 336 |
| aca gaa gag gca ctt gat aac cat agg ctt cca ttt cct ctt ttg gat<br>Thr Glu Glu Ala Leu Asp Asn His Arg Leu Pro Phe Pro Leu Leu Asp<br>           115                 120              125 | 384 |
| gct gga act att aag atg gtt aaa gtg ata gga aga agg tca ttg ggt<br>Ala Gly Thr Ile Lys Met Val Lys Val Ile Gly Arg Arg Ser Leu Gly<br>130                     135                 140 | 432 |
| gtt caa aga ata ttt gat atc gga ctt cct cag gat cac aat ttc tta<br>Val Gln Arg Ile Phe Asp Ile Gly Leu Pro Gln Asp His Asn Phe Leu<br>145                    150                155              160 | 480 |
| ctc gca aac ggt gct att gct gca gct tgt ttc aat ggt tct ggt tct<br>Leu Ala Asn Gly Ala Ile Ala Ala Ala Cys Phe Asn Gly Ser Gly Ser<br>                 165                 170              175 | 528 |
| aga gag tct gga gct atc tct ggc gat agt ctg atc agc ctg gct agc<br>Arg Glu Ser Gly Ala Ile Ser Gly Asp Ser Leu Ile Ser Leu Ala Ser<br>                  180                185              190 | 576 |
| aca gga aaa aga gtt tct att aaa gat ttg tta gat gaa aaa gat ttt<br>Thr Gly Lys Arg Val Ser Ile Lys Asp Leu Leu Asp Glu Lys Asp Phe<br>             195                 200              205 | 624 |
| gaa ata tgg gca att aat gaa cag acg atg aag cta gaa tca gct aaa<br>Glu Ile Trp Ala Ile Asn Glu Gln Thr Met Lys Leu Glu Ser Ala Lys<br>210                     215                 220 | 672 |
| gtt agt cgt gta ttt tgt act ggc aaa aag cta gtt tat att cta aaa<br>Val Ser Arg Val Phe Cys Thr Gly Lys Lys Leu Val Tyr Ile Leu Lys<br>225                    230                235              240 | 720 |
| act cga cta ggt aga act atc aag gca aca gca aat cat aga ttt tta<br>Thr Arg Leu Gly Arg Thr Ile Lys Ala Thr Ala Asn His Arg Phe Leu<br>                 245                 250              255 | 768 |
| act att gat ggt tgg aaa aga tta gat gag cta tct tta aaa gag cat<br>Thr Ile Asp Gly Trp Lys Arg Leu Asp Glu Leu Ser Leu Lys Glu His<br>                  260                265              270 | 816 |
| att gct cta ccc cgt aaa cta gaa agc tcc tct tta caa ttg tca cca<br>Ile Ala Leu Pro Arg Lys Leu Glu Ser Ser Ser Leu Gln Leu Ser Pro<br>             275                 280              285 | 864 |
| gaa ata gaa aag ttg tct cag agt gat att tac tgg gac tcc atc gtt<br>Glu Ile Glu Lys Leu Ser Gln Ser Asp Ile Tyr Trp Asp Ser Ile Val<br>290                     295                 300 | 912 |
| tct att acg gag act gga gtc gaa gag gtt ttt gat ttg act gtg cca<br>Ser Ile Thr Glu Thr Gly Val Glu Glu Val Phe Asp Leu Thr Val Pro<br>305                     310                 315              320 | 960 |
| gga cca cat aac ttt gtc gcg aat gac atc att gta cac aac agc cgc<br>Gly Pro His Asn Phe Val Ala Asn Asp Ile Ile Val His Asn Ser Arg<br>                 325                 330              335 | 1008 |
| ggg ccc<br>Gly Pro | 1014 |

<210> SEQ ID NO 48
<211> LENGTH: 338
<212> TYPE: PRT
<213> ORGANISM: Artificial Sequence
<220> FEATURE:
<223> OTHER INFORMATION: Processing domain

<400> SEQUENCE: 48

```
Leu Glu Gly Gly Ser Lys Phe Ala Asn Asp Cys Leu Ser Phe Gly Thr
 1               5                  10                  15
Glu Ile Leu Thr Val Glu Tyr Gly Pro Leu Pro Ile Gly Lys Ile Val
            20                  25                  30
Ser Glu Glu Ile Asn Cys Ser Val Tyr Ser Val Asp Pro Glu Gly Arg
        35                  40                  45
Val Tyr Thr Gln Ala Ile Ala Gln Trp His Asp Arg Gly Glu Gln Glu
    50                  55                  60
Val Leu Glu Tyr Glu Leu Glu Asp Gly Ser Val Ile Arg Ala Thr Ser
65                  70                  75                  80
Asp His Arg Phe Leu Thr Thr Asp Tyr Gln Leu Leu Ala Ile Glu Glu
                85                  90                  95
Ile Phe Ala Arg Gln Leu Asp Leu Leu Thr Leu Glu Asn Ile Lys Gln
            100                 105                 110
Thr Glu Glu Ala Leu Asp Asn His Arg Leu Pro Phe Pro Leu Leu Asp
        115                 120                 125
Ala Gly Thr Ile Lys Met Val Lys Val Ile Gly Arg Arg Ser Leu Gly
    130                 135                 140
Val Gln Arg Ile Phe Asp Ile Gly Leu Pro Gln Asp His Asn Phe Leu
145                 150                 155                 160
Leu Ala Asn Gly Ala Ile Ala Ala Ala Cys Phe Asn Gly Ser Gly Ser
                165                 170                 175
Arg Glu Ser Gly Ala Ile Ser Gly Asp Ser Leu Ile Ser Leu Ala Ser
            180                 185                 190
Thr Gly Lys Arg Val Ser Ile Lys Asp Leu Leu Asp Glu Lys Asp Phe
        195                 200                 205
Glu Ile Trp Ala Ile Asn Glu Gln Thr Met Lys Leu Glu Ser Ala Lys
    210                 215                 220
Val Ser Arg Val Phe Cys Thr Gly Lys Lys Leu Val Tyr Ile Leu Lys
225                 230                 235                 240
Thr Arg Leu Gly Arg Thr Ile Lys Ala Thr Ala Asn His Arg Phe Leu
                245                 250                 255
Thr Ile Asp Gly Trp Lys Arg Leu Asp Glu Leu Ser Leu Lys Glu His
            260                 265                 270
Ile Ala Leu Pro Arg Lys Leu Glu Ser Ser Leu Gln Leu Ser Pro
        275                 280                 285
Glu Ile Glu Lys Leu Ser Gln Ser Asp Ile Tyr Trp Asp Ser Ile Val
    290                 295                 300
Ser Ile Thr Glu Thr Gly Val Glu Glu Val Phe Asp Leu Thr Val Pro
305                 310                 315                 320
Gly Pro His Asn Phe Val Ala Asn Asp Ile Ile Val His Asn Ser Arg
                325                 330                 335
Gly Pro
```

<210> SEQ ID NO 49
<211> LENGTH: 981
<212> TYPE: DNA

<213> ORGANISM: Artificial Sequence
<220> FEATURE:
<223> OTHER INFORMATION: Processing domain
<220> FEATURE:
<221> NAME/KEY: CDS
<222> LOCATION: (1)...(981)

<400> SEQUENCE: 49

```
ctc gag tat gca ttg tcc ttc gga act gag ata ctt aca gtt gaa tat      48
Leu Glu Tyr Ala Leu Ser Phe Gly Thr Glu Ile Leu Thr Val Glu Tyr
1               5                   10                  15 gga cca ctt cct att gga aag att gtg agt gaa gag atc aac tgc agt      96
Gly Pro Leu Pro Ile Gly Lys Ile Val Ser Glu Glu Ile Asn Cys Ser
            20                  25                  30 gtt tat tcc gtg gat cca gag ggt aga gtt tac act caa gca att gct     144
Val Tyr Ser Val Asp Pro Glu Gly Arg Val Tyr Thr Gln Ala Ile Ala
        35                  40                  45 cag tgg cat gat agg gga gaa cag gag gtt ctt gaa tat gag ttg gaa     192
Gln Trp His Asp Arg Gly Glu Gln Glu Val Leu Glu Tyr Glu Leu Glu
50                  55                  60 gat ggt tct gtg ata aga gct aca tca gat cac agg ttt ctt act aca     240
Asp Gly Ser Val Ile Arg Ala Thr Ser Asp His Arg Phe Leu Thr Thr
65                  70                  75                  80 gat tac caa ctt ttg gca atc gaa gag att ttc gct aga cag ctc gat     288
Asp Tyr Gln Leu Leu Ala Ile Glu Glu Ile Phe Ala Arg Gln Leu Asp
                85                  90                  95 ctt ctc act ttg gaa aat att aag caa aca gaa gag gca ctt gat aac     336
Leu Leu Thr Leu Glu Asn Ile Lys Gln Thr Glu Glu Ala Leu Asp Asn
            100                 105                 110 cat agg ctt cca ttt cct ctt ttg gat gct gga act att aag atg gtt     384
His Arg Leu Pro Phe Pro Leu Leu Asp Ala Gly Thr Ile Lys Met Val
        115                 120                 125 aaa gtg ata gga aga agg tca ttg ggt gtt caa aga ata ttt gat atc     432
Lys Val Ile Gly Arg Arg Ser Leu Gly Val Gln Arg Ile Phe Asp Ile
130                 135                 140 gga ctt cct cag gat cac aat ttc tta ctc gca aac ggt gct att gct     480
Gly Leu Pro Gln Asp His Asn Phe Leu Leu Ala Asn Gly Ala Ile Ala
145                 150                 155                 160 gca gct ggt ggt tct aga gag tct gga gct atc tct ggc gat agt ctg     528
Ala Ala Gly Gly Ser Arg Glu Ser Gly Ala Ile Ser Gly Asp Ser Leu
                165                 170                 175 atc agc ctg gct agc aca gga aaa aga gtt tct att aaa gat ttg tta     576
Ile Ser Leu Ala Ser Thr Gly Lys Arg Val Ser Ile Lys Asp Leu Leu
            180                 185                 190 gat gaa aaa gat ttt gaa ata tgg gca att aat gaa cag acg atg aag     624
Asp Glu Lys Asp Phe Glu Ile Trp Ala Ile Asn Glu Gln Thr Met Lys
        195                 200                 205 cta gaa tca gct aaa gtt agt cgt gta ttt tgt act ggc aaa aag cta     672
Leu Glu Ser Ala Lys Val Ser Arg Val Phe Cys Thr Gly Lys Lys Leu
210                 215                 220 gtt tat att cta aaa act cga cta ggt aga act atc aag gca aca gca     720
Val Tyr Ile Leu Lys Thr Arg Leu Gly Arg Thr Ile Lys Ala Thr Ala
225                 230                 235                 240 aat cat aga ttt tta act att gat ggt tgg aaa aga tta gat gag cta     768
Asn His Arg Phe Leu Thr Ile Asp Gly Trp Lys Arg Leu Asp Glu Leu
                245                 250                 255 tct tta aaa gag cat att gct cta ccc cgt aaa cta gaa agc tcc tct     816
Ser Leu Lys Glu His Ile Ala Leu Pro Arg Lys Leu Glu Ser Ser Ser
            260                 265                 270 tta caa ttg tca cca gaa ata gaa aag ttg tct cag agt gat att tac     864
Leu Gln Leu Ser Pro Glu Ile Glu Lys Leu Ser Gln Ser Asp Ile Tyr
```

```
            275                 280                 285
tgg gac tcc atc gtt tct att acg gag act gga gtc gaa gag gtt ttt    912
Trp Asp Ser Ile Val Ser Ile Thr Glu Thr Gly Val Glu Glu Val Phe
290                 295                 300 gat ttg act gtg cca gga cca cat aac ttt gtc gcg aat gac atc att    960
Asp Leu Thr Val Pro Gly Pro His Asn Phe Val Ala Asn Asp Ile Ile
305                 310                 315                 320 gta cac aac agc cgc ggg ccc                                        981
Val His Asn Ser Arg Gly Pro
                325
```

<210> SEQ ID NO 50
<211> LENGTH: 327
<212> TYPE: PRT
<213> ORGANISM: Artificial Sequence
<220> FEATURE:
<223> OTHER INFORMATION: Processing domain

<400> SEQUENCE: 50

```
Leu Glu Tyr Ala Leu Ser Phe Gly Thr Glu Ile Leu Thr Val Glu Tyr
 1               5                  10                  15

Gly Pro Leu Pro Ile Gly Lys Ile Val Ser Glu Glu Ile Asn Cys Ser
            20                  25                  30

Val Tyr Ser Val Asp Pro Glu Gly Arg Val Tyr Thr Gln Ala Ile Ala
        35                  40                  45

Gln Trp His Asp Arg Gly Glu Gln Val Leu Glu Tyr Glu Leu Glu
    50                  55                  60

Asp Gly Ser Val Ile Arg Ala Thr Ser Asp His Arg Phe Leu Thr Thr
65                  70                  75                  80

Asp Tyr Gln Leu Leu Ala Ile Glu Glu Ile Phe Ala Arg Gln Leu Asp
                85                  90                  95

Leu Leu Thr Leu Glu Asn Ile Lys Gln Thr Glu Glu Ala Leu Asp Asn
            100                 105                 110

His Arg Leu Pro Phe Pro Leu Leu Asp Ala Gly Thr Ile Lys Met Val
        115                 120                 125

Lys Val Ile Gly Arg Arg Ser Leu Gly Val Gln Arg Ile Phe Asp Ile
    130                 135                 140

Gly Leu Pro Gln Asp His Asn Phe Leu Leu Ala Asn Gly Ala Ile Ala
145                 150                 155                 160

Ala Ala Gly Gly Ser Arg Glu Ser Gly Ala Ile Ser Gly Asp Ser Leu
                165                 170                 175

Ile Ser Leu Ala Ser Thr Gly Lys Arg Val Ser Ile Lys Asp Leu Leu
            180                 185                 190

Asp Glu Lys Asp Phe Glu Ile Trp Ala Ile Asn Glu Gln Thr Met Lys
        195                 200                 205

Leu Glu Ser Ala Lys Val Ser Arg Val Phe Cys Thr Gly Lys Lys Leu
    210                 215                 220

Val Tyr Ile Leu Lys Thr Arg Leu Gly Arg Thr Ile Lys Ala Thr Ala
225                 230                 235                 240

Asn His Arg Phe Leu Thr Ile Asp Gly Trp Lys Arg Leu Asp Glu Leu
                245                 250                 255

Ser Leu Lys Glu His Ile Ala Leu Pro Arg Lys Leu Glu Ser Ser
            260                 265                 270

Leu Gln Leu Ser Pro Glu Ile Glu Lys Leu Ser Gln Ser Asp Ile Tyr
        275                 280                 285

Trp Asp Ser Ile Val Ser Ile Thr Glu Thr Gly Val Glu Glu Val Phe
```

```
                    290                 295                 300
Asp Leu Thr Val Pro Gly Pro His Asn Phe Val Ala Asn Asp Ile Ile
305                 310                 315                 320

Val His Asn Ser Arg Gly Pro
                325
```

<210> SEQ ID NO 51
<211> LENGTH: 705
<212> TYPE: DNA
<213> ORGANISM: Artificial Sequence
<220> FEATURE:
<223> OTHER INFORMATION: Processing domain
<220> FEATURE:
<221> NAME/KEY: CDS
<222> LOCATION: (1)...(705)

<400> SEQUENCE: 51

```
ctc gag gga gga tct aag ttt gca aat gat tgt ttg tcc ttc gga act      48
Leu Glu Gly Gly Ser Lys Phe Ala Asn Asp Cys Leu Ser Phe Gly Thr
1               5                   10                  15 gag ata ctt aca gtt gaa tat gga cca ctt cct att gga aag att gtg      96
Glu Ile Leu Thr Val Glu Tyr Gly Pro Leu Pro Ile Gly Lys Ile Val
                20                  25                  30 agt gaa gag atc aac tgc agt gtt tat tcc gtg gat cca gag ggt aga     144
Ser Glu Glu Ile Asn Cys Ser Val Tyr Ser Val Asp Pro Glu Gly Arg
            35                  40                  45 gtt tac act caa gca att gct cag tgg cat gat agg gga gaa cag gag     192
Val Tyr Thr Gln Ala Ile Ala Gln Trp His Asp Arg Gly Glu Gln Glu
        50                  55                  60 gtt ctt gaa tat gag ttg gaa gat ggt tct gtg ata aga gct aca tca     240
Val Leu Glu Tyr Glu Leu Glu Asp Gly Ser Val Ile Arg Ala Thr Ser
65                  70                  75                  80 gat cac agg ttt ctt act aca gat tac caa ctt ttg gca atc gaa gag     288
Asp His Arg Phe Leu Thr Thr Asp Tyr Gln Leu Leu Ala Ile Glu Glu
                85                  90                  95 att ttc gct aga cag ctc gat ctt ctc act ttg gaa aat att aag caa     336
Ile Phe Ala Arg Gln Leu Asp Leu Leu Thr Leu Glu Asn Ile Lys Gln
            100                 105                 110 aca gaa gag gca ctt gat aac cat agg ctt cca ttt cct ctt ttg gat     384
Thr Glu Glu Ala Leu Asp Asn His Arg Leu Pro Phe Pro Leu Leu Asp
        115                 120                 125 gct gga act att aag atg gtt aaa gtg ata gga aga agg tca ttg ggt     432
Ala Gly Thr Ile Lys Met Val Lys Val Ile Gly Arg Arg Ser Leu Gly
    130                 135                 140 gtt caa aga ata ttt gat atc gga ctt cct cag gat cac aat ttc tta     480
Val Gln Arg Ile Phe Asp Ile Gly Leu Pro Gln Asp His Asn Phe Leu
145                 150                 155                 160 ctc gca aac ggt gct att gct gca gct tgt ttc aat ggt tct ggt tct     528
Leu Ala Asn Gly Ala Ile Ala Ala Ala Cys Phe Asn Gly Ser Gly Ser
                165                 170                 175 aga gtt act gag ctt ttg tat agg atg aag agg gca gaa aca tac tgc     576
Arg Val Thr Glu Leu Leu Tyr Arg Met Lys Arg Ala Glu Thr Tyr Cys
            180                 185                 190 cca aga cct tta ctc gca atc cat cca aca gag gct agg cac aag caa     624
Pro Arg Pro Leu Leu Ala Ile His Pro Thr Glu Ala Arg His Lys Gln
        195                 200                 205 aaa att gtt gct cct gtg aaa cag ctt ttg aac ttt gat ctt ctc aag     672
Lys Ile Val Ala Pro Val Lys Gln Leu Leu Asn Phe Asp Leu Leu Lys
    210                 215                 220 ctt gcg gga gac gtc gag tcc aac cct ggg ccc                         705
Leu Ala Gly Asp Val Glu Ser Asn Pro Gly Pro
```

<210> SEQ ID NO 52
<211> LENGTH: 235
<212> TYPE: PRT
<213> ORGANISM: Artificial Sequence
<220> FEATURE:
<223> OTHER INFORMATION: Processing domain

<400> SEQUENCE: 52

```
Leu Glu Gly Gly Ser Lys Phe Ala Asn Asp Cys Leu Ser Phe Gly Thr
 1               5                  10                  15
Glu Ile Leu Thr Val Glu Tyr Gly Pro Leu Pro Ile Gly Lys Ile Val
            20                  25                  30
Ser Glu Glu Ile Asn Cys Ser Val Tyr Ser Val Asp Pro Glu Gly Arg
        35                  40                  45
Val Tyr Thr Gln Ala Ile Ala Gln Trp His Asp Arg Gly Glu Gln Glu
    50                  55                  60
Val Leu Glu Tyr Glu Leu Glu Asp Gly Ser Val Ile Arg Ala Thr Ser
65                  70                  75                  80
Asp His Arg Phe Leu Thr Thr Asp Tyr Gln Leu Leu Ala Ile Glu Glu
                85                  90                  95
Ile Phe Ala Arg Gln Leu Asp Leu Leu Thr Leu Glu Asn Ile Lys Gln
            100                 105                 110
Thr Glu Glu Ala Leu Asp Asn His Arg Leu Pro Phe Pro Leu Leu Asp
        115                 120                 125
Ala Gly Thr Ile Lys Met Val Lys Val Ile Gly Arg Arg Ser Leu Gly
    130                 135                 140
Val Gln Arg Ile Phe Asp Ile Gly Leu Pro Gln Asp His Asn Phe Leu
145                 150                 155                 160
Leu Ala Asn Gly Ala Ile Ala Ala Cys Phe Asn Gly Ser Gly Ser
                165                 170                 175
Arg Val Thr Glu Leu Leu Tyr Arg Met Lys Arg Ala Glu Thr Tyr Cys
            180                 185                 190
Pro Arg Pro Leu Leu Ala Ile His Pro Thr Glu Ala Arg His Lys Gln
        195                 200                 205
Lys Ile Val Ala Pro Val Lys Gln Leu Leu Asn Phe Asp Leu Leu Lys
    210                 215                 220
Leu Ala Gly Asp Val Glu Ser Asn Pro Gly Pro
225                 230                 235
```

<210> SEQ ID NO 53
<211> LENGTH: 813
<212> TYPE: DNA
<213> ORGANISM: Artificial Sequence
<220> FEATURE:
<223> OTHER INFORMATION: Processing domain
<220> FEATURE:
<221> NAME/KEY: CDS
<222> LOCATION: (1)...(813)

<400> SEQUENCE: 53

```
tgt ttg tcc ttc gga act gag ata ctt aca gtt gaa tat gga cca ctt    48
Cys Leu Ser Phe Gly Thr Glu Ile Leu Thr Val Glu Tyr Gly Pro Leu
 1               5                  10                  15 cct att gga aag att gtg agt gaa gag atc aac tgc agt gtt tat tcc    96
Pro Ile Gly Lys Ile Val Ser Glu Glu Ile Asn Cys Ser Val Tyr Ser
            20                  25                  30 gtg gat cca gag ggt aga gtt tac act caa gca att gct cag tgg cat   144
```

```
                Val Asp Pro Glu Gly Arg Val Tyr Thr Gln Ala Ile Ala Gln Trp His
                         35                  40                  45 gat agg gga gaa cag gag gtt ctt gaa tat gag ttg gaa gat ggt tct         192
Asp Arg Gly Glu Gln Glu Val Leu Glu Tyr Glu Leu Glu Asp Gly Ser
 50                  55                  60 gtg ata aga gct aca tca gat cac agg ttt ctt act aca gat tac caa         240
Val Ile Arg Ala Thr Ser Asp His Arg Phe Leu Thr Thr Asp Tyr Gln
 65                  70                  75                  80 ctt ttg gca atc gaa gag att ttc gct aga cag ctc gat ctt ctc act         288
Leu Leu Ala Ile Glu Glu Ile Phe Ala Arg Gln Leu Asp Leu Leu Thr
                 85                  90                  95 ttg gaa aat att aag caa aca gaa gag gca ctt gat aac cat agg ctt         336
Leu Glu Asn Ile Lys Gln Thr Glu Glu Ala Leu Asp Asn His Arg Leu
                100                 105                 110 cca ttt cct ctt ttg gat gct gga act att aag atg gtt aaa gtg ata         384
Pro Phe Pro Leu Leu Asp Ala Gly Thr Ile Lys Met Val Lys Val Ile
            115                 120                 125 gga aga agg tca ttg ggt gtt caa aga ata ttt gat atc gga ctt cct         432
Gly Arg Arg Ser Leu Gly Val Gln Arg Ile Phe Asp Ile Gly Leu Pro
        130                 135                 140 cag gat cac aat ttc tta ctc gca aac ggt gct att gct gca gct tgt         480
Gln Asp His Asn Phe Leu Leu Ala Asn Gly Ala Ile Ala Ala Ala Cys
145                 150                 155                 160 tct tgt ggt tct ggt tct aga gga tct ggc gat gga ttc tgc att ctc         528
Ser Cys Gly Ser Gly Ser Arg Gly Ser Gly Asp Gly Phe Cys Ile Leu
                165                 170                 175 tat ctg ctc ctg atc ctc ttg atg agg tct ggt gac gtt gaa acc aac         576
Tyr Leu Leu Leu Ile Leu Leu Met Arg Ser Gly Asp Val Glu Thr Asn
            180                 185                 190 cct ggg ccc atg cag atc ttc gta aag act ttg acc gga aag acc atc         624
Pro Gly Pro Met Gln Ile Phe Val Lys Thr Leu Thr Gly Lys Thr Ile
        195                 200                 205 act ctt gaa gtt gaa agc tcc gac acc att gat aac gtg aag gct aag         672
Thr Leu Glu Val Glu Ser Ser Asp Thr Ile Asp Asn Val Lys Ala Lys
210                 215                 220 atc cag gac aag gaa ggc att cct ccg gac cag cag cgt ctc atc ttc         720
Ile Gln Asp Lys Glu Gly Ile Pro Pro Asp Gln Gln Arg Leu Ile Phe
225                 230                 235                 240 gct gga agg cag ctt gag gat gga cgt act ttg gcc gac tac aac atc         768
Ala Gly Arg Gln Leu Glu Asp Gly Arg Thr Leu Ala Asp Tyr Asn Ile
                245                 250                 255 cag aag gag tcc act ctt cac ttg gtc ctc cgt ctc cgc ggc ggt             813
Gln Lys Glu Ser Thr Leu His Leu Val Leu Arg Leu Arg Gly Gly
            260                 265                 270

<210> SEQ ID NO 54
<211> LENGTH: 271
<212> TYPE: PRT
<213> ORGANISM: Artificial Sequence
<220> FEATURE:
<223> OTHER INFORMATION: Processing domain

<400> SEQUENCE: 54

Cys Leu Ser Phe Gly Thr Glu Ile Leu Thr Val Glu Tyr Gly Pro Leu
  1               5                  10                  15

Pro Ile Gly Lys Ile Val Ser Glu Glu Ile Asn Cys Ser Val Tyr Ser
                 20                  25                  30

Val Asp Pro Glu Gly Arg Val Tyr Thr Gln Ala Ile Ala Gln Trp His
             35                  40                  45

Asp Arg Gly Glu Gln Glu Val Leu Glu Tyr Glu Leu Glu Asp Gly Ser
```

-continued

```
                     50                      55                      60
Val Ile Arg Ala Thr Ser Asp His Arg Phe Leu Thr Thr Asp Tyr Gln
65                      70                      75                      80

Leu Leu Ala Ile Glu Glu Ile Phe Ala Arg Gln Leu Asp Leu Leu Thr
                        85                      90                      95

Leu Glu Asn Ile Lys Gln Thr Glu Glu Ala Leu Asp Asn His Arg Leu
                        100                     105                     110

Pro Phe Pro Leu Leu Asp Ala Gly Thr Ile Lys Met Val Lys Val Ile
                115                     120                     125

Gly Arg Arg Ser Leu Gly Val Gln Arg Ile Phe Asp Ile Gly Leu Pro
        130                     135                     140

Gln Asp His Asn Phe Leu Leu Ala Asn Gly Ala Ile Ala Ala Ala Cys
145                     150                     155                     160

Ser Cys Gly Ser Gly Ser Arg Gly Ser Gly Asp Gly Phe Cys Ile Leu
                165                     170                     175

Tyr Leu Leu Ile Leu Leu Met Arg Ser Gly Asp Val Glu Thr Asn
                180                     185                     190

Pro Gly Pro Met Gln Ile Phe Val Lys Thr Leu Thr Gly Lys Thr Ile
        195                     200                     205

Thr Leu Glu Val Glu Ser Ser Asp Thr Ile Asp Asn Val Lys Ala Lys
        210                     215                     220

Ile Gln Asp Lys Glu Gly Ile Pro Pro Asp Gln Gln Arg Leu Ile Phe
225                     230                     235                     240

Ala Gly Arg Gln Leu Glu Asp Gly Arg Thr Leu Ala Asp Tyr Asn Ile
                245                     250                     255

Gln Lys Glu Ser Thr Leu His Leu Val Leu Arg Leu Arg Gly Gly
                260                     265                     270
```

AUTO-PROCESSING DOMAINS FOR POLYPEPTIDE EXPRESSION

CROSS-REFERENCE TO RELATED APPLICATIONS

The present application claims the benefit of priority under 35 U.S.C. §119(e) of U.S. Provisional Patent Application No. 61/563,508 entitled, "Coordinate expression of multiple proteins in eukaryotes" filed on Nov. 23, 2011, and U.S. Provisional Patent Application No. 61/564,808 entitled, "Auto-processing domains that enable multi-protein expression" filed on Nov. 29, 2011. The entirety of each of these applications is hereby incorporated by reference.

STATEMENT REGARDING FEDERALLY SPONSORED R&D

This invention was made with Government support under Grant No. 2008-34135-19407 awarded by the United Stated Department of Agriculture Tropical and Subtropical Agricultural Research program. The Government has certain rights in this invention.

REFERENCE TO SEQUENCE LISTING, TABLE, OR COMPUTER PROGRAM LISTING

The present application is being filed along with a Sequence Listing in electronic format. The Sequence Listing is provided as a file entitled UOH46A-SEQUENCE.TXT, created Nov. 20, 2012, last modified Nov. 20, 2012 which is 135,861 bytes in size. The information in the electronic format of the Sequence Listing is incorporated herein by reference in its entirety.

FIELD

The field relates generally to constructs, systems, and methods for polypeptide expression.

SUMMARY

Some aspects include a method of expressing at least two separate polypeptides in a cell. In some embodiments, the method includes initiating translation of a single polynucleotide encoding, from 5' to 3': a first polypeptide of interest; a processing unit that includes an N-terminal autocatalytic cleavage domain and a C-terminal cleavage domain; and a second polypeptide of interest. The method can include cleaving the first polypeptide of interest from the first N-terminal autocatalytic cleavage domain. The method can include cleaving the second polypeptide of interest from the C-terminal cleavage domain, such that two separate polypeptides are produced, neither of which includes the processing unit. In some embodiments, neither polypeptide contains the entire processing unit. In some embodiments, neither polypeptide contains a portion of the processing unit. In some embodiments, one polypeptide contains a portion of the processing unit, while the other polypeptide does not contain any of the processing unit. In some embodiments, the N-terminal autocatalytic cleavage domain includes an intein, a B-type bacterial intein-like (BIL) domain, or a derivative thereof. In some embodiments, the N-terminal autocatalytic cleavage domain includes an intein configured to have no splicing activity, and to cleave at an N-terminal, but not C-terminal end of the intein. In some embodiments, cleaving the first polypeptide of interest includes hydrolyzing a peptide bond so that there is no amino acid overhang on a C terminus of the first polypeptide of interest. In some embodiments, the method is performed in a eukaryotic cell. In some embodiments, the first polypeptide is cleaved in a cellular location outside of the Golgi. In some embodiments, the C-terminal cleavage domain includes an intein. In some embodiments, the C-terminal cleavage domain includes a 2A sequence. In some embodiments, the 2A sequence is a non-viral 2A sequence. In some embodiments, the C-terminal cleavage domain includes at least one of SUMO or UB. In some embodiments, the second polypeptide of interest and at least a portion of the C-terminal cleavage domain are co-translationally cleaved from sequences upstream of the C-terminal cleavage domain. In some embodiments, cleaving the second polypeptide of interest includes hydrolyzing a peptide bond so that there is no amino acid overhang on an N terminus of the second polypeptide of interest. In some embodiments, the first polypeptide of interest and second polypeptide of interest are expressed stoichiometrically. In some embodiments, the polynucleotide encodes at least three polypeptides of interest, and a processing unit is positioned between each two consecutive polypeptides of interest. The method can include cleaving each of the at least three polypeptide of interest from a processing unit adjacent thereto. In some embodiments, the polynucleotide includes at least one of: nucleotides 837-1617 of SEQ ID NO: 6; nucleotides 760-1364 of SEQ ID NO: 8; nucleotides 760-1254 of SEQ ID NO: 10; nucleotides 760-1336 of SEQ ID NO: 12; nucleotides 760-1762 of SEQ ID NO: 14; nucleotides 769-1728 of SEQ ID NO: 16; nucleotides 831-1516 of SEQ ID NO: 18; or nucleotides 760-1245 of SEQ ID NO: 20. In some embodiments, the polynucleotide includes at least one of SEQ ID NO: 6, SEQ ID NO: 8, SEQ ID NO: 10, SEQ ID NO: 12, SEQ ID NO: 14, SEQ ID NO: 16, SEQ ID NO: 18; or SEQ ID NO: 20. In some embodiments, the polynucleotide encodes a polypeptide comprising at least one of positions 253-476 of SEQ ID NO: 9; positions 253-484 of SEQ ID NO: 11; positions 253-445 of SEQ ID NO: 13; positions 253-445 of SEQ ID NO: 15; positions 248-572 of SEQ ID NO: 17; positions 282-507 of SEQ ID NO: 19; or positions 253-524 of SEQ ID NO: 21. In some embodiments, initiating translation comprises at least transfecting, transforming, or transducing the cell with the single polynucleotide.

Some aspects include a single polynucleotide encoding, from 5' to 3', a first polypeptide of interest, a processing unit, and a second polypeptide of interest. The processing unit can include an N-terminal autocatalytic cleavage domain. The processing unit can include a C-terminal cleavage domain. In some embodiments, the N-terminal autocatalytic cleavage domain is configured to cleave a peptide bond between the N terminus of the N-terminal autocatalytic cleavage domain and the C terminus of the first polypeptide of interest so that there is no overhang on a C terminus of the first polypeptide of interest. In some embodiments, the C-terminal cleavage domain is configured to cleave a peptide bond between the C-terminal cleavage domain and the second polypeptide of interest. In some embodiments, the C-terminal cleavage domain is configured to cleave such that there are no overhanging amino acid residues on an N terminus of the second polypeptide of interest after cleaving the peptide bond.

In some embodiments, the C-terminal cleavage domain comprises a 2A sequence. In some embodiments, the 2A sequence includes at least one of a viral 2A sequence or a sea urchin 2A sequence. In some embodiments, the polynucleotide also encodes a linker of about 3-40 amino acids in length, and positioned between the N-terminal autocatalytic cleavage domain and the 2A sequence. In some embodiments, the C-terminal cleavage domain includes UB, SUMO, or a furin site positioned immediately upstream of an N terminus of the second polypeptide of interest. In some embodiments, the C-terminal cleavage domain includes an intein. In some embodiments, the C-terminal cleavage domain includes a UB, SUMO, or furin site positioned immediately upstream of an N terminus of the second polypeptide of interest. In some embodiments, the first polypeptide of interest includes a first subunit of a multimer, and the second polypeptide of interest includes a second subunit of the multimer. In some embodiments, the N-terminal autocatalytic cleavage domain includes an intein configured to have no splicing activity, and to cut at only the N terminal of the intein. In some embodiments, the N-terminal autocatalytic cleavage domain comprises SEQ ID NO: 28. In some embodiments, the C-terminal cleavage domain comprises a 2A sequence of SEQ ID NO: 5. In some embodiments, the C-terminal cleavage domain comprises an intein configured to have no splicing activity, and to cut at only the C terminal of the intein (and thus not at the N-terminal). In some embodiments, the C-terminal cleavage domain comprises SEQ ID NO: 29. In some embodiments, the polynucleotide also encodes a linker positioned downstream of the N-terminal autocatalytic cleavage domain, and upstream of the C-terminal cleavage domain, wherein the linker includes about 3-40 amino acid residues. In some embodiments, the polynucleotide includes at least one of: SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53. In some embodiments, the polynucleotide encodes a polypeptide comprising at least one of SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54. In some embodiments, the polynucleotide is integrated into a genome of a host cell, and wherein the host cell includes a eukaryotic cell. Some embodiments include a polypeptide encoded by the polynucleotide.

Some embodiments include a polynucleotide vector that comprises, from 5' to 3', a first multiple cloning site, a polynucleotide encoding a processing unit, and a second multiple cloning site. The processing unit can comprise an N-terminal autocatalytic cleavage domain. The processing unit can include a C-terminal cleavage domain. In some embodiments, the polynucleotide encoding the processing unit comprises one of SEQ ID NO: 39, SEQ ID NO: 41, SEQ ID NO: 43, SEQ ID NO: 45, SEQ ID NO: 47, SEQ ID NO: 49, SEQ ID NO: 51, or SEQ ID NO: 53. In some embodiments, the processing unit comprises one of SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54. In some embodiments, the polynucleotide vector further comprises a second processing unit, wherein the second processing unit is 3' and adjacent to the second multiple cloning site, and 5' and adjacent to a third multiple cloning site. In some embodiments, the polynucleotide vector further comprises a third processing unit, wherein the third processing unit is 3' and adjacent to the third multiple cloning site, and 5' and adjacent to a fourth multiple cloning site. In some embodiments, the polynucleotide vector further comprises a polynucleotide encoding a signal sequence. In some embodiments, the polynucleotide vector does not encode a peptide of interest.

BRIEF DESCRIPTION OF THE DRAWINGS

FIG. 1D schematically illustrates some embodiments in which a polynucleotide encodes one or more signal peptides for targeting one, or each polypeptide of interest to a cellular compartment.

FIG. 2 is a flow diagram illustrating methods of expressing at least two separate polypeptides.

FIG. 6A illustrates the Ssp DnaE Intein::FMDV 2A cassette sequence within the context of a cytosolic two-protein construct containing no signal peptide FIG. 6B illustrates a polynucleotide encoding a Ssp DnaE Intein::FMDV 2A cassette sequence within the context of a cytosolic two-protein construct containing no signal peptide.

Figure 7A:
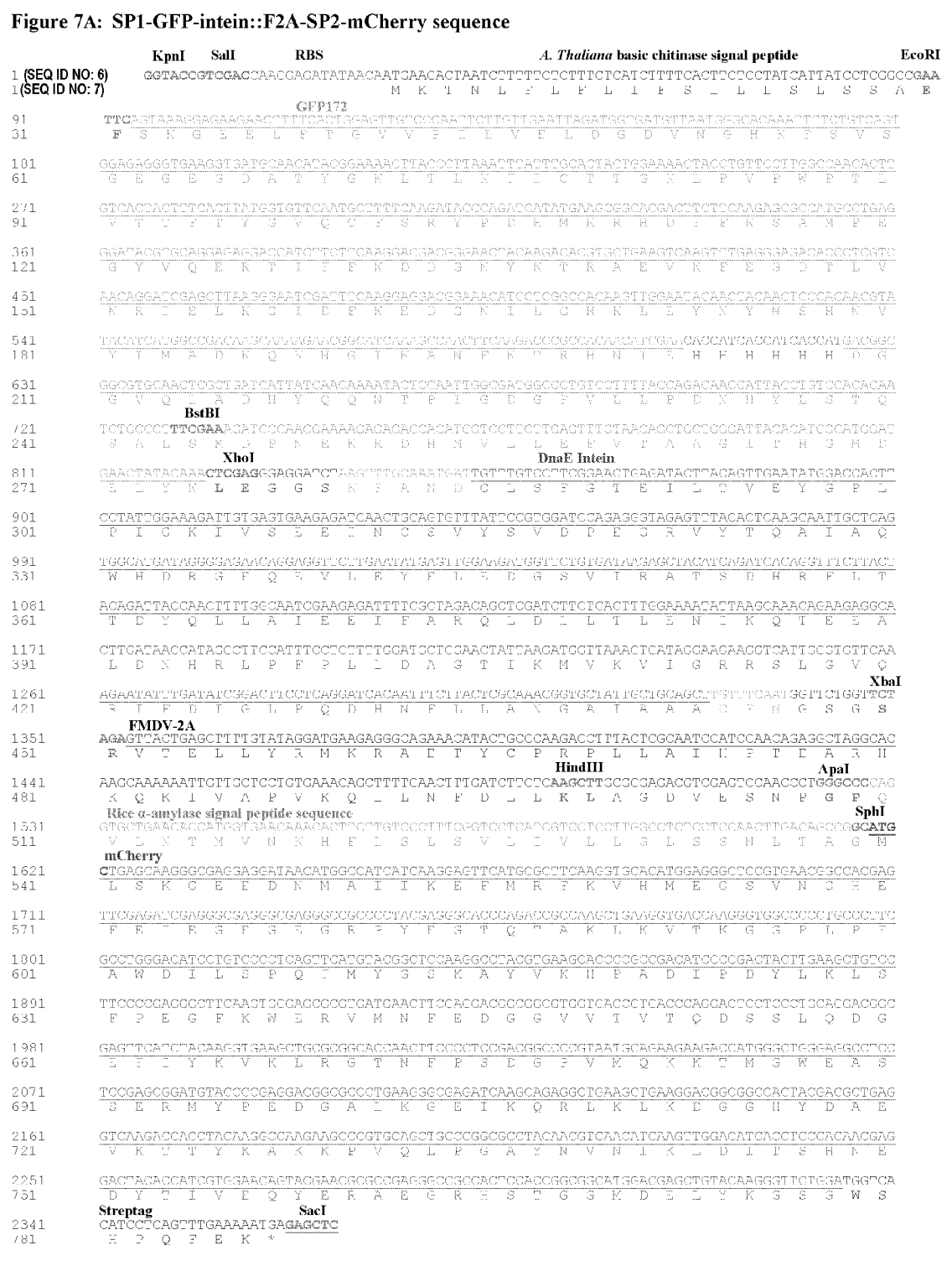

FIG. 7A illustrates the Ssp DnaE Intein::FMDV 2A cassette sequence within the context of a secretory two-protein construct containing two signal peptides FIG. 7B illustrates a polynucleotide encoding the Ssp DnaE Intein::FMDV 2A cassette sequence within the context of a secretory two-protein construct containing two signal peptide.

Figure 8A:
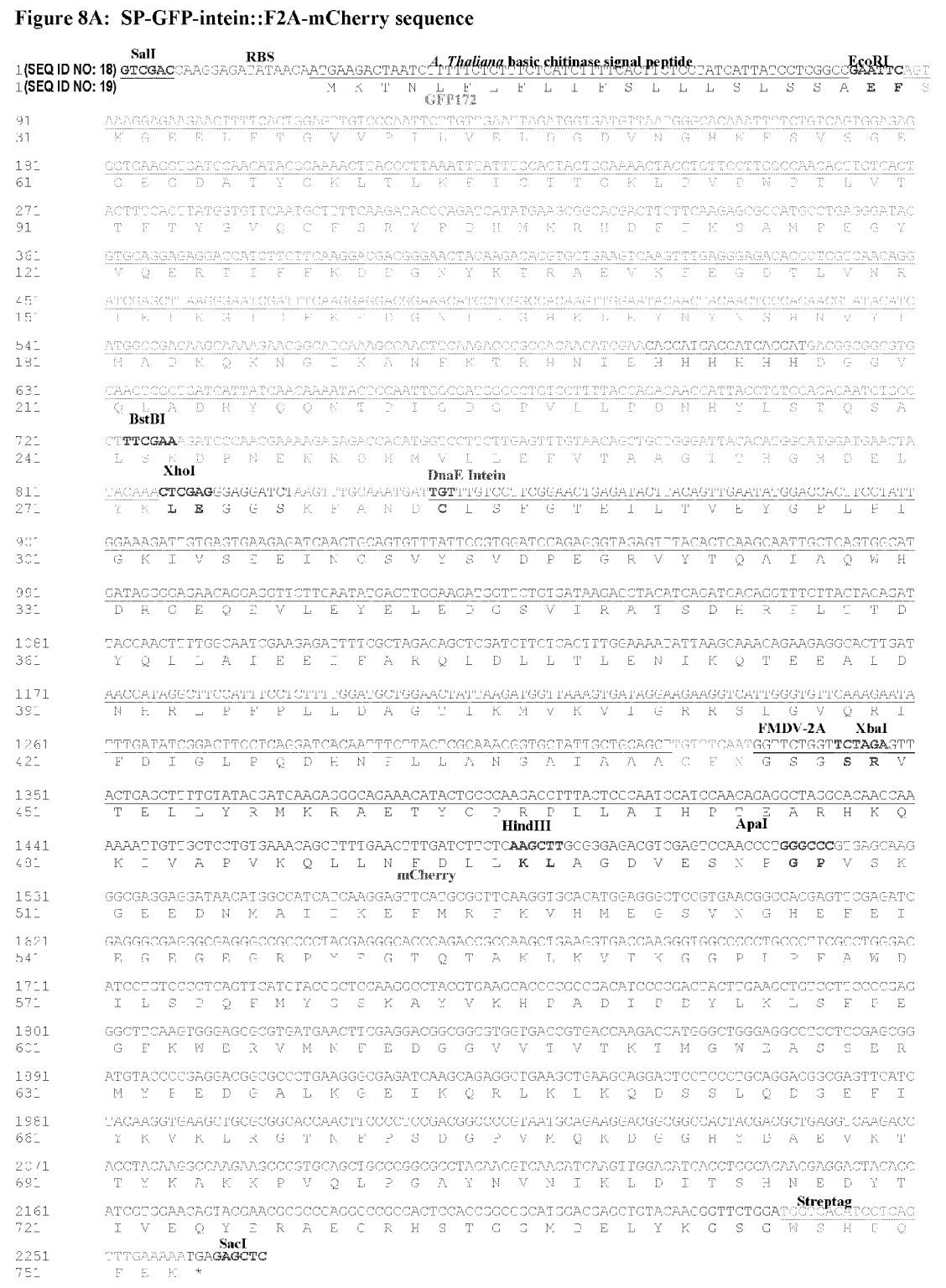

FIG. 8A: illustrates the Ssp DnaE Intein::FMDV 2A cassette sequence within the context of a secretory two-protein construct containing one signal peptide FIG. 8B: illustrates a polynucleotide encoding the Ssp DnaE Intein::FMDV 2A cassette sequence within the context of a secretory two-protein construct containing one signal peptide.

Figure 9A:
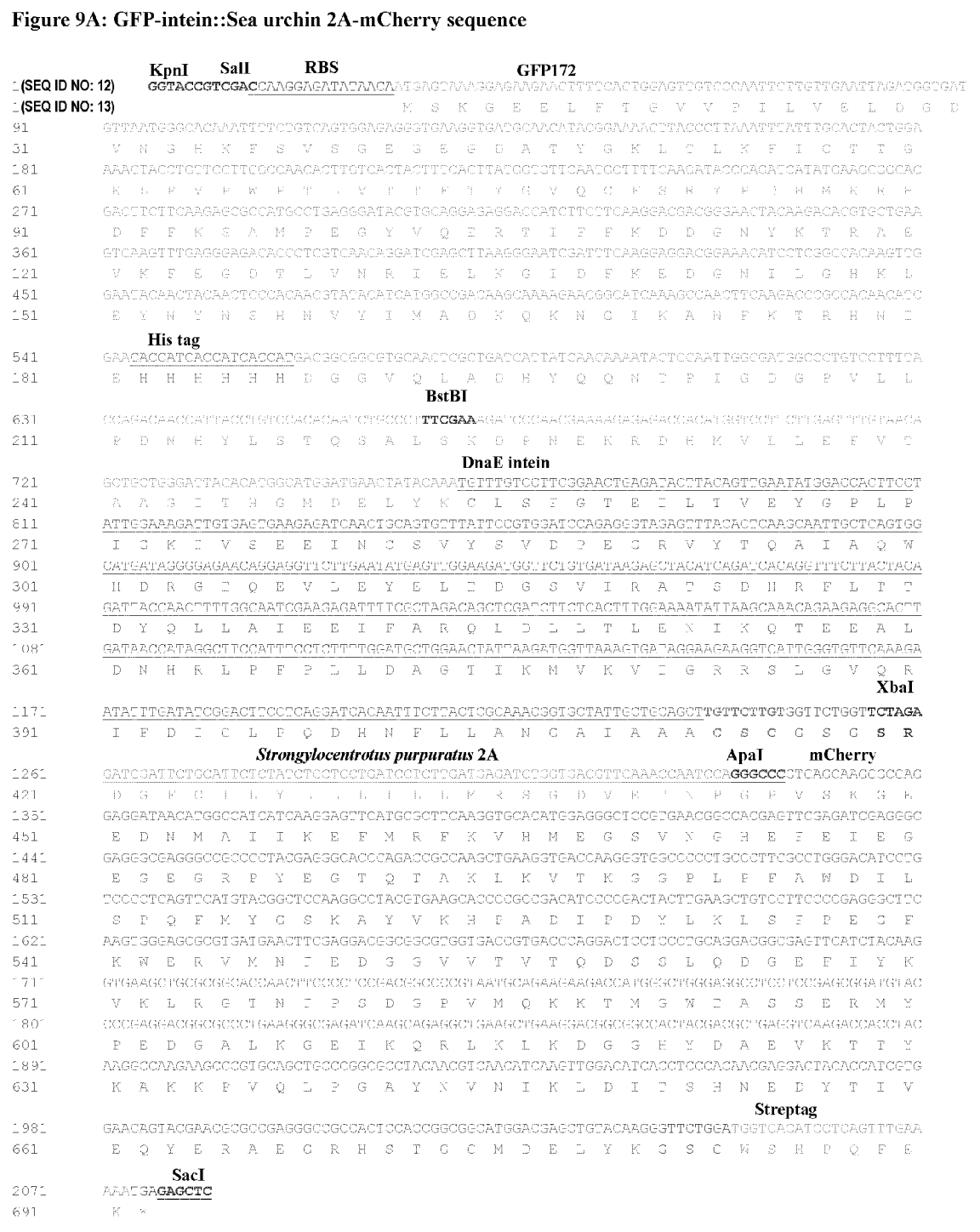

FIG. 9A illustrates the intein::Sea urchin 2A cassette sequence within the context of a cytosolic two-protein construct containing no signal peptide.

FIG. 9B illustrates a polynucleotide encoding intein::Sea urchin 2A cassette sequence within the context of a cytosolic two-protein construct containing no signal peptide.

FIG. 10A illustrates the Intein-Intein (Ssp DnaE intein-Ssp DnaB intein) cassette sequence within the context of a cytosolic two-protein construct containing no signal peptide.

FIG. 10B illustrates a polynucleotide encoding the Intein-Intein (Ssp DnaE intein-Ssp DnaB intein) cassette sequence within the context of a cytosolic two-protein construct containing no signal peptide.

FIG. 11A: illustrates the Intein-Intein (Ssp DnaE intein-Ssp DnaB intein) (inactive DnaE) cassette sequence within the context of a cytosolic two-protein construct containing no signal peptide.

FIG. 11B: illustrates a polynucleotide encoding the Intein-Intein (Ssp DnaE intein-Ssp DnaB intein) (inactive DnaE) cassette sequence within the context of a cytosolic two-protein construct containing no signal peptide.

Figure 12A:
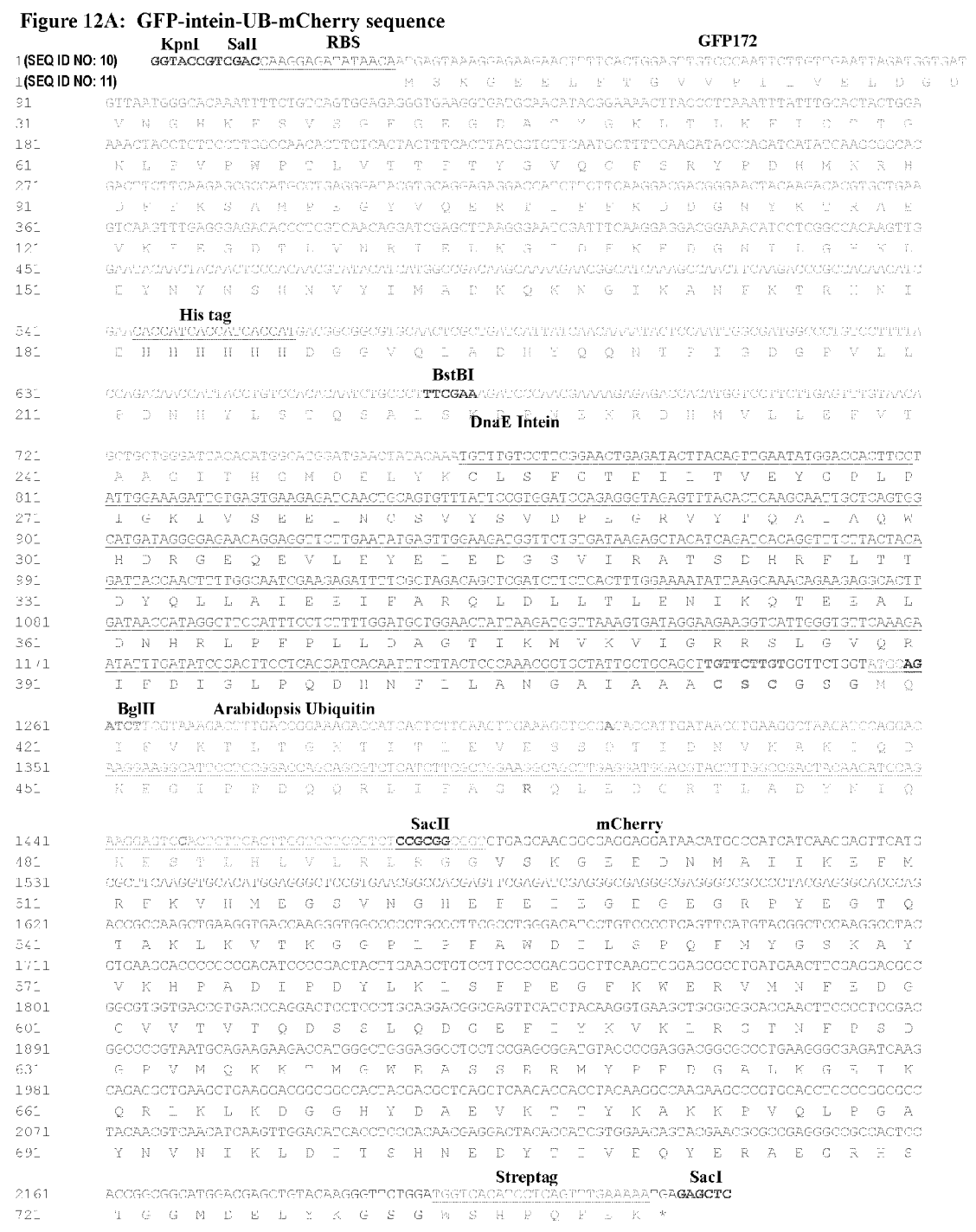

FIG. 12A illustrates the Intein-UB cassette sequence within the context of a cytosolic two-protein construct containing no signal peptide FIG. 12B illustrates a polynucleotide encoding the Intein-UB cassette sequence within the context of a cytosolic two-protein construct containing no signal peptide FIG. 13A illustrates the intein-SUMO cassette sequence within the context of a cytosolic two-protein construct containing no signal peptide.

Figure 13A:
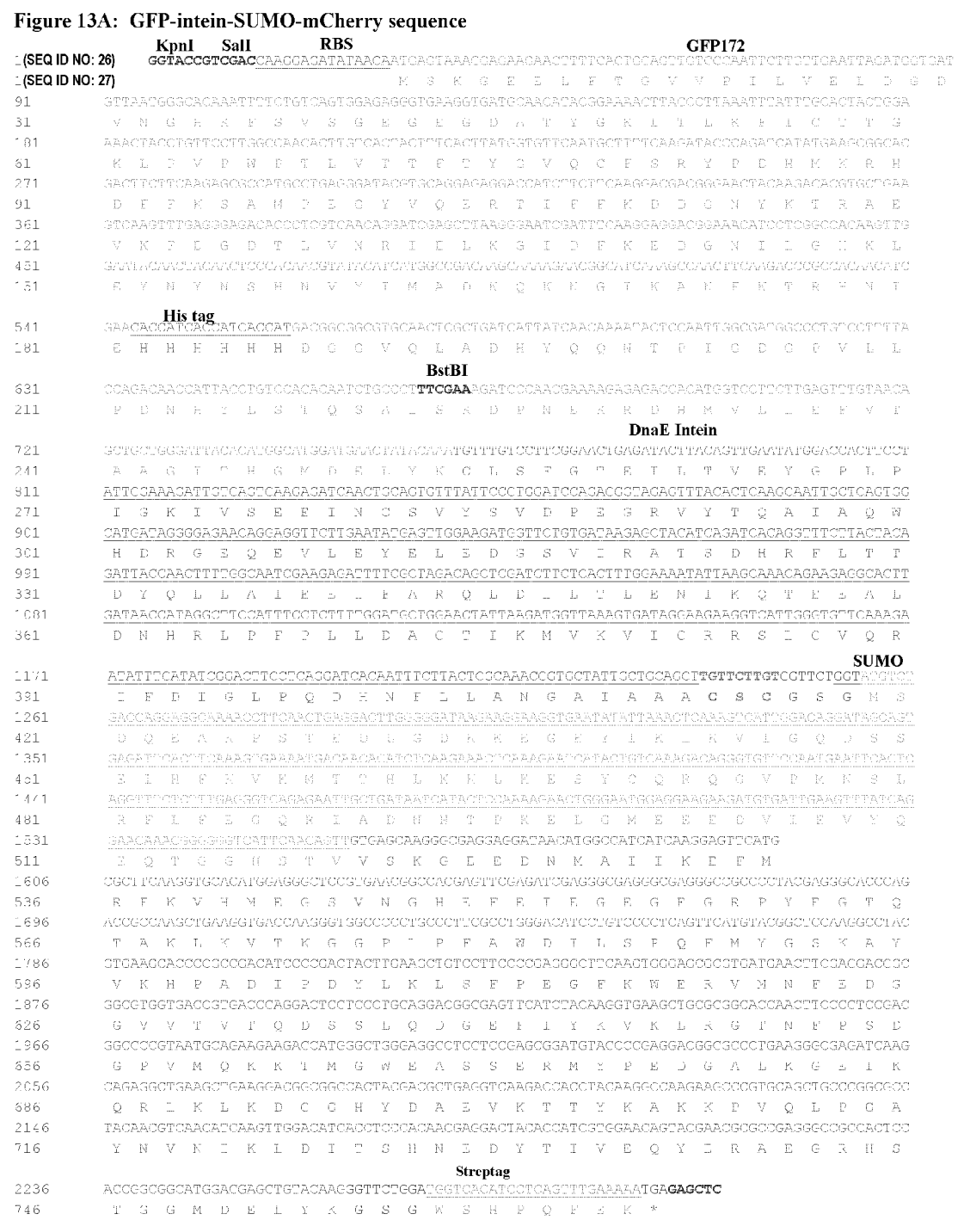

FIG. 13B illustrates a polynucleotide encoding the intein-SUMO cassette sequence within the context of a cytosolic two-protein construct containing no signal peptide.

Figure 14A:
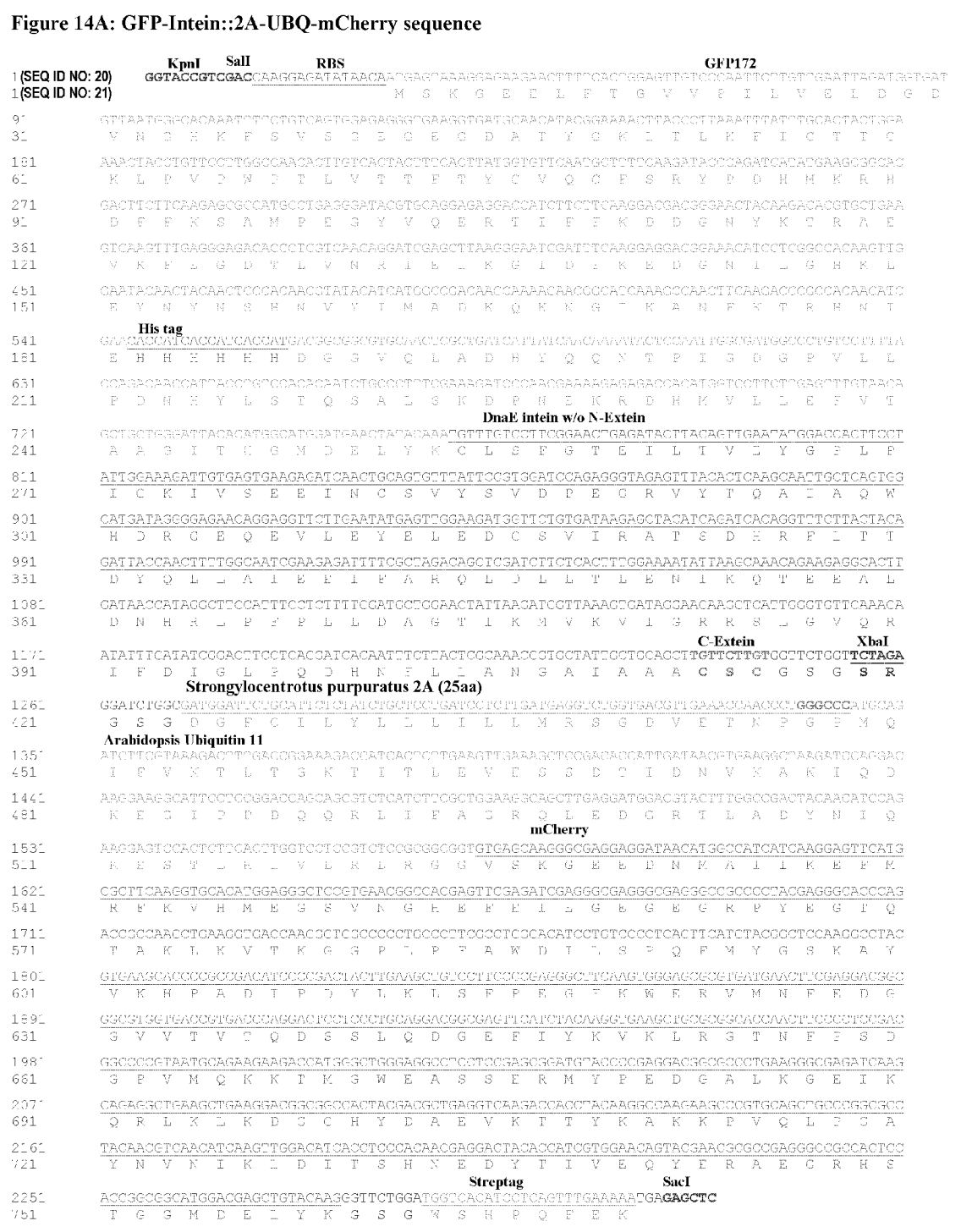

FIG. 14A illustrates the Intein::sea urchin 2A-UBQ cassette within the context of a cytosolic two-protein construct containing no signal peptide.

FIG. 14B illustrates a polynucleotide encoding the Intein::sea urchin 2A-UBQ cassette within the context of a cytosolic two-protein construct containing no signal peptide.

FIG. 16 illustrates western blot probed with anti-GFP (a), anti-streptag (b) & (d), and anti-Histag (c) antibodies.

FIG. 19 illustrates western blots illustrating the processing of intein::UBQ polyprotein in stably transformed tobacco NT1 cells and *N. benthamiana* leaf using (A) anti-GFP and (B) anti-streptag antibodies.

FIG. 25 illustrates (A) Validation of the split-GFP based in-vivo intein-activity assay: active intein gives fluorescence in *E. coli* (a), while no fluorescence is seen with inactive intein mutant (b). (B) GFP western blot analysis of mini-intein autocleavage mediated split GFP reconstitution using non-heat-denatured protein extracts.

DETAILED DESCRIPTION

Figure 1A:
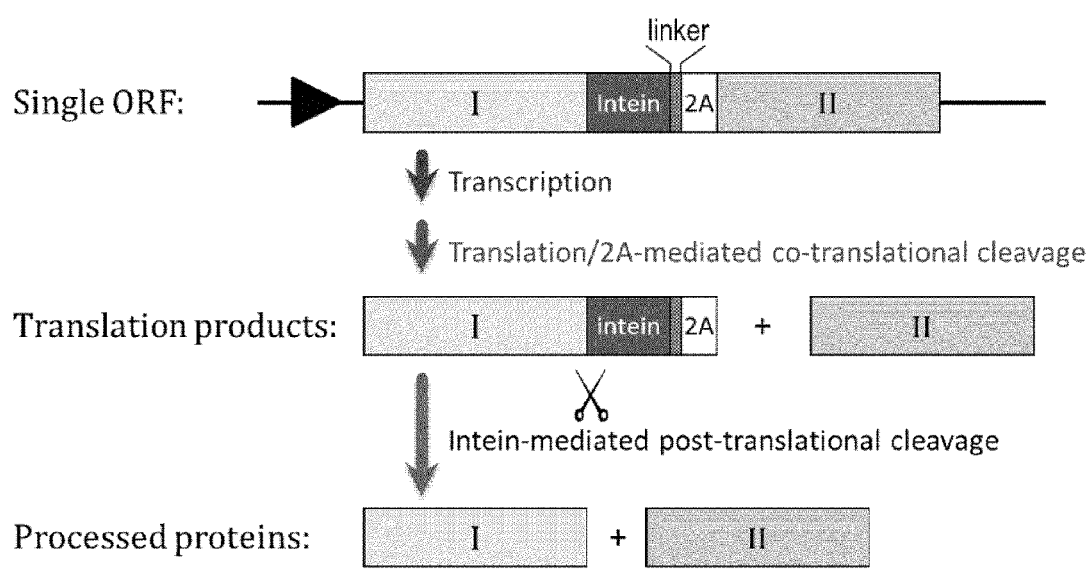
FIG. 1A schematically illustrates some embodiments in which a polynucleotide encodes an upstream polypeptide (I), an intein, a linker, a 2A sequence, and a downstream polypeptide (II).

It can be desirable to coordinate the expression of two or more polypeptides, for example two domains of a dimer of interest. Moreover, it can be desirable for expression to be carried out in a cell, in stoichiometric ratios, from a single Open Reading Frame (ORF), and/or so that polypeptides are expressed without overhanging N-terminal or C-terminal amino acid residues. Accordingly, some embodiments include expressing polynucleotides that encode at least two polypeptides of interest, and processing units for coordinating the cleavage of the polypeptides of interest from processing units, such that the cleavage can occur in vivo, in any cellular compartment (or in cell extracts or in an extracellular environment), from a single ORF, and/or in desired stoichiometric ratios. In some embodiments, a polynucleotide encodes a precursor polypeptide that includes a processing unit that includes at least two domains, and is positioned in-frame between an upstream polypeptide and a downstream polypeptide. Each of the two domains can mediate and/or facilitate a proteolytic event to cleave the upstream and downstream polypeptides from the moiety positioned in-between. In some embodiments, the processing unit includes an upstream N-terminal autocatalytic cleavage domain, and a downstream C-terminal cleavage domain. In some embodiments, the N-terminal autocatalytic cleavage domain includes an intein, a HINT domain, a hog domain, or a bacteria intein-like (BIL) domain. In some embodiments, the C-terminal cleavage domain includes at least one of an intein, a 2A sequence, UB, and/or SUMO. In come embodiments, when the polynucleotide is translated (either concurrently, or afterwards) the processing unit mediates and/or facilitate the cleavage of the polypeptides in a cell, without overhangs, in a variety of (or any) cellular compartment, and/or in desired stoichiometric ratios, while minimizing the size of the precursor polypeptide.

Unless expressly stated otherwise, each reference cited herein is hereby incorporated by reference in its entirety.

Polypeptide Expression

Multiple polypeptide expression, either in a cell, or in a cell-free system, can be useful for many applications, for example manufacturing of polypeptide products, such as enzymes, therapeutic biologics, for the generation of transgenic crops, for example crops with improved nutrient content, improved tolerance for adverse conditions, or for coordinated expression in living cells, for example making a transgenic organism with two or more transgenic traits, and/or for gene therapy. Some embodiments include methods and constructs for polypeptide expression. In some embodiments, a nucleic acid encoding a precursor polypeptide that includes, in cis, two or more polypeptides of interest is provided in an expression system. In some embodiments, the precursor polypeptide includes at least 2, for example 3, 4, 5, 6, 7, 8, 9, 10, 15, or 20 polypeptides of interest.

Polypeptide expression systems in living cells can be useful for many applications, for example large-scale and small-scale manufacturing of polypeptide products, for gene expression in transgenic organisms, for gene therapy in a patient, for the expression of markers, such as for research or diagnostic applications. Accordingly, some embodiments include expression of a nucleic acid encoding the precursor polypeptide in a living cell. In some embodiments, the cell is part of a multicellular organism.

Cell-free expression systems can be useful for small-scale and large scale manufacturing of polypeptide products, for assays such as disease models and in vitro diagnostics, and for research and screening applications. In some embodiments, two or more precursor polypeptides are expressed in a cell-free system. In some embodiments, a nucleic acid, for example a cDNA or an mRNA encoding a precursor polypeptide of interest is added to a cell-free expression system. The cell-free expression system can produce a polypeptide encoded by that nucleic acid. In some embodiments, a polypeptide is chemically synthesized, and added to a cell-free expression system. In some embodiments, expressed polypeptides are purified from a cell-free expression system.

As used herein, "upstream" means toward the N-terminus of an amino acid or toward the 5' end of a nucleotide sequence. As used herein, "downstream" means toward the C-terminus of an amino acid or toward the 3' end of a nucleotide sequence.

As used herein "cleave," "cleavage," and related terms refer to separating an upstream portion of a polypeptide from an adjacent downstream portion of a polypeptide. For example, cleavage can include hydrolysis of a peptide bond, thus separating sequences upstream and downstream of the peptide bond. For example, cleavage can include ribosome skipping, such as that performed by 2A and 2A-like sequences, so that an upstream portion of a nascent peptide is separated from a downstream portion of the nascent peptide encoded by the same transcript.

With reference to some embodiments herein, amino acids, or amino acid residues can be referred to by either a three-letter or a one-letter code. Twenty amino acids are typically encoded by the genetic code, and can be referred to using the following codes or abbreviations herein: Arginine ("Arg" or "R"), Histidine ("His" or "H"), Lysine ("Lys" or "K"), Aspartic Acid ("Asp" or "D"), Glutamic Acid ("Glu" or "E"), Serine ("Ser" or "S"), Threonine ("Thr" or "T"), Asparagine ("Asp" or "N"), Glutamine ("Gln" or "Q"), Cysteine ("Cys" or "C"), Glycine ("Gly" or "G"), Proline ("Pro" or "P"), Alanine ("Ala" or "A"), Valine ("Val" or "V"), Isoleucine ("Ile" or "I"), Leucine ("Leu" or "L"), Methionine ("Met" or "M"), Phenylalanine ("Phe" or "F"), Tyrosine ("Tyr" or "Y"), Tryptophan ("Trp" or "W").

With reference to some embodiments and description herein, the bases of nucleic acids, such as DNA, RNA, and the like can be referred to by either the name of the base or a one letter code. One skilled in the art will appreciate that the genetic code is degenerate, in that for some amino acid residues, two or more three-base codons can encode the same amino acid. Thus, for some of the polypeptides disclosed herein, two or more polynucleotides can encode these polypeptides. Thus, some one letter codes, and described herein, can represent one of two or more bases, for example to describe two or more possible nucleic acids that can encode a single amino acid. One-letter codes used herein include: "A" (adenine), "G" (guanine), "C" (cytosine), "T" (thymine), "R" (one of adenine or guanine), "Y" (one of cytosine or thymine), "M" (one of adenine or cytosine), "K" (one of guanine or thymine), "S" (one of cytosine or guanine), "W" (one of adenine or thymine), "H" (one of adenine, cytosine, or thymine), "B" (one of cytosine, guanine, or thymine), "V" (one of adenine, cytosine, or guanine), "D" (one of adenine, guanine, or thymine), and "N" (one of adenine, guanine, cytosine, or thymine).

Variants of a nucleic acid and polypeptide sequences disclosed herein can be generated using techniques known in the art, for example by random mutagenesis, site-directed mutagenesis, or chemical synthesis of a desired variant. In some embodiments, variants of the listed sequences are provided, in which each variant has a sequence that differs from a reference sequence by at least one nucleotide or amino acid residue. It is contemplated herein that a variant comprises a sequence having at least about 70% identity (nt-nt or aa-aa) to a reference sequence, for example at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.3%, 99.5%, 99.7%, 99.8%, 99.9%, or 99.99%, including ranges between any two of the listed values. Moreover, many variants can have substantially similar, or even superior functionality to a reference sequence. Accordingly, some embodiments include variants of the polynucleotide and polypeptide sequences disclosed herein.

"Modified" as used herein, includes a mutation in a polynucleotide or polypeptide sequence that differs from wild-type. Modifications can include point mutations, insertions, deletions, indels, and the like. Modifications can include in-frame, and out-of frame modifications to nucleic acids. Modified molecules, can, but do not necessarily, include at least one functionality in addition to the wild-type sequence, and/or lack at least one functionality possessed by the wild-type sequence.

Host Cell Systems

A variety of host cell systems can be used to co-express two or more polypeptides encoded by a single polynucleotide, for example microorganisms such as bacteria (e.g., *E. coli* or *B. subtilis*) transformed with expression vectors such as recombinant bacteriophage DNA, plasmid DNA or cosmid DNA expression vectors containing nucleotide sequences encoding the precursor polypeptide; yeast (e.g., *Saccharomyces, Pichia*) transformed with recombinant yeast expression vectors containing nucleotide sequences encoding the precursor polypeptide; insect cell systems infected with recombinant virus expression vectors (e.g., baculovirus) containing nucleic acids encoding the precursor polypeptide; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequences encoding the precursor polypeptide; or mammalian cell systems (e.g., COS, CHO, BHK, 293, 3T3) harboring recombinant expression constructs containing nucleotide sequences encoding the precursor polypeptide.

In some embodiments, the host cell system includes a eukaryotic cell. Eukaryotic cells can include single cell organisms, single cells of a multi-cell organism in cell culture, and whole organisms, for example a transgenic organism. In some embodiments, the eukaryotic cell is one of a yeast cell, an algae cell, a plant cell, for example a monocot cell or dicot cell, an insect cell, or a mammalian cell. Accordingly, in some embodiments, the host cell includes a cell in cell culture. Methods of cell culture are well known to those skilled in the art. In some embodiments, the host cell is part of a multicellular organism.

The co-expression of two or more polypeptides can be useful for many agricultural applications. Accordingly, in some embodiments, a polynucleotide encoding a precursor polypeptide is expressed in a plant cell. Methodology for transferring foreign genetic material plant cells are well known to one of skill in the art. For example, a method of transforming to tobacco plant cells, in which the transferred genes are incorporated into the tobacco plant cell genome via *Agrobacterium tumefaciens*, is described, for example, in Fisher et al. (1995) Plant Molecular Biology Reporter 13:279. In some embodiments, the transgenic plant expressing the precursor polypeptide is a mosaic. In some embodiments, the transgenic plant expression the precursor polypeptide is a derived from a single progenitor cell, or a plurality of progenitor cells, each of which contain a polynucleotide encoding the precursor polypeptide. Plants can be classified according to the number of cotyledons in the embryo, and traditionally have been classified as "monocots" (one cotyledon) or "dicots" (two cotyledon). Monocots and dicots each include many agriculturally important species. For example, monocots include grains such as maize, wheat, and rice, other food crops such as sugar cane, bamboos, bananas, and onions, and many flowering plants such as tulips, orchids, and daffodils. For example, dicots include tobacco, soybeans, tomatoes, and grapes. Some embodiments include expression of a polypeptide precursor in a monocot. Some embodiments include expression of a polypeptide precursor in a dicot.

The expression of polynucleotides encoding two or more polypeptides can be useful for many therapeutic and diagnostic applications. Therapeutic and diagnostic polypeptide products can be manufactured in mammalian cells, for example to facilitate folding and post-translational modification of these polypeptides. Accordingly, in some embodiments, a polynucleotide encoding two or more polypeptides is expressed in a mammalian cell, for example a COS, CHO, BHK, 293, or 3T3 cell. In some embodiments, a polynucleotide encoding the polypeptide precursor is transduced into a mammalian cell, for example via an adenoviral or lentiviral vector. In some embodiments, the mammalian cell is transfected with a plasmid containing a polynucleotide encoding the polypeptide. In some embodiments, a polynucleotide encoding the precursor polypeptide is stably integrated into the genome of a mammalian cell. In some embodiments, the mammalian cell with the stably integrated genomic polynucleotide is a germline cell, and is used to make a transgenic animal containing in its genome a stably integrated polynucleotide encoding the precursor polypeptide. The mammalian expression constructs can additionally contain promoters as described herein and known in the art, for example promoters derived from the genome of mammalian cells (e.g., metallothionein promoter) or from mammalian viruses (e.g., the adenovirus late promoter; the vaccinia virus 7.5K promoter).

In some embodiments, a nucleic acid encoding two or more polypeptides of interest is administered to a living organism, and a transcript encoding the polypeptides of interest in-frame to at least one processing unit is expressed in the living organism. In some embodiments, a precursor polypeptide is chemically synthesized, and administered to a living organism, for example a patient in need of a therapeutic. The precursor polypeptide can be synthesized by chemical synthesis methods (such as solid phase peptide synthesis) using techniques known in the art, such as those set forth by Merrifield et al., J. Am. Chem. Soc. 85:2149 (1964), Houghten et al., Proc. Natl. Acad. Sci. USA, 82:51:32 (1985), Stewart and Young (Solid phase peptide synthesis, Pierce Chem. Co., Rockford, Ill. (1984), and Creighton, 1983, Proteins: Structures and Molecular Principles, W. H. Freeman & Co., N.Y. hereby incorporated by reference in their entireties.

Expression Vectors:

Some embodiments include expression vectors. The expression vector can include a polynucleotide encoding two or more polypeptides as described herein. The expression vector can include a multiple cloning site. The multiple cloning site can include at least one restriction endonuclease cleavage site. The multiple cloning site can include a GATEWAY™ entry site (see, e.g. U.S. Pat. No. 7,393,632, hereby incorporated by reference in its entirety). Some embodiments include expression vectors that include a polynucleotide encoding at least one processing unit as described herein, and at least one multiple cloning site, for example so that one or more polynucleotides encoding desired polypeptides of interest can be cloned into the vector. Some embodiments include vectors encoding a cassette that encodes at least one processing unit, flanked on each side by a multiple cloning site. In some embodiments, the multiple cloning site is upstream of the processing unit. In some embodiments, the multiple cloning site is downstream of the processing unit. In some embodiments, a first multiple cloning site is upstream of the processing unit, and a second multiple cloning site is downstream of the processing unit. In some embodiments, the processing unit is positioned in-frame to the multiple cloning site, so that polypeptides of interest can be clone in-frame to the signal peptide. In some embodiments, one or more nucleic acids encoding a polypeptide of interest can be inserted into the vector and expressed along with a processing unit without additional cloning, processing, and/or mutagenesis steps. Some embodiments include vectors encoding a cassette that encodes at least one processing unit, flanked on each side by a sequence encoding a reporter polypeptide. Some embodiments include a polynucleotide encoding a cassette, in which the polynucleotide comprises at least one of SEQ ID NO: 39, SEQ ID NO: 41, SEQ ID NO: 43, SEQ ID NO: 45, SEQ ID NO: 47, SEQ ID NO: 49, or SEQ ID NO: 51. Some embodiments include a vector including at least one of the listed polynucleotides. In some embodiments, the polynucleotide encodes a polypeptide cassette comprising at least one of positions SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54.

A useful tool is an expression vector that can readily express two or more desired polypeptide sequences once polynucleotides encoding these polypeptide sequences are cloned into the vector. Accordingly, some embodiments include a polynucleotide vector that comprises one or more polynucleotides encoding a processing unit as described herein, and each of which is positioned next to at least one multiple cloning sites. In some embodiments, each polynucleotide encoding a processing unit is positioned between a pair of multiple cloning sites. In some embodiments, the polynucleotide encoding the processing unit is positioned adjacent to the multiple cloning sites. In some embodiments, the polynucleotide comprises at least one of SEQ ID NO: 39, SEQ ID NO: 41, SEQ ID NO: 43, SEQ ID NO: 45, SEQ ID NO: 47, SEQ ID NO: 49, or SEQ ID NO: 51. In some embodiments, the processing unit comprises at least one of SEQ ID NO: 40, SEQ ID NO: 42, SEQ ID NO: 44, SEQ ID NO: 46, SEQ ID NO: 48, SEQ ID NO: 50, SEQ ID NO: 52, or SEQ ID NO: 54.

In some embodiments, the vector includes a promoter. In some embodiments, the vector includes a selectable marker, for example an antibiotic resistance or drug resistance gene, or a visually selectable marker such as β-galactosidase or GFP. In some embodiments the vector includes an origin of replication. In some embodiments, the vector includes one or more sequences homologous to a host genomic DNA sequence, for example for integration into the host genome. In some embodiments, the vector includes a sequence encoding a signal peptide, signal patch, or the like. In some embodiments, the signal peptide or signal patch is positioned in-frame to the polynucleotide encoding the upstream polypeptide of interest (see, e.g. FIG. 1D, (i)). In some embodiments, the signal peptide or signal patch is positioned in-frame to the polynucleotide encoding the downstream polypeptide of interest (see, e.g. FIG. 1D, (iii)). In some embodiments, one the signal peptide or patch is positioned in-frame to the polynucleotide encoding the upstream polypeptide of interest, and another signal peptide or patch is positioned in-frame to the polynucleotide encoding the downstream polypeptide of interest (see, e.g. FIG. 1D, (ii)). In some embodiments, the signal peptides or patches for the upstream and downstream polypeptides of interest target each of these polypeptides of interest to the same cellular compartment (see, e.g. Example 1.5).

In some embodiments, the vector includes a plasmid. In some embodiments, the vector includes a viral vector, for example CaMV TMV, baculovirus, a retroviral, an adenoviral, or a lentiviral vector. In some embodiments, the vector includes bacteriophage, cosmid, an artificial chromosome (e.g. a BAC or YAC).

In some embodiments, the vector is in a host cell as described herein. In some embodiments, the vector is stably integrated into the genome of a host cell as described herein.

Some exemplary constructs are described in more detail below. Others will be apparent to those of skill in the art in view of the description herein.

Promoters:

A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription. In some embodiments, an endogenous promoter in a host cell controls the expression of a polynucleotide integrated into the host cell genome. In some embodiments, a polynucleotide vector includes a promoter for expression of a precursor polypeptide encoded therein. Exemplary promoters include the cytomegalovirus hCMV immediate early gene promoter, the early or late promoters of SV40 adenovirus, the alkaline phosphatase promoter, the promoters of the yeast alpha-mating factor promoter, and the Cauliflower Mosaic Virus 35S promoter.

It can be desirable to transcribe a polynucleotide encoding two or more polypeptides in a tissue-specific manner. Accordingly, in some embodiments, a tissue-specific promoter is provided. The tissue-specific promoter used can depend on the host cell used, and the desired expression activity. Exemplary promoters include, but are not limited to leaf-specific and light-induced promoters such as those from the Lhcb gene (Castresana et al. (1988) J. European Molecular Biology Organization. 7:1929 1936), the RbcS gene (Perisic and Lam (1992) The Plant Cell 4:831 838.), the psbD gene (Christopher et al. (1992) The Plant Cell 4:785 798), sequences from the legA major seed storage gene shown to regulate temporal protein expression (Shirsat et al. (1989) Mol Gen Genet. 215(2):326), or an alternate promoter in the *Arabidopsis thaliana* HMG1 gene (Lumbreras et al. (1995) Plant J., 8(4): 541).

Cis-regulatory elements can be used to further facilitate or fine-tune the expression of a polynucleotide. Cis-regulatory elements such as enhancers and insulators are well-known in the art, for example, for the octopine synthase enhancer element (Fromm, et al. (1989) Plant Cell 1(10):977). Additional cis-regulatory elements can be identified, for example by expression screening of a genomic library, and/or by computational analysis of a host genome. In some embodiments, tissue-specific and/or temporally specific enhancers are provided in cis to a polynucleotide encoding the precursor polypeptide in order to facilitate tissue-specific, and/or high-expression-level expression of the precursor polypeptide. In some embodiments. In some embodiments in which a polynucleotide encoding a precursor polypeptide are integrated in a host genome, insulator elements are provided in cis to a polynucleotide encoding the precursor polypeptide. The insulator elements can facilitate consistent expression levels of the precursor polypeptide independent of the site in the host genome the polynucleotide encoding the precursor polypeptide has integrated, for example in a heterochromatin environment.

Cleavage Domains

In general, "cleavage domains" can refer to polypeptide sequences that are cleaved either autocatalytically in cis, or by a catalytic molecule (for example an enzyme or ribozyme) in trans. Autocatalytic cleavage domains, as used herein refer to polypeptide sequences that are configured to cleave a polypeptide, in cis, at one or more positions either within, or upstream of the domain. Autocatalytic cleavage domains can include inteins, hog HINT domains, B-type BIL domains, 2A sequences, mutants and derivatives thereof and the like.

As used herein, "N-terminal autocatalytic cleavage domain" refers to autocatalytic domains that can cleave a moiety that includes an upstream (N-terminal) polypeptide sequence of interest, but does not include the processing unit. N-terminal autocatalytic cleavage domains can include, for example, inteins, mini-inteins, hog domains, BIL domains, and derivatives thereof as described herein.

As used herein, "C-terminal cleavage domain" refers to domains that facilitate the cleavage, either autocatalytically, by one or more enzymes in trans, or both autocatalytically and by one or more enzymes in trans, of a moiety that includes the downstream (C-terminal) polypeptide of interest, but does not include the entire processing unit. A C-terminal cleavage domain can include one or more of an intein, a 2A sequence, UB or SUMO, or a furin cleavage sequence.

Inteins

Inteins are found in nature, and can be involved in protein splicing processes that include a protein excising itself along with the concomitant ligation of the flanking protein sequences. The protein splicing elements is referred to as an "intein," while the flanking sequences are referred to as "exteins." Some embodiments include polynucleotides that encode one or more inteins.

Unless expressly stated otherwise, as used herein, "intein" refers to an auto-catalytic domain of the Hog/INTein (Hint) superfamily that splices itself out of a polypeptide by forming a peptide bond between two flanking polypeptides. Inteins include, but are not limited to DnaB helicase (dnaB) inteins, DNA polymerase III α subunit (dnaE) inteins, DNA polymerase III τ subunit (dnaX) inteins, RecA inteins, DNA gyrase subunit A inteins (gyrA), and DNA gyrase subunit B inteins (gyrB), including functional and mutants and modifications thereof, such as mini-inteins, n-terminal and/or c-terminal mustants, and the like. Additional information regarding inteins and their characteristics can be found on the world wide web at bioinfo.weizmann.ac.il/~pietro/Hints/. Unless explicitly stated otherwise, as used herein "intein" includes naturally-occurring inteins, or functional mutants or variants thereof, including engineered and synthetic inteins.

While inteins are known to vary in length and sequence, a feature characteristic of many inteins is a Ser (S) or Cys (C) on the N terminus, and a C terminal motif of either His-Asn-Cys (HNC) or His-Asn-Ser (HNS), and some of these N and C terminal motifs have been shown to function in splicing and/or cleavage activity of the intein. In some embodiments, one or more amino acid residues near the N terminus or C terminus of the intein are mutated to reduce or eliminate splicing activity. In some embodiments, one or more amino acid residues near the N terminus or C terminus of the intein are modified such that N terminal cleavage, and/or C terminal cleavage is increased.

In some embodiments, the intein is the Ssp DnaE intein (SEQ ID NO: 1). In some embodiments, the intein is the Npu DnaE intein. Modifying the most C-terminal residue of an intein, for example the Asn 159 residue of the Ssp DnaE intein (SEQ ID NO: 1) eliminates splicing activity of the intein and C terminal cleavage, while preserving the intein's N-terminal cleavage activity (Amitai, et al. (2009) Proc. Nat. Acad. Sci. USA 106: 11005-10)(Martin, et al (2001) Biochemistry 40: 1393-402). Mutating the most N-terminal residue of an intein, for example the Cys1 residue of the Ssp DnaE intein, eliminates splicing activity and N terminal cleavage while preserving the intein's C terminal cleavage.

Accordingly, in some embodiments, for example when cleavage of a polypeptide in cis to the N terminus of the intein is desired, the intein contains a mutation that inhibits splicing by the intein, while permitting cleaving at the N terminus. In some embodiments, the mutation is of the most C-terminal amino acid residue of the intein. In some embodiments, the mutation is an Asn→Ala mutation, for example the N159A mutation in the Ssp DnaE intein, or a mutation that otherwise mutates the most C terminal residue of the intein so as to inhibit splicing and C terminal cleavage.

In some embodiments, for example when cleavage of a polypeptide in cis to the C terminus of the intein is desired, the intein contains a mutation that inhibits splicing by the intein, while permitting cleaving at the C terminus of the intein. In some embodiments, the mutation is of the most N-terminal amino acid residue of the intein. In some embodiments, the mutation is an Cys→Ala mutation, for example the C1A mutation in the Ssp DnaE intein, or a mutation that otherwise mutates the most N terminal residue of the intein so as to inhibit splicing and N terminal cleavage.

For the Ssp DnaE intein, in both the linear and branched intermediates, the hydrolysis of the ester bond between the N-extein and the intein/C-extein can mediate the release of the N-extein. Furthermore, the amino acids Ser and His are known to function together as a catalytic dyad in the active sites of diverse enzymes, including, for example serine protease, lipase, and esterase, and that in some instances, a Ser-His dipeptide itself can cleave ester compounds, for example p-nitrophenyl acetate (Li et al. (2000), Bioorg Med Chem 8: 2675-80). In the Ssp DnaE mini-intein, the C-terminal Asn159 residue is near the His 147 residue, which has been shown to activate the side chain $N^\delta$ atom of Asn159 and facilitate the splicing reaction. Thus, it is contemplated herein that an N159S mutation can interact with the His147 residue to form a catalytic dyad, and that the proximity of both residue to the ester bond linking the N-extein to the native intein/C-extein junction may further accelerate the cleavage of the ester bond to release the N extein. Thus, some embodiments include an N159S mutation in the DnaE mini-intein. Some embodiments include a mutation at the C terminal of an intein, to introduce a His, Ser, or His and Ser near the position of the ester bond linking the N extein to the intein/C-extein junction during native splicing and excision of the intein. Without being limited to any theory, such mutations can increase the efficiency of N extein cleavage.

Modifying certain extein residues can also affect the splicing and/or cleavage activity of an intein. For example, mutation of the N-extein N-2 and N-1 (i.e. the two most C-terminal residues of the N-extein), and the C-extein C+1 residue (i.e. the most N terminal residue of the C-extein) has been shown to accelerate N-extein cleavage, while attenuating protein splicing for the Ssp DnaE mini-intein (Amitai et al (2000) Proc. Nat. Acad. Sci. USA 106: 11005-10)(Martin, et al (2001) Biochemistry 40: 1393-402). Exemplary modifications shown to increase N-extein cleavage, while attenuating protein splicing include: modifications of the N-2 and N-1 extein residue to one of: n-ND or n-RD; modifications of the C-extein C+2 and C+3 residues to one of c-SC, c-LC, c-SR, and c-RA; and modifications of the N-extein N-1, N-2, and C-extein C+2 and C+3 residues to one of nc-GG/TP, nc=EN/LC, nc-JD/LA, nc-GN/LS, and nc-ED/FN. Some embodiments include one of the listed N-extein N-2 and N-1 residue modifications (e.g. n-ND or n-RD). Some embodiments include one of the listed C-extein C+2 and C+3 residue mutations (e.g. c-SC, c-LC, c-SR, and c-RA). Some embodiments include one of the listed N-extein N-2 and N-1 residue modifications and one of the listed C-extein C+2 and C+3 residue modifications (e.g. one of n-ND or n-RD, and one of c-SC, c-LC, c-SR, and c-RA). Some embodiments include one of the listed N-extein N-1, N-2, and C-extein C+2 and C+3 pairs (e.g. one of nc-GG/TP, nc=EN/LC, nc-JD/LA, nc-GN/LS, or nc-ED/FN).

It can be desirable to minimize the size of an intein. Without being bound by any one theory, as discussed herein, previous efforts to include an NIa protease target domain (which can be 27-48 kD in size) between two polypeptides of interest can be complicated by unfavorable folding, which can lead to low polypeptide yield, or improper polypeptide function. Additionally, the Pol I intein is very large (460 amino acids, over 50 kD), and the self-cleavage occurs entirely post protein translation. Accordingly, some embodiments include an intein of minimal size, such as a mini-intein. It has been shown, for example that up to 45 amino acids residues (amino acids 79-123) can be removed from the C-terminus of the Ssp DnaE Int-n intein fragment, and yet this fragment is still function in the protein trans-splicing process in both dicot and monocot plants (Yang et al (2006) Transgenic Res. 15: 583-93). Accordingly, some embodiments include an Ssp DnaE "mini-intein," for example, in which amino acids 79-123 have been removed from the wild-type intein. Some embodiments include a "mini-intein," that retains protein cleavage function of the intein it is derived from, and contains at least about 5% fewer amino acid residues than the intein it is derived from, for example at least about 5%, 10%, 15%, 20%, 25%, 30%, 40%, 45%, 50%, 55%, 60%, 65%, 70%, 75%, or 80% fewer amino acid residues. In some embodiments, a mini-intein includes a minimal HINT domain. Some embodiments include two or more mini-inteins. In some embodiments, a mini-intein is further modified, for example at the C terminus or N terminus as taught herein.

In addition to inteins, other HINT-domain superfamily member can perform autocatalytic cleavage, for example hog HINT domains, bacterial intein-like domains (BIL), 2A sequences, mutants and derivatives thereof and the like. Hog domains are found in hedgehog proteins, and can catalyze cleavage of an upstream (N-terminal) domain by attaching a cholesterol molecule to this domain (Mann, R. K., Beachy, P. A. (2004) *Annu Rev Biochem* 73, 891-923). B-type BIL domains can cleave at either their N' or C' termini, while A-type BIL domains can cleave at either their N' or C' termini and perform protein splicing (Dassa, B., Haviv, H., Amitai, G., Pietrokovski, S. (2004). J Biol Chem published online ahead of print as doi:10.1074/jbc.M404562200; Dassa et al (2004). TRENDS in Genetics 20: 538-542, hereby incorporated by reference in its entirety). Accordingly some embodiments include at least one of a HINT domain, a hog domain, a B-type BIL domain, or an A-type BIL domain. In some embodiments, the A-type BIL domain includes a mutation to eliminate or reduce its splicing activity.

C-Terminal Cleavage Domains

Other cleavable and/or cleavage-mediating domains can be provided alone, in combination, or in combination with an N-terminal autocatalytic cleavage domain in cis, to obtain or enhance desired cleavage activity of a precursor polypeptide. In some embodiments, a polynucleotide includes at least one of these additional cleavable and/or cleavage mediating domains.

Ubiquitin (UB) is a small, highly stable and conserved protein in eukaryotes. UB can function in selective protein degradation. The UB monomer is a small protein and exists in nature as a protein fusion, either as a poly-UB or as an UB attached to the N-terminus of an unrelated protein. Expression of target proteins as UB fusion (typically UB is at the N terminal) has been shown to improve target protein accumulation in bacteria, yeast, plant, and mammalian hosts. In eukaryotic hosts, UB fusion proteins are efficiently cleaved in a cell at the C-terminus of UB to create downstream protein with its native N-terminus. The cleavage is achieved via deubiquitinating enzymes (DUBs; sometimes refer to as UB-specific proteases or UB C-terminal hydrolases). Although a UB-based vector has been reported for co-expression of multiple proteins in plants (Walker, J. M., and R. D. Vierstra (2007). *Plant Biotechnol J* 5:413-21.), such approach leaves behind six or more amino acid overhang at the C-terminus of the polypeptide fused upstream of the UB moiety, and may cause undesirable effects.

The Small UB-like MOdifier (SUMO) is similar to UB in many respects but not involved in selective protein degradation. Instead, SUMO is involved in the SUMOylation process in which it covalently modifies a large number of cellular proteins as a part of an elaborate regulatory mechanism for biological function and localization. Like UB, SUMO fusion has also been found useful in improving foreign protein accumulation in a variety of hosts. In plant and mammalian cells, the SUMO moiety is efficiently separated in vivo from its fusion partner by the SUMO-specific proteases (SENPs) and produces downstream protein with its native N-terminus. In some embodiments, for example, embodiments in which a downstream polypeptide is desired with no N-terminal overhanging amino acids, a UB polypeptide sequence or SUMO polypeptide sequence is positioned immediately upstream of the N terminus of the downstream polypeptide. Some embodiments include UB (MQIFVKTLTGKTITLEVESS-DTIDNVKAKIQDKEGIPPDQQRLIF-AGRQLEDGRTLAD YNIQKESTLHLVLRLRGG) (SEQ ID NO: 2). Some embodiments include SUMO (GSMS-DQEAKPSTEDLGDKKEGEY-IKLKVIGQDSSEIHFKVKMTTHLKKLKESYCQR QGVPMNSLRFLFEGQRIADNHTPKELG-MEEEDVIEVYQEQTGGHSTV) (SEQ ID NO: 3). Unless explicitly stated otherwise, "UB sequence" and "SUMO sequence" as used herein includes functional variants of these stated sequences. In some embodiments, a functional variant of UB or SUMO includes a polypeptide with at least about 70% identity to *N. tabacum* UB or *N. tabacum* SUMO, for example at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% identity.

Furin is a protease found in the trans-golgi apparatus. Furin recognizes, and cleaves polypeptides immediately downstream (i.e. immediately following the C terminus of) of the consensus sequence Arg-X-X-Arg (SEQ ID NO: 22), in which X is any amino acid residue. However, Furin prefers the sequence Arg-X-(Lys/Arg)-Arg (SEQ ID NO: 23). Furin can thus cleave an upstream moiety (having a furin cleavage sequence) from the N terminus of a downstream peptide without leaving any overhang, provided the downstream peptide is targeted to the secretory pathway. Thus, some embodiments include a furin cleavage sequence. The furin cleavage sequence can be positioned immediately upstream of the N terminus of a downstream polypeptide.

"CHYSEL" (cis-acting hydrolase element) peptides such as the foot and mouth disease virus (FMDV) 2A sequence (GSGSRVTELLYRMKRAETY-CPRPLLAIHPTEARHKQKIVAPVKQLLN-FDLLKLAGDV ESNPGP) (SEQ ID NO: 4), a picornavirus 2A-like sequence, and non-viral 2A-like sequence have polypeptide cleavage activity. As used herein "F2A" can also be used to refer to a FMDV 2A sequence. Some embodiments include a polynucleotide encoding one or more of the following CHYSEL peptides. A polypeptide of approximately 20 amino acids of the FMDV 2A region mediates cleavage of its own C terminus and releases itself from the adjoining peptide. 2A domains and 2A-like domains can mediate a ribosomal skipping mechanism that permits co-translational cleavage of a peptide containing the 2A or 2A-like domain from upstream sequences. Accordingly, in some embodiments precursor polypeptides that include a 2A sequence are cleaved co-translationally before the entire polypeptide is expressed. This option is acknowledged herein, but for simplicity, in some portions of this disclosure, 2A polypeptide sequences, or precursor polypeptides that contain 2A may be depicted, with the understanding that these polypeptides will be co-translationally cleaved into two or more polypeptides. Additionally, no sequences outside of the 2A region are believed to be required for 2A-mediated cleavage. However, 2A-mediated cleavage leaves the 2A peptide on the C terminus of the upstream peptide (N terminal moiety), and a single proline on the N terminus of the downstream (C terminal moiety). Previously, it has been reported that the 2A overhang may not interfere with protein accumulation in the cytosol, but that when the 2A-overhang-containing polypeptide is intended for the secretory pathway (e.g. when the polypeptide includes an ER-targeting signal), the 2A overhand causes mistargeting of the processed protein to the lytic vacuoles for degradation (El Amrani, et al. (2004) Plant Physiol. 135:16-24; Francois, et al. (2004) Plant Science 166:113-121; Samlova, et al. (2006), Traffic 7:1701-23). Some embodiments include a 2A sequence. In some embodiments, the 2A sequence is viral. In some embodiments, the 2A sequence is a FMDV 2A sequence. In some embodiments, the 2A sequence is a picornavirus 2A-like sequence. In some embodiments, the 2A sequence is non-viral. In some embodiments, the 2A sequence is a sea urchin (*Strongylocentrotus purpuratus*) 2A sequence (DGFCILYLLLILLMRSGDVETNPGP) (SEQ ID NO: 5); Sponge (*Amphimedon queenslandica*) 2A sequence (SEQ ID NO: 33 or SEQ ID NO: 34); acorn worm (*Saccoglossus kowalevskii*) (SEQ ID NO: 35) 2A sequence; or amphioxus (*Branchiostoma floridae*) (SEQ ID NO: 36 or SEQ ID NO: 37) 2A sequence. In some embodiments, the 2A sequence is a naturally occurring or synthetic sequence that includes the 2A consensus sequence D-X-E-X-NPGP (SEQ ID NO: 38), in which X is any amino acid residue.

It can be desirable to mediate co-translational processing of a precursor polypeptide. For example, to facilitate proper protein folding, post-translational modification, and/or desired subcellular localization, it can be desirable to co-translationally cleave an N terminal polypeptide. Accordingly, in some embodiments, a 2A sequence is positioned between an upstream and downstream polypeptide of interest. It can further be desirable for the downstream peptide to not have any overhanging N terminal amino acids following cleavage by the 2A domain. Thus, in some embodiments, additional cleavage-mediating domains can be positioned downstream of the 2A sequence, and immediately upstream of the N terminus of downstream polypeptide. In some embodiments, a UB or SUMO sequence is positioned in cis to the 2A and downstream polypeptide sequence of interest. The UB or SUMO sequence can be downstream of the 2A sequence and immediately upstream of the N terminus of the downstream polypeptide of interest. Thus, a DUB or SENP can cleave any overhanging amino acid residues (such as proline) from the N terminus. Since DUBS and SENPs can be found in substantially any cellular compartment, the overhanging amino acid residues can be cleaved from the N terminus of the downstream polypeptide in substantially any cellular compartment.

Additionally, protease sites that are known to one skilled in the art can be used in some embodiments. For example, the plant kex2p-like protease is a type I integral membrane endopeptidase that resides in the trans-Golgi network. Tobacco cells have been shown to have kex2p activity. In some embodiments, for example embodiments in which polypeptides of interest are destined for the secretory pathway, the polynucleotide encodes at least one kex2p target site positioned in-frame between a pair of polypeptides of interest. In some embodiments, at least two copies of the kex2p-target site are encoded in tandem, for example at least two, three, four, five, six, seven, eight, nine, or ten copies.

Linkers

Some embodiments include linkers between the N-terminal autocatalytic cleavage domain and C-terminal cleavage domain. Some embodiments include polynucleotides encoding linkers. Linkers can include peptide sequences that link an N-terminal autocatalytic cleavage domain or portion thereof to a C-terminal cleavage domain or portion thereof in a polypeptide.

It has been shown that ribosome skipping mediated by 2A is affected by the carboxyl terminal region of its upstream protein, including the length of the sequence immediately upstream of 2A (de Felipe et al. (2010) Biotechnol. J. 5: 213-23). Thus, it is contemplated herein that a peptide linker upstream of the 2A sequence can be engineered to give further improvements of activity. Accordingly, some embodiments include a polypeptide linker immediately upstream of 2A. Some embodiments include a native 2A linker such as the FMDV 2A linker. Some embodiments include a Gly/Ser-type flexible linker. Some embodiments include a rigid helical linker. Some embodiments include two or more of the above linkers. In some embodiments, the linker includes a multimer of sequences in tandem, for example a least 2, 3, 4, 5, 6, 7, 8, 9, 10, 15, or 20 copies of the sequence in tandem.

In some embodiments, the linker length is varied and selected to improve efficiency. In some embodiments, the linker is at least about 3 amino acid residues in length, for example at least about 3, 4, 5, 6, 7, 8, 9, 10, 11, 12, 13, 14, 15, 17, 20, 25, 30, 35, 40, 45, 50, 55, 60, 65, 70, 75, 80, 85, 90, 95, 100, 120, 150, or 200 amino acid residues in length. In some embodiments the linker has a length of about 3-5 amino acid residues, 3-7, 3-8, 3-10, 3-12, 3-15, 3-20, 3-25, 3-30, 3-35, 3-40, 3-45, 3-50, 3-60, 4-7, 4-8, 4-10, 4-12, 4-15, 4-20, 4-25, 4-30, 4-45, 4-50, 4-60, 5-8, 5-10, 5-12, 5-15, 5-20, 5-25, 5-30, 7-15, 7-20, 7-25, 7-30, 7-35, 7-40, 7-45, 7-50, 70-60, 10-20, 10-25, 10-30, 10-35, 10-40, 10-45, 10-50, 10-55, 10-60, 15-20, 15-25, 15-30, 15-35, 5-40, 15-45, 15-50, 15-60, 20-30, 20-35, 20-40, 20-45, 20-50, 20-60, 25-35, 25-40, 25-45, 25-50, 25-60, 25-70, 30-40, 30-50, 30-60, 40-50, 40-60, 40-70, 50-60, 50-70, 50-80, 60-70, 60-80, 60-90, 70-80, 80-90, 90-100, 70-100, 80-120, 90-120, 100-150, or 100-200 amino acid residues.

Constructs

A single intein can mediate cleavage of sequences on both the N terminal and C terminal of the intein, as well as the splicing of flanking protein sequences. However, single inteins mediate cleavage and splicing with low efficiency, may only cleave one of two flanking exteins, and/or can leave a large amount of uncleaved precursor polypeptide. Additionally, while cleavage at the N terminus of an intein is generally efficient, cleavage at the C terminus of a single-intein construct can be very inefficient. For example, it has been reported that the PolI intein from *Pyrococcus horikoshii* was inserted in frame with antibody heavy and light chains to achieve expression of these proteins encoded in a single polypeptide precursor in mammalian cells (Kunes et al. (2009), Biotechol Prog 25: 735-44). In the disclosure of Kunes et al., the C+1 extein Ser residue was mutated to a different residue, such as alanine, glycine, or methionine.

While some assembled antibody was detected in this study, no antibody was detected when the signal sequence was removed from the light chain of the antibody, which was the downstream peptide in the construct. Thus, it can be concluded that in this example, it was cleavage of the signal sequence of the light chain that cleaved the light chain from the intein moiety, rather than the intein itself. Without being bound by any one theory, mutations of the C+1 extein residue apparently attenuates both cleavage and splicing activity of intein, and it can further be concluded that C-terminal cleavage of the PolI intein was very inefficient. Accordingly, based on this disclosure, a PolI intein in combination with the C+1 extein residue would not provide a robust system for (a) cleavage of an intein moiety from the C terminal polypeptide of interest outside the Golgi apparatus, (b) cleavage of an intein moiety from the C terminal polypeptide of interest without C terminal overhang on the polypeptide of interest, or (c) robust, high-frequency cleavage of the C terminal polypeptide of interest from the intein. Consequently, single intein constructs can be inefficient for polypeptide synthesis or manufacturing applications. Moreover, without being bound by any one theory, dimerization of uncleaved precursor peptide with polypeptides that have been cleaved can impair the function of these peptides, resulting in a dominant negative-type effect.

Surprisingly, it has been found that a precursor polypeptide that includes, in cis, an upstream polypeptide, an N-terminal autocatalytic cleavage domain, a C-terminal cleavage domain, and a downstream polypeptide of interest can cleave the C terminus of the upstream polypeptide and N terminus of the downstream polypeptide with very high efficiency, while minimizing the size of the construct. As used herein, "processing unit," can refer to a polypeptide sequence that includes, from N terminus to C terminus, an N-terminal autocatalytic cleavage domain, and a C-terminal cleavage domain. In some embodiments, a linker is positioned between the N-terminal autocatalytic cleavage domain and the C-terminal cleavage domain. Accordingly, some embodiments include a polynucleotide encoding at least two polypeptides of interest, and a processing unit, positioned in-frame between each of the polypeptides of interest. Some embodiments include a vector that encodes a processing unit, but does not encode polypeptides of interest.

In some embodiments, a processing unit comprises a polynucleotide encoding an N-terminal autocatalytic cleavage domain that includes an intein. When the domain is expressed, this intein can cleave the upstream polypeptide without overhanging C terminal amino acids on the upstream polypeptide. Additionally, the intein of the N-terminal autocatalytic cleavage domain can cleave the upstream polypeptide in substantially any cellular compartment, for example the cytosol.

In some embodiments, a processing unit comprises a polynucleotide encoding a C-terminal cleavage domain that includes another intein. If the C-terminal cleavage domain is an intein, the downstream polypeptide can be cleaved without N terminal overhang. Furthermore, if the C-terminal cleavage domain is an intein, the downstream polypeptide can be cleaved in substantially any cellular compartment, for example the cytosol. In some embodiments, the C-terminal cleavage domain is a Ssp DnaB intein. If the C-terminal cleavage domain is an intein, it can be desirable to increase the C terminal cleavage efficiency of the C-terminal cleavage domain, while N terminal cleavage of the C-terminal cleavage domain can be less important. Accordingly, in some embodiments in which the C-terminal cleavage domain includes an intein, the N-terminal most amino acid of that C-terminal cleavage domain intein is mutated. In some embodiments, the mutation is to an alanine. In some embodiments, for example if the intein is an Ssp DnaB intein, the mutation is C1A.

It can be desirable to cleave intein (and similar) moieties from polypeptides of interest before the polypeptide begins folding. Thus, for at least this reason, it can be desirable to perform co-translational cleavage of the downstream polypeptide from the upstream polypeptide. As discussed herein, the 2A sequence can perform co-translation cleavage, but leaves the 2A sequence hanging onto sequences upstream of 2A, while leaving a proline on the N terminus of sequences downstream of 2A. Thus, in some embodiments, the C-terminal cleavage domain includes a 2A sequence. The N-terminal autocatalytic cleavage domain can subsequently cleave the first intein from the upstream polypeptide, thus ultimately removing the intein-2A moiety from both polypeptides, and preventing 2A-induced degradation of the upstream polypeptide. In some embodiments, the 2A sequence is a viral 2A sequence. In some embodiments, the 2A sequence is a non-viral sequence. In some embodiments, a linker is positioned (in cis) between the first intein and the C-terminal cleavage domain. In some embodiments, for example if an N terminal proline overhang is acceptable on the downstream polypeptide, the 2A sequence is positioned immediately upstream of the N terminus of the downstream polypeptide.

In some embodiments, a UB or SUMO sequence is positioned downstream of the 2A sequence, but immediately upstream of the N terminus of the downstream polypeptide. Co-translational cleavage by the 2A sequence can leave an N terminal proline on the downstream sequence, but subsequent cleavage by a DUB or SENP in the cytosol or substantially any cellular compartment can remove the UB or SUMO moiety as well, thus leaving the N terminus of the downstream peptide with no overhang.

For some downstream polypeptides, it can acceptable for the downstream polypeptide to contain an N terminal proline, and/or to be targeted for degradation. Some embodiments include, from N terminus to C terminus, an upstream polypeptide of interest, a processing unit comprising an N-terminal autocatalytic cleavage domain and a 2A sequence, and a downstream protein of interest. In some embodiments, the C terminus of the upstream polypeptide of interest directly abuts, but does not overlap the N terminus of the intein. In some embodiments, the 2A sequence is a viral sequence, for example FMDV 2A. In some embodiments, the 2A sequence is a non-viral sequence, for example sea urchin (*Strongylocentrotus purpuratus*) 2A, one of a *amphioxus*, *porifera*, or acorn worm 2A-like sequence.

In some embodiments, a polynucleotide encodes, from 5' to 3', an upstream polynucleotide, a processing unit comprising an N-terminal autocatalytic cleavage domain selected from the "N-terminal autocatalytic cleavage domain" column in Table 1, a C-terminal cleavage domain selected from the "C-terminal cleavage domain" column of Table 1, and a downstream polypeptide. In some embodiments, for example embodiments in which 2A is in the C-terminal cleavage domain, the precursor polypeptide also includes a linker as described herein. Some embodiments include a nucleic acid that encodes the precursor polypeptide in a single transcript.

TABLE 1

| N-terminal autocatalytic cleavage domain | C-terminal cleavage domain |
|---|---|
| Intein | Intein* |
| Intein with last (NTD) aa mutated | Intein with first (CTD) aa mutated* |
| Mini-intein | Mini-intein* |
| Mini-intein with last (NTD) aa mutated | Mini-intein with first (CTD) aa mutated* |
| Hog domain | SUMO* |
| HINT Domain | UB* |
| B-type BIL | Furin site* |
| | 2A |
| | 2A-UB* |
| | 2A-SUMO* |

*Sequence noted with an asterisk can be downstream of C-terminal cleavage domain and immediately upstream of N terminus of downstream peptide, so as to cleave the C-terminal cleavage domain without leaving an overhang.

In some embodiments, the construct includes a polynucleotide of any of SEQ ID NOs: 6, 8, 10, 12, 14, 16, 18, 20. In some embodiments, the construct includes a polynucleotide encoding a processing domain, for example a polynucleotide including nucleotides 837-1617 of SEQ ID NO: 6; nucleotides 760-1364 of SEQ ID NO: 8; nucleotides 760-1254 of SEQ ID NO: 10; nucleotides 760-1336 of SEQ ID NO: 12; nucleotides 760-1762 of SEQ ID NO: 14; nucleotides 769-1728 of SEQ ID NO: 16; nucleotides 831-1516 of SEQ ID NO: 18; or nucleotides 760-1245 of SEQ ID NO: 20. In some embodiments, the construct include a variant of one of the listed sequences. In some embodiments, the variant has at least about 80% identity to the listed sequence, for example about 80%, 81%, 82%, 83%, 84%, 85%, 86%, 87%, 88%, 89%, 90%, 91%, 92%, 93%, 94%, 95%, 96%, 97%, 98%, 99%, 99.3%, 99.5%, 99.7%, 99.8%, 99.9%, or 99.99% identity including ranges between any two of the listed values. In some embodiments, the construct includes a polynucleotide encoding any of SEQ ID NOs: 7, 9, 11, 13, 15, 17, 19, or 21. In some embodiments, the construct includes a polynucleotide encoding a cassette that includes a processing domain of any of SEQ ID NOs: 7, 9, 11, 13, 15, 17, 19, or 21.

It can be advantageous to co-express more than two polypeptides. In some embodiments, polynucleotides encode processing units as disclosed herein, positioned between each of three or more polypeptides in a construct (e.g. first polypeptide-processing unit-second polypeptide-processing unit-third polypeptide). In some embodiments, each processing unit of a multi-polypeptide expression construct is the same. In some embodiments, two or more processing units of a multi-polypeptide construct are different, and for example may be selected based on desired performance characteristics. In some embodiments, the cleavage domains of the processing unit are selected independently of each other. Accordingly, in some embodiments, at least three or more polypeptides are co-expressed as separate polypeptides from a single precursor polypeptide, for example, at least 3, 4, 5, 6, 7, 8, 9, 10, 11, 12, 13, 14, 15, 16, 17, 18, 19, 20, 25, 30, 40, or 50 polypeptides can be co-expressed.

In some embodiments, it can be desirable to co-express polypeptides in stoichiometric ratios other than 1:1. For example, it may be desirable to express certain polypeptides in ratios of 2:1 (for example, if expressing a trimer having two identical subunits, and one unique subunit). Accordingly, in some embodiments, a multi-polypeptide expression construct includes two or more copies of the same polypeptide.

Methods

Methods of coordinately co-expressing two or more polypeptides can be useful for a variety of applications, including, but not limited to applications provided herein. Some embodiments include a method of processing a polypeptide. In some embodiments, the method is performed in a cell. In some embodiments, the method is performed in an extracellular environment or cell-free system. In some embodiments, the method includes providing a polynucleotide, encoding from 5' to 3' an upstream polypeptide of interest, an N-terminal autocatalytic cleavage domain, a C-terminal cleavage domain, and a downstream polypeptide of interest. In some embodiments, the polynucleotide is provided in a vector. In some embodiments, the polynucleotide is provided in the genome of a host cell. In some embodiments, the polynucleotide is transcribed in a cell. In some embodiments, the polynucleotide is synthesized. In some embodiments, translation of the polynucleotide (or its transcript) is initiated. In some embodiments, the method includes cleaving the upstream polypeptide from the N-terminal autocatalytic domain. In some embodiments, the C terminus of the upstream polypeptide does not include any amino acid overhangs. In some embodiments, the method includes cleaving the downstream polypeptide from the C-terminal cleavage domain. In some embodiments, the N terminus of the downstream polypeptide does not include any amino acid overhangs. In some embodiments, the method is performed in any cellular or extracellular location.

FIG. 2 is a flow diagram illustrating a method of expressing at least two separate polypeptides. In some embodiments, the method is performed in a cell 200. In some embodiments, the method is performed outside of a cell 210, for example in a cell-free system. In some embodiments, the method includes providing a precursor polypeptide as described herein, or expressing a precursor polypeptide or portion thereof from a single nucleic acid transcript. The precursor peptide can include, from N terminus to C terminus a first polypeptide of interest, a first N-terminal autocatalytic cleavage domain, a C-terminal cleavage domain, and a second polypeptide of interest 220. In some embodiments, the method includes cleaving the first polypeptide of interest from the N-terminal autocatalytic domain 240. In some embodiments, the first polypeptide of interest is cleaved from the N-terminal autocatalytic domain in any cellular or extracellular location 230. In some embodiments, the first polypeptide of interest is cleaved from the N-terminal autocatalytic domain such that there is no amino acid overhand on a C terminus of the first polypeptide of interest 245. In some embodiments, the method includes co-translationally cleaving the second polypeptide of interest at least a portion of the C-terminal cleavage domain from sequences upstream of the C-terminal cleavage domain 250. In some embodiments, the method includes cleaving the second polypeptide of interest from an upstream moiety that includes at least a portion of the C-terminal cleavage domain, such that there is no amino acid overhang on an N terminus of the second polypeptide of interest 280. In some embodiments, the second polypeptide of interest is cleaved from an upstream moiety that includes at least a portion of the C-terminal cleavage domain in the Golgi 260. In some embodiments, the second polypeptide of interest is cleaved from an upstream moiety that includes at least a portion of the C-terminal cleavage domain in any cellular or extracellular location 270.

One skilled in the art will appreciate that, for the methods disclosed in FIG. 2 and other processes and methods disclosed herein, the functions performed in the processes and methods can be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the method includes synthesizing or cloning the polynucleotide as described herein. In some embodiments, the method includes providing a vector without polynucleotides encoding polypeptides of interest, and nucleotides encoding polypeptides of interest are subsequently added. In some embodiments, the method includes providing a vector containing the polynucleotide as described herein. In some embodiments, the method includes introducing the vector to a host cell, for example by transforming, transfecting, or transducing the host cell. In some embodiments, the method includes transcribing the polynucleotide in the host cell. In some embodiments, the polynucleotide is transcribed from a promoter as described herein.

In some embodiments, the method includes cleaving the upstream polypeptide of interest, upstream of the N-terminal autocatalytic cleavage domain. In some embodiments, the N-terminal autocatalytic cleavage domain autocatalytically cleaves a peptide bond between its N terminus and the C terminus of the upstream polypeptide. In some embodiments, the N-terminal autocatalytic cleavage domain is positioned immediately downstream of the C terminus of the upstream polypeptide, and accordingly, cleaves the upstream polypeptide from the processing unit moiety that contains the N-terminal autocatalytic cleavage domain without any overhanging amino acids on the C terminus of the upstream polypeptide. In some embodiments, the N-terminal autocatalytic cleavage domain includes an intein. In some embodiments, the intein includes a mutation as described herein, for example a mutation on the most C terminal amino acid of the intein. In some embodiments, the N-terminal autocatalytic cleavage domain performs the cleavage in the cytosol. In some embodiments, the N-terminal autocatalytic cleavage domain performs the cleavage in substantially any cellular location. In some embodiments, the N-terminal autocatalytic cleavage domain performs the cleavage in any cellular location. In some embodiments, the N-terminal autocatalytic cleavage domain performs the cleavage in an extracellular, or cell-free environment.

In some embodiments, the C-terminal cleavage domain includes an intein as described herein. Accordingly, in some embodiments, the method includes cleavage of the C-terminal cleavage domain in any cellular or extracellular location. In some embodiments, the intein is positioned immediately upstream of the N terminus of the downstream peptide. The method can include cleaving the second polypeptide from the precursor polypeptide such that there is no overhang on the N terminus of the downstream polypeptide.

In some embodiments, the C-terminal cleavage domain includes a 2A sequence as described herein. In some embodiments, for example embodiments in which the C-terminal cleavage domain includes 2A, the method includes co-translationally cleaving the first polypeptide from the second polypeptide. This skilled artisan will appreciate that this 2A-mediated cleavage can occur in the cytosol. In some embodiments, 2A-mediated cleavage leaves a portion of 2A on the C-terminus of the upstream moiety, and a proline on the N-terminus of the downstream moiety. Thus, in some embodiments, the downstream polypeptide and at least a portion of the C-terminal cleavage domain are co-translationally cleaved from sequences upstream of the C-terminal cleavage domain. In some embodiments, the portion of 2A on the C-terminus of the upstream moiety can be removed from the upstream polypeptide when the first intein cleaves at the C-terminus of the upstream polypeptide, thus preventing degradation of the upstream polypeptide.

If 2A-mediated cleavage leaves a proline on the N-terminus of the downstream moiety, some embodiments of the method include cleavage of the overhang, thus producing a downstream polypeptide with no N-terminus overhang. In some embodiments, at least one of UB or SUMO is positioned (in cis) between the 2A site and the N-terminus of the downstream peptide. Accordingly, the method can include removal of the proline overhang in the cytosol, or in substantially any cellular location, or in any cellular location. In some embodiments, an intein or mini-intein, or HINT domain is positioned between the 2A site and the N-terminus of the downstream peptide. Accordingly, the method can include removal of the proline overhang in any cellular or extracellular location.

In some embodiments, the C-terminal cleavage domain includes a SUMO or UB sequence as described herein. In some embodiments, the downstream polypeptide is cleaved from the polypeptide precursor in any cellular location, or substantially any cellular location. In some embodiments, for example embodiments in which the C-terminal cleavage domain includes SUMO or UB positioned immediately upstream of the N terminus, the method includes cleavage of the downstream polypeptide such that there is no overhang on the N terminus of the downstream polypeptide.

In some embodiments, the method is performed in a eukaryotic cell. In some embodiments, the method is performed in a single-cell eukaryotic organism, such as yeast or algae. In some embodiments, the method is performed in a monocot. In some embodiments the method is performed in a dicot. In some embodiments, the method is performed in maize. In some embodiments, the method is performed in tobacco. In some embodiments, the method is performed in a mammalian cell. In some embodiments, the mammalian cell is one of a COS, CHO, BHK, HEK293, or 3T3 cell. In some embodiments, the mammalian cell is part of a multicellular organism.

In some embodiments, a polynucleotide encoding the processing unit and polypeptides of interest is provided. In some embodiments, the codons of the polynucleotide are optimized for the organism in which the polynucleotide is to be translated. In some embodiments, the polynucleotide is part of a vector. In some embodiments, the polynucleotide is cloned into a vector. In some embodiments, the polynucleotide is a transcript. In some embodiments, the polynucleotide is an mRNA. In some embodiments, the polynucleotide is a cDNA. In some embodiments, the polynucleotide is integrated into the genome of a host cell. In some embodiments, the polynucleotide is expressed from a single promoter.

In some embodiments, the method includes co-expressing three or more polypeptides of interest. The three or more polypeptides can be expressed on the same precursor polypeptide as described herein, and then cleaved using methods and constructs described herein, thus yielding three or more separate polypeptides.

Figure 3:
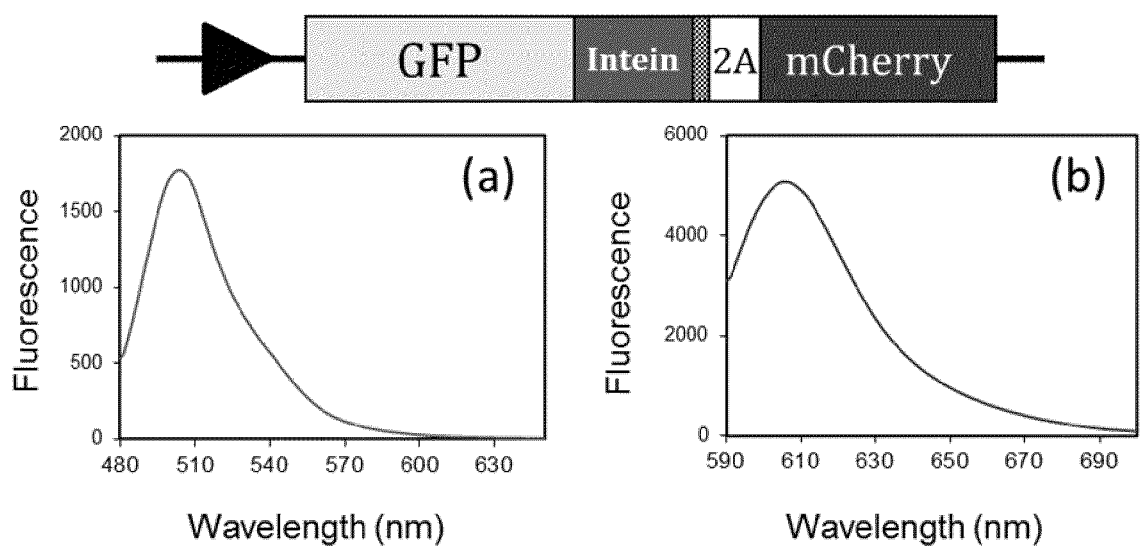
FIG. 3 illustrates expression of an upstream GFP reporter and a downstream mCherry reporter in a GFP-intein-linker-2A-mCherry construct (with reference to the construct shown in FIG. 6A), illustrating relative fluorescence of the upstream (a) and downstream (b) reporter.
Figure 4:
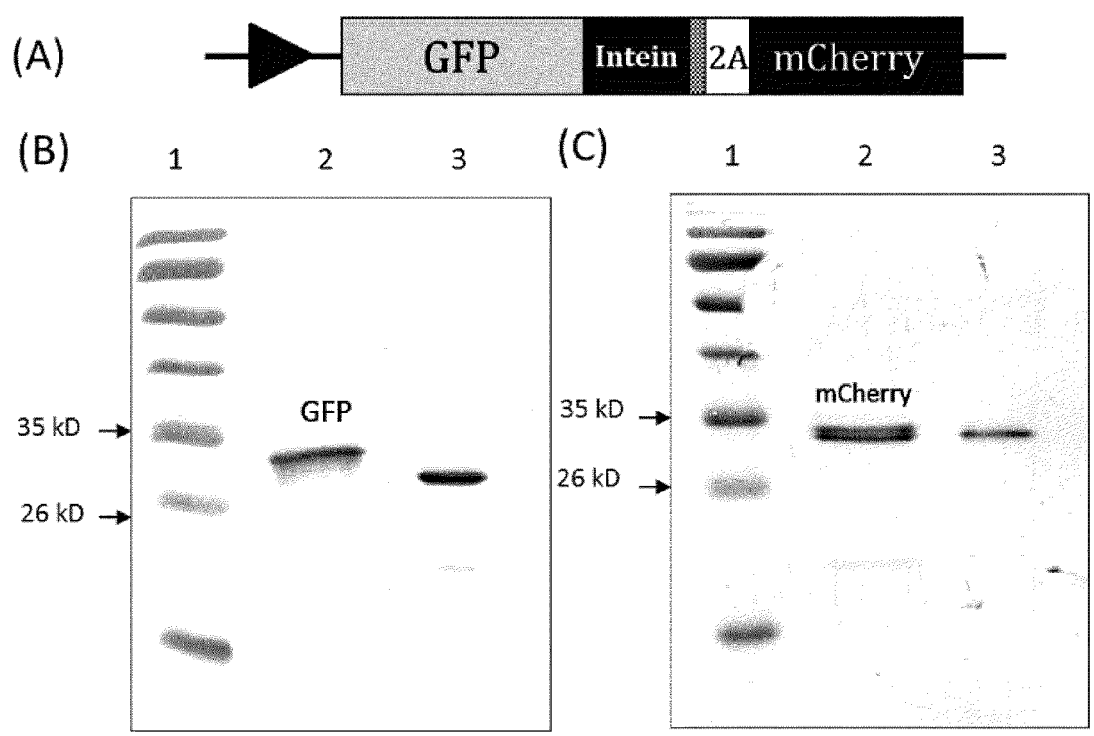
FIG. 4 illustrates expression of an upstream GFP reporter and a downstream mCherry reporter in a GFP-intein-linker-2A-mCherry construct (with reference to the construct shown in FIG. 6A), illustrating western blots of the upstream (B)-(C) and downstream (D)-(E) reporter.
Figure 5A:
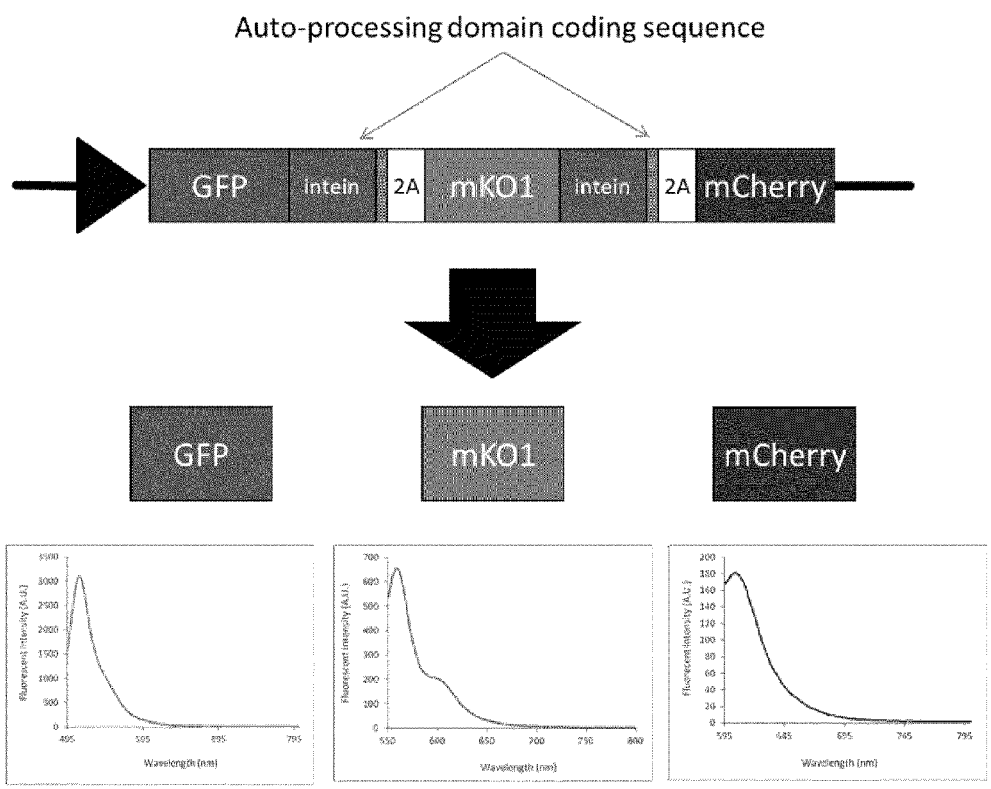
FIG. 5A illustrates expression of a three-reporter GFP-mKO1-mCherry construct, illustrating fluorescence activity of the first reporter (GFP), second reporter (mKO1), and third reporter (mCherry).
Figure 5B:
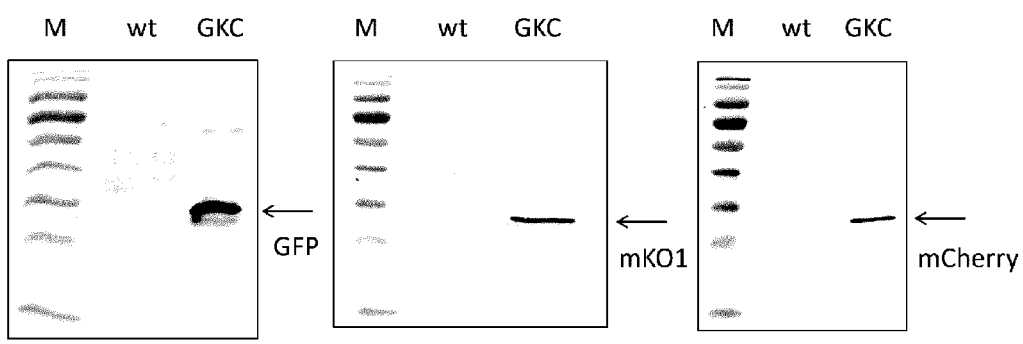
FIG. 5B illustrates western blots of expression of a three-reporter GFP-mkO1-mCherry construct, illustrating bands of cleaved first reporter (GFP), second reporter (mKO1), and third reporter (mCherry).

It can be desirable to co-express two or more polypeptides in stoichiometric ratios, for example is co-expressing the subunits of a multimer. As shown in FIGS. 3-4, a polynucleotide encoding an upstream polypeptide of interest and a downstream polypeptide of interest separated by a processing unit that includes an intein, a linker, and 2A (SEQ ID NO: 8), can produce separate fluorescent reporter proteins that have fluorescence activity, and protein expression levels in stoichiometric ratios. As shown in FIGS. 5A and 5B, an expression construct containing three reporter polypeptides, each separated by a processing unit, can produce three separate fluorescent reporter proteins that have fluorescence activity. Accordingly, some embodiments include coordinate expression of polypeptides in stoichiometric ratios. In some embodiments a first peptide of interest and a second peptide of interest are co-expressed as described herein, and the molar ratio of first peptide to second peptide is about 1:1, for example about 0.6:1, 0.7:1, 0.8:1, 0.9:1, 0.95:1, 0.98:1, 0.99:1, 0.995:1, 1:1, 1:1.005, 1:1.01, 1:1.02, 1:1.05, 1:1.1, 1:1.2, 1:1.3, 1:1.4, 1:1.5, or 1:1.6.

Screening

Figure 24:
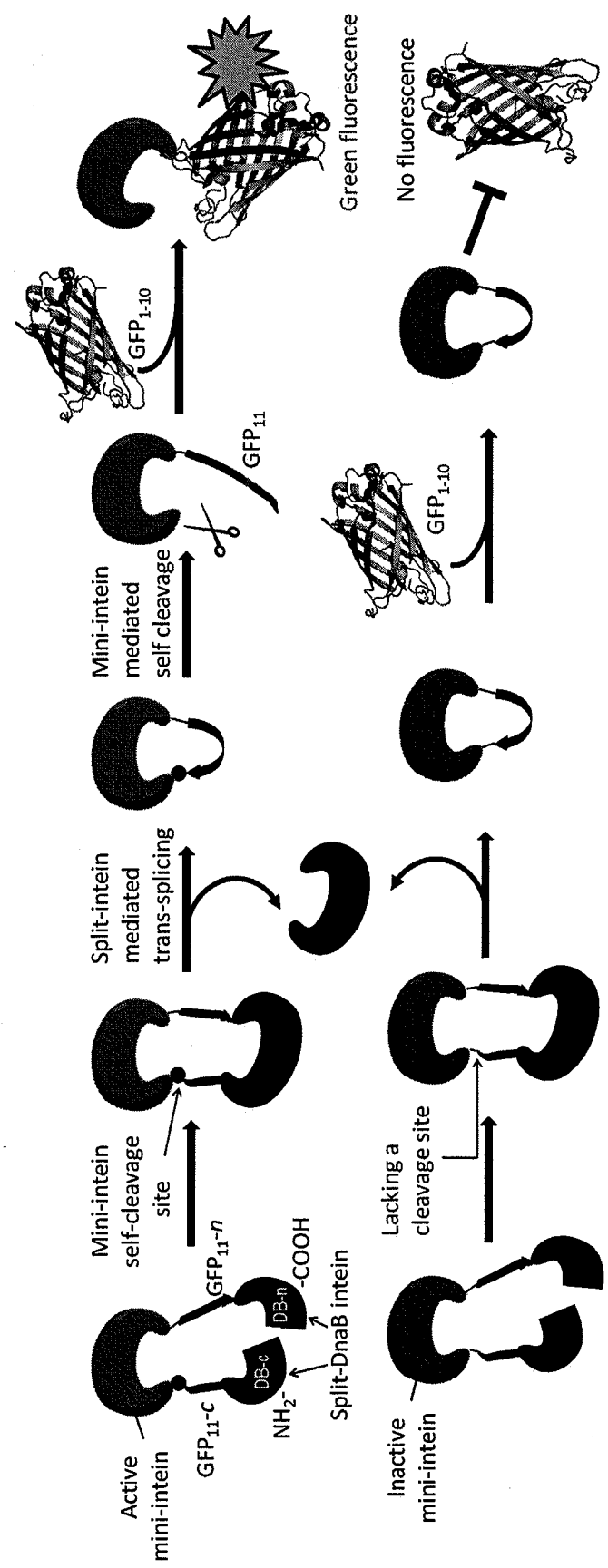
FIG. 24 illustrates the split-GFP in-vivo screening assay for selecting mini-intein derivatives with high terminal cleavage activities.

As taught herein, constructs including autocatalytic cleavage domains, such as inteins and BILs can be used for a variety of applications. It can be desirable to identify functional (and non-functional) modifications to autocatalytic cleavage domains, which can be used for a desired application. Accordingly, some embodiments include methods of screening for variants of autocatalytic cleavage domains. As shown in Example 6, a split-GFP screening scheme (FIG. 24) can select variants of autocatalytic cleavage domains with high N-terminal autocleavage activity, for example variants of inteins of BILS. The method can include trans-splicing between a first molecule having polypeptide splicing activity, for example, an active mini-intein, and split domains of a second molecule having N-terminal cleavage activity, for example a DnaB intein. The method can include split domains of a reporter molecule, for example the GFP-11 subunit. An n-terminal fragment of the reported molecule can be fused to an n-terminal fragment of a second molecule having polypeptide cleavage and splicing activity, for example an n-terminal fragment of a DnaB intein (DB-n). A c-terminal fragment of the reported molecule can be fused to an c-terminal fragment of the molecule having C-terminal cleavage activity, for example a c-terminal fragment of a DnaB intein (DB-c). As shown in FIG. 24, trans-splicing by the first molecule having polypeptide splicing activity can fuse the n- and c-terminal fragments of the second molecule. The reconstitution of the second molecule having cleavage and splicing activity (for example the DnaB intein) can result in the excision of the second molecule, and the splicing of the reporter molecule. Accordingly the reporter molecule is now fused to the N- and C-termini of the first molecule having splicing activity. If the first molecule also has N- or C-terminal cleavage activity, at least one terminus of the reporter molecule can be released, and the reporter molecule can be detected, for example by fluorescence if the reporter molecule includes a fluorescent molecule. Alternatively, if the first molecule lacks N- and C-terminal cleavage activity, the reporter molecule will remain fused to the termini of the first molecule, and will not be detectable. In some embodiments, the first molecule includes a mini-intein. In some embodiments, the first molecule includes a full-length intein. In some embodiments, the first molecule includes a BIL. In some embodiments, for example, if intein variants are being screened, the first molecule includes one or more random mutations. In some embodiments, the first molecule includes one or more-site directed mutations.

Figure 26:
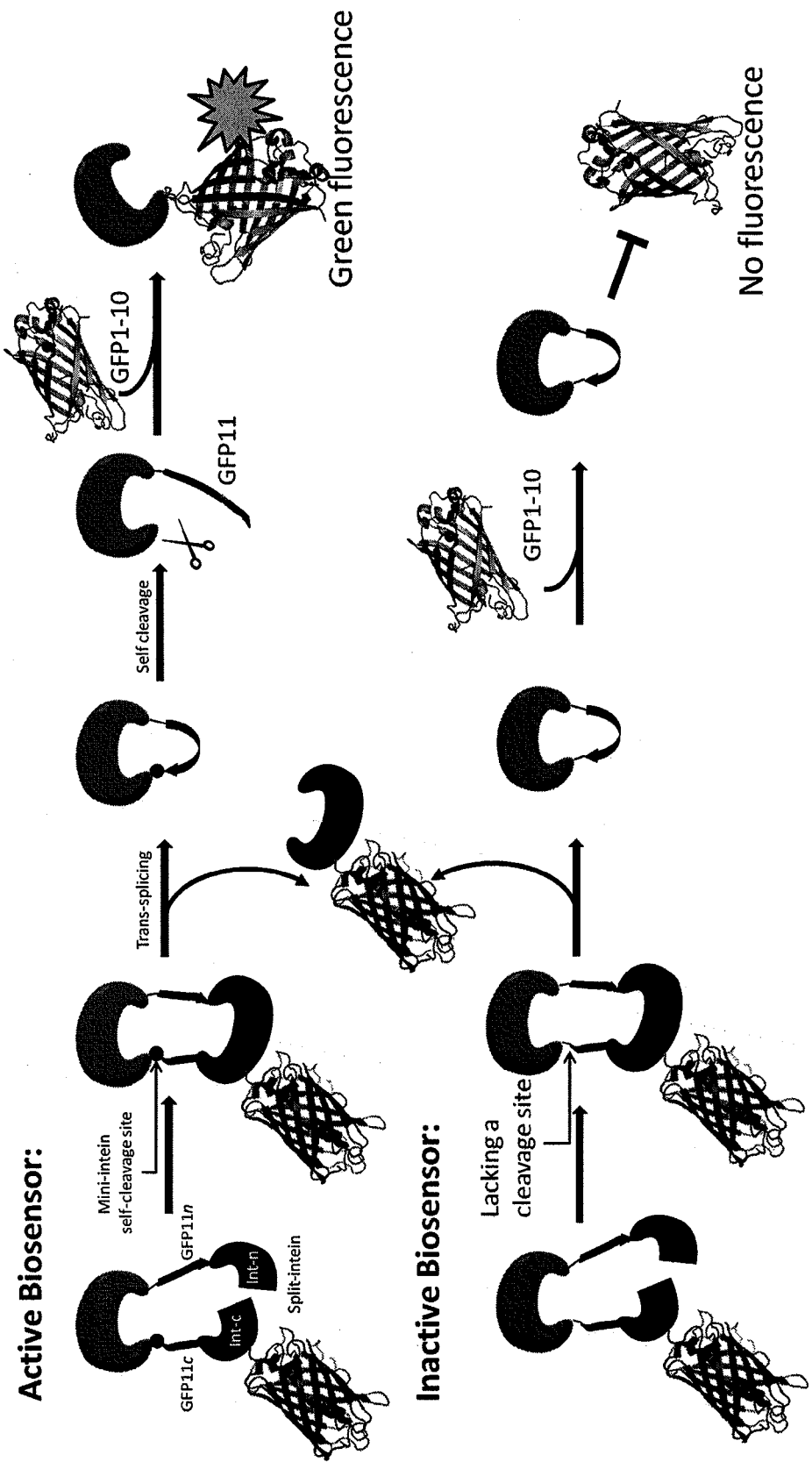
FIG. 26 illustrates incorporation of mCherry in the split-GFP based in-vivo screening sensor to normalize the sensor response.

DnaB (DB-c & DB-n) joins the two fragments of GFP11 (GFP11-n and GFP11-c represent N- and C-terminal fragments of GFP11, respectively) to form a complete GFP11 strand. With active mini-intein derivatives having high N-terminal cleavage activity, the spliced GFP11 becomes a peptide tag fused to the C-terminus of the intein and reconstitutes with GFP1-10 to form a fluorescent GFP, whereas for an inactive intein (with no N-terminal cleavage) the close distance between the two termini of intein puts a strain on the GFP11 and likely prevents it from reconstituting with the GFP1-10 to form a fluorescent protein. The split Ssp DnaB intein has been used for the synthesis of cyclic peptide in *E. coli* (Scott et al. (1999), Proc Natl Acad Sci USA 96:13638-13643). Normally the most important flanking extein residue for effective splicing is the one at C+1. In the case of the DnaB intein, the native C+1 residue is Ser. To this end, a GFP11 mutant called M2 (L221H, F223S, T225N) showing improved reconstitution with GFP1-10 compared with wild-type GFP11 does contain a Ser residue in the middle of its sequence DHMVLHES-VNAA (SEQ ID NO: 30) (Cabantous et al. (2005), Nat Biotechnol 23:102-107). Therefore we used the sequence DHM-VLHE (SEQ ID NO: 31) as G11-n and SVNAA (SEQ ID NO: 32) as G11-c. We created two split-GF sensor constructs, one contains an active N159A DnaE mini-intein and the other contains a C1A/N159A inactive intein. When co-expressed with a GFP1-10 gene, *E. coli* expressing the active intein gave strong fluorescence while there was no fluorescence seen for inactive intein (FIG. 25). Western blot was also conducted to further verify the identity and processing of the sensor proteins (FIG. 25). The proposed split-GFP system has the advantage of being a "turn-on" sensor, i.e. lights up in positive clones, as opposed to "turn-off" sensors in which the signal is lost or reduced in positive clones, such as the FRET sensor reported in Amitai et al (Amitai et al. (2009), Proc Natl Acad Sci USA 106:11005-11010), and that can potentially improve sensor sensitivity. Furthermore, the proposed design can potentially provide tight negative control and hence lowered background noise. We have also appended a RFP (red fluorescent protein mCherry) to the amino-terminus of the split-GFP sensor and showed that it allowed normalization of the sensor response (FIG. 26).

Some embodiments include kits. The kit can include a polynucleotide encoding a modified GFP-11 fragment that includes the sequence of SEQ ID NO: 30. The kit can include at least one polynucleotide encoding GFP 1-10. The kit can include a polynucleotide encoding an n-terminal GFP-11 fragment of SEQ ID NO: 31, and a c-terminal GFP-11 fragment of SEQ ID NO: 32. The kit can include polynucleotide encoding an n-terminal fragment of an intein, for example an DnaB intein. The kit can include polynucleotide encoding a c-terminal fragment of an intein, for example the DnaB intein. The kit can include polynucleotide encoding an active mini intein, having N-terminal cleavage and splicing activity. In some embodiments, the polynucleotide encoding the n-terminal intein fragment is fused to the n-terminal GFP 11 fragment, so as to express, from N-terminal to C terminal, GFP-11-n-intein-n, for example DnaB-n-GFP-11-n. In some embodiments, the polynucleotide encoding the c-terminal intein fused to the c-terminal GFP 11 fragment, so as to express, from N-terminal to C terminal, intein-c-GFP-11-c, for example DnaB-c-GFP-11-c.

Kits

Some embodiments include a kit. The kit can include a vector that comprises a polynucleotide encoding a processing unit as described herein. In some embodiments, the vector unit as described herein. In some embodiments, the vector comprises at least one multiple cloning site. In some embodiments, the vector does not encode one, two, or any polypeptides of interest. For example, the vector may comprise a processing unit as described herein and sites for cloning in nucleotides encoding polypeptides of interest.

Applications

Methods and constructs disclosed herein can be used for a wide variety of applications, for example in in agriculture, in research, in manufacturing, and in medicine.

In some embodiments, methods disclosed herein can be used for engineering cellular metabolism by altering existing metabolic pathways or by introducing an entirely new pathway from another organism. For example, programmed biological organisms can be used to produce desired molecules, for example biofuels, drug precursors, enzymes, and the like by expressing components of metabolic and/or synthetic pathways in these cells.

Modified (GM) crops, including soybeans, corn, cotton, rice, and tobacco, can offer many advantages, for example increased tolerance of adverse conditions (such as heat or drought), resistance to pesticides that can be used to eliminate undesired organisms, an increased nutrient or metabolite content. In some embodiments, methods disclosed herein can be used to co-express multiple polypeptides in GM crops, for example to express a multi-subunit complex, and/or to simultaneously introduce multiple desirable traits, such as drought tolerance and disease resistance) or complex value-adding traits (such as production of high-value metabolites) into crops for agricultural biotechnology and renewable bioenergy applications. In some embodiments, co-expression permits resistance to two or more pesticides. A first polypeptide conferring resistance to a first pesticide can be co-expressed with a second polypeptide conferring resistance to a second pesticide.

Production and/or delivery of monoclonal antibodies (mAbs) for therapeutic treatments can greatly benefit from a highly precise coordinate multi-protein expression system. mAbs have become a class of very important therapeutic agents for the treatment of cancer, inflammation as well as infectious diseases. Production of mAbs at an industrial scale relies on recombinant DNA technology and is typically carried out in mammalian cells. Conventional antibody expression cassettes drive the mAb heavy and light chains from two individual promoters. It is difficult to coordinate the expression level of the heavy and light chains using the conventional expression cassettes even with the same type of promoter. Without being bound by any one theory, duplications of promoter and additional regulatory sequences in the cassette also can lead to genetic instability. Accordingly, in some embodiments, methods and constructs described herein are used for the coordinate expression of the heavy and light chain of a monoclonal antibody, for example in large-scale industrial manufacturing applications. In addition to administering a mAb as a purified protein agent, it is also plausible to deliver mAbs through gene therapy, typically via recombinant adeno-associated virus vectors. The viral vector can be administered to enable sustained expression of mAbs from the vector in vivo. To this end, a variety of vectors can often accommodate only a limited size of the transgene insert, and hence expression of both heavy and light chains from a single ORF with minimum transgene length can be advantageous.

Accordingly, some embodiments include co-expressing an antibody heavy and light chain in a living cell of a patient in need of treatment by the antibody. Yet another approach to improve antibody production is to co-express protein(s) that facilitate folding or stabilize the antibody molecules. In some embodiments, one or more proteins that facilitate folding or stabilization of the antibody are co-expressed with the antibody heavy and/or light chain.

For expression of therapeutic agents such as antibodies, it can be advantageous to express each subunit without an N or C-terminal overhang. Accordingly, in some embodiments, an antibody light and heavy chain are co-expressed using a processing unit that includes an N terminal autocatalytic domain that includes an intein, and a C-terminal cleavage domain that includes one of UB, SUMO, 2A, 2A-UB, 2A-SUMO, or furin.

Induced pluripotent stem cells are well-known, as are methods of making induced pluripotent stem cells (see, e.g. U.S. Pat. Nos. 8,048,999, 8,058,065, and 8,129,187). Induced pluripotent stem cells can be made by co-expressing several factors, for example combinations of Oct3/4, Sox2, Klf4, Nanog, Lin-28, and/or c-Myc. Accordingly, in some embodiments, methods and constructs disclosed herein can be used to co-express reprogramming factors for making induced pluripotent stem cells.

A recent approach for producing therapeutic proteins, especially large-scale production of inexpensive vaccines for emerging infectious diseases, is the use of transient protein expression in plants. Some embodiments can improve and significantly simplify the production in such application. In some embodiments, the methods and constructs herein are used to co-express two or more components of cancer vaccines, for example two or more cancer-associated antigens. Furthermore, some embodiments apply to agricultural biotechnology. Early examples of genetically modified crops involve manipulation of simple traits that require introduction of a single gene. The current trend is to introduce multiple traits (i.e. trait stacking) or more complex traits. This often calls for coordinate manipulation of multiple proteins (enzymes, transcription factors, signaling factors, etc.). Accordingly, some embodiments include introducing multi- or complex traits in an agricultural organism, by co-expressing two or more polypeptides that can affect those traits.

In some embodiments, the methods and constructs herein are used for gene therapy, for example replacing two or more subunits of a complex that is not being properly expressed in a patient in need. In some embodiments, the methods and constructs herein are used in one or more eukaryotic microorganisms such as yeasts, fungi, and micro- and macroalgae.

Additional Alternative Embodiments

Methods and constructs are disclosed that can significantly simplify and improve coordinate expression of multiple proteins in eukaryotes, especially plant and mammalian systems. Some embodiments include a novel synthetic fusion protein domain with exceptional self-processing properties that enables efficient production of multiple proteins from a single open reading frame (ORF) that encodes a polyprotein precursor. The synthetic protein motif excises itself out from the polyprotein precursor, and releases the flanking proteins without residual amino acid overhang. Several innovative molecular designs are disclosed to introduce the unique autocatalytic cleavage property to the synthetic protein domain. Some embodiments include a hybrid protein domain that includes an engineered mini-intein variant with high N-terminal autocleavage activity which is linked, via a peptide linker, to a ubiquitin (UB) that can be cleaved off at its C-terminus with high efficiency in vivo by the deubiquitinating enzymes (DUBs), or to a UB-like sequence such as the small UB-like modifier (SUMO) cleavable by the SUMO-specific proteases. Some embodiments incorporate another component—the cis-acting hydrolase element (CHYSEL) peptide such as the viral or non-viral 2A sequence, sandwiched between the intein and UB domains in the expression constructs. Having the ability to effectively and precisely manipulate the level of multiple gene products through coordinate expression can allow the redirection of metabolism and trait stacking, and can be useful in a wide range of fields from enhancing crop yield and nutritional values, environmental remediation, to producing value-adding products and improving human health. Though techniques have been disclosed that allow introduction and expression of multiple genes in living organisms, these techniques all have certain drawbacks. Most of these techniques involve laborious procedures and are limited in their ability to achieve efficient coordinate gene expression. Some embodiments offer competitive advantages over these existing techniques.

By harnessing the synergy between polypeptides with N-terminal auto-cleavage properties, such as the unique N-terminal auto-cleavage property of engineered mini-inteins (or other HINT domain proteins such as hedgehog self-processing protein and bacterial intein-like proteins), as well as those of polypeptides with efficient in vivo C-terminal cleavage, such as UB or SUMO sequences, some embodiments include a superior approach for multi-protein expression in eukaryotic cells. In some embodiments, the multiple protein expression approach combines the unique attributes of HINT domain and UB (or SUMO), and is illustrated in FIG. 1C. By harnessing the synergy between the unique properties of engineered mini-inteins (or other HINT domain proteins such as hedgehog self-processing protein and bacterial intein-like proteins), as well as those of 2A-like "CHYSEL" peptide sequences from FMDV and other Picornaviruses, some insect viruses, a dsRNA crustacean virus, type C rotaviruses, and repeated sequences within *Trypanosoma* spp (a list of such sequences is accessible on the world wide web at www.st-andrews.ac.uk/ryanlab/Index.htm) some embodiments include an improved approach for multi-protein expression in eukaryotic cells. Some embodiments incorporate the cis-acting hydrolase element (CHYSEL)peptide such as the viral or non-viral 2A sequence, sandwiched between the intein and UB domains in the expression constructs (FIG. 1C).

Figure 1B:
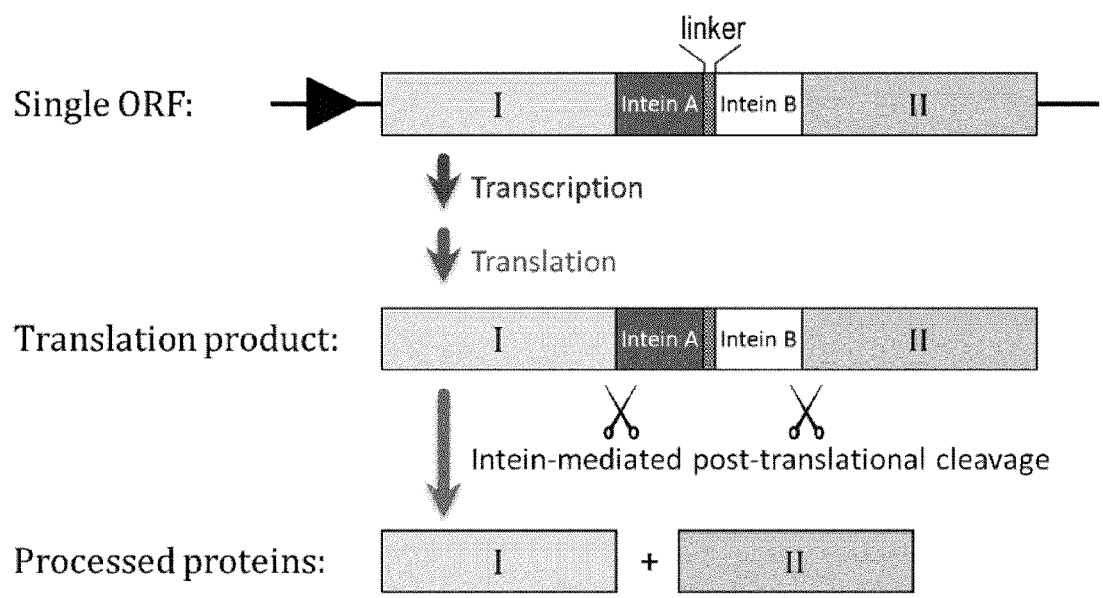
FIG. 1B schematically illustrates some embodiments in which a polynucleotide encodes an upstream polypeptide (I), an intein, a linker, a second intein, and a downstream polypeptide (II).
Figure 1C:
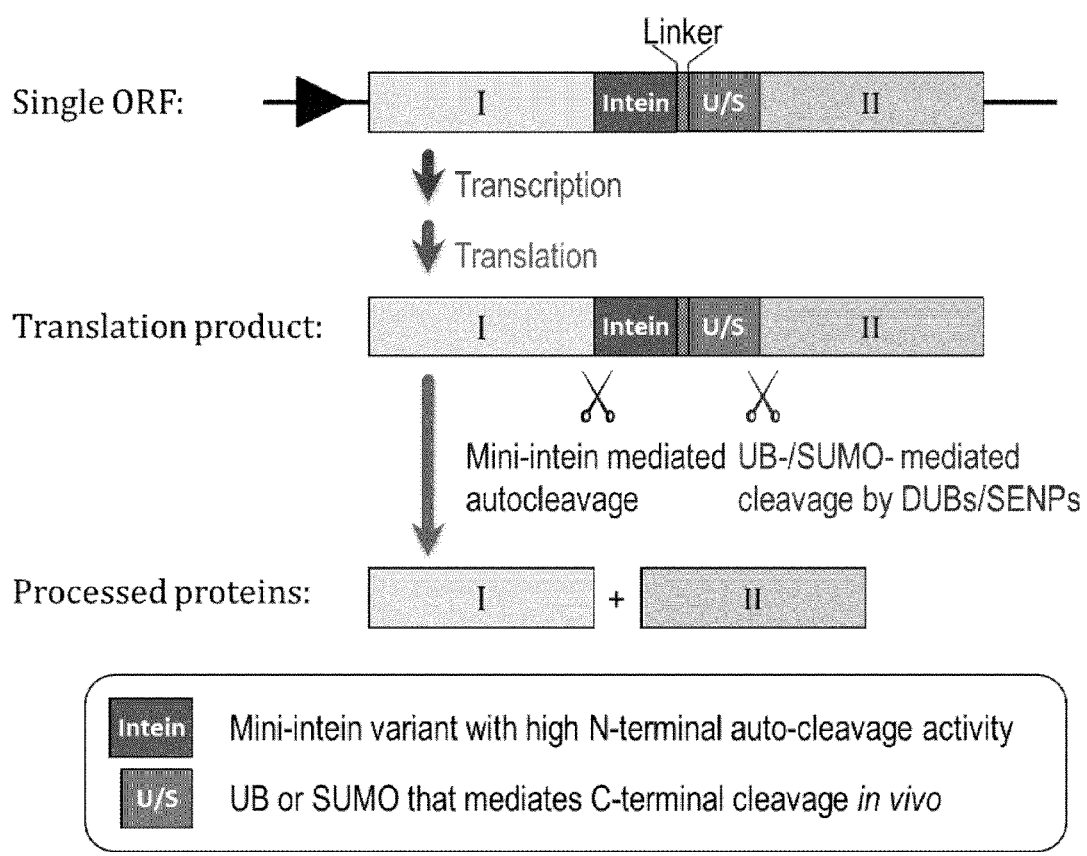
FIG. 1C schematically illustrates some embodiments in which a polynucleotide encodes an upstream polypeptide (I), an intein, a linker, a 2A sequence, one of UB or SUMO (U), and a downstream polypeptide (II).

In some embodiments, the disclosed multiple-protein expression approach combines desirable attributes of the HINT domain and 2A or the HINT DOMAIN and UB/SUMO, and is illustrated in FIGS. 1A and 1B. The 2A sequence enables co-translational processing of a precursor polyprotein molecule into individual protein elements via an unusual ribosome skipping mechanism. As disclosed herein, in vivo self-excision of the 2A sequence overhang via intein-mediated N-terminal autocleavage can be used, by creating a fusion protein domain that contains, for example, an engineered mini-intein connected to a 2A sequence through a linker. This intein-2A fusion protein domain is relatively small (about 20 kD) and may be further reduced in size. Unlike other existing polyprotein vector technologies, the intein-2A fusion motif based approach enables co-translational cleavage via 2A (resulting from ribosome skipping), followed by very efficient post translational autocatalytic cleavage via intein, and it does not require the presence of any host-specific cofactors or auxiliary enzymes.

With the 2A approach, an N-terminal proline residue will append to the downstream protein which sometimes may affect (increase or decrease) the protein activity. By using an intein-2A-UB domain, for example, this problem can be resolved because the protein downstream UB will preserve its native N-terminal residue.

In addition to the intein-2A fusion domain, some embodiments also include a dual-intein domain design. By fusing a mini-intein engineered for maximum N-terminal cleavage to a second mini-intein modified for maximum C-terminal cleavage, via a peptide linker, a fusion protein domain with N and C-terminal self-cleavage is created (FIG. 2).

In some embodiments, attributes in the multi-gene expression construct are further modified. The attributes that can be further modified include (but are not limited to): (a) different types of intein and HINT domain variants, (b) truncated and minimized intein or other HINT domain, (c) design of the peptide linker (length/sequence) that connects the intein domain and the UB or SUMO motif to incorporate the most favorable C-extein flanking residues for promoting intein-mediated N-terminal autocleavage, (d) different subcellular targeting signals, (e) different UB or SUMO domains, (j) use of non-viral 2A or 2A-like CHYSEL peptide sequences, and (k) different N- and C-exteins. In fact this invention claims the use of any synthetic protein domain that displays both intein-like amino-terminus autocleavage property and UB-like C-terminal cleavage property in the expression of multiple proteins from a single polyprotein precursor.

In some embodiments, the intein-UB based polyprotein expression approach includes the intein effectively autocatalyzing the cleavage at its amino-terminal juncture with the N-extein and thus releases itself along with the UB tag from the N-extein (refer to FIG. 1C).

Several studies have demonstrated that mutations within the intein sequence and the flanking extein residues led to significantly increased cleavage activity with much attenuated splicing efficiency (Amitai, et al. (2009) Proc. Nat. Acad. Sci. USA 106; 11005-10; Xu, et al (1996). Embo J 15:5146-53). The mutation of the C-terminal Asn residue in intein to Ala abolished essentially all native protein splicing function while preserving the cleavage activity (Amitai, et al. (2009) Proc. Nat. Acad. Sci. USA 106, Martin, et al (2001) Biochemistry 40:1393-402). In addition to the Ssp DnaE mini-intein, a variety of other inteins can be used. An extensive list of the known intein sequences is available at the InBase database (http://www.ncb.coll1/nfb/inteills.htll11). Two particular relevant inteins are the Ssp DnaB mini-intein (Mathys, et al. (1999) Gene 231:1-13.) and the *Mycobacterium tuberculosis* recA mini-inteins (Hiraga et al (2005) J Mol Bioi 354:916-26). These inteins are among the best characterized and are small in size.

In some embodiments, a dual-intein domain design is used. For example, by fusing a mini-intein engineered for maximum N-terminal cleavage to a second mini-intein modified for maximum C-terminal cleavage, via a peptide linker, a fusion protein domain with N and C-terminal self-cleavage can be created (FIG. 2). This is superior to engineering a single intein or its flanking extein residues to achieve both N- and C-terminal cleavage which typically leads to only partial cleavage and leaves behind a substantial portion of uncleaved polyproteins.

TABLE 2

Exemplary processing unit sequences

| SEQ ID NO: | Annotations | Exemplary FIG. No.: |
|---|---|---|
| 42 | DnaE intein: :FMDV 2A | 6A |
| 44 | DnaE Intein: :*Arabidopsis* Ubiquitin | 12A |
| 46 | DnaE intein: : *Strongylocentrotus purpuratus* 2A | 9A |
| 48 | DnaE intein: :DnaB intein | 10A |
| 52 | DnaE Intein: :FMDV-2A | 8A |
| 54 | DnaE intein: : *Strongylocentrotus purpuratus* 2A: : *Arabidopsis* Ubiquitin | 14A |
| Positions 245-510 of SEQ ID NO: 27 | DnaE Intein: :SUMO | 13A |

Example 1

Intein-FDMV 2A (Intein::F2A)

Example 1.1

Expression of Two Fluorescent Reporter Proteins Using an Intein:F2A Based Polyprotein Constructs in Stably Transformed Tobacco Cells A series of expression constructs was designed and assembled to examine how the intein:F2A fusion motif functions inside a plant cell environment. The organization of the construct is similar to that depicted in FIG. 1. A Ssp PCC6803 DnaE mini-intein sequence sandwiched between an upstream sequence that encodes a GFP variant, GFP172, containing an internal 6His-tag between amino acids 172 and 173, and a downstream sequence coding for a linker followed by a FMDV 2A motif, a red fluorescent protein variant, mCherry, with a C-terminal streptag (SEQ ID NO: 8), were assembled and cloned into a plant binary vector pE1775 under the control of the mannopine/octopine synthase (ocs)$_3$/mas promoter. The intein:F2A (in which F2A refers to FMDV 2A) gene coding sequence was synthesized according to tobacco codon preference. The linker that separates the intein and the 2A sequence contains the first three C-extein amino acid residues (which can reportedly accelerate N-terminal intein cleavage), followed by a linker shown to improve the 2A activity.

Initially the constructs were tested through transient expression using agroinfiltration in *Nicotiana Benthamiana* to enable speedier screening and analysis. Subsequently we established stably transformed tobacco NT1 cells via an *Agrobacterium*-cocultivation method. Representative results of GFP172-intein:F2A-mCherry-streptag expression in stably transformed NT1 cells are presented here. The transgenic NT1 cells were found to display both green and red fluorescence (FIG. 3). In vivo processing of the GFP172-intein:F2A-mCherry-streptag polyprotein in the transgenic NT1 cells was further examined using western blots (FIG. 4). We can clearly detect the released GFP and mCherry constituents but not the unprocessed polyprotein precursor. Our results indicate highly efficient processing of the polyprotein precursor within tobacco cells and the intein:F2A motif indeed function as we envisioned. Based on the fluorescence and protein concentration measurement, we also confirmed similar level of GFP and mCherry were produced. Furthermore, GFP and mCherry each amounts to 0.3-0.6% total soluble protein when expressed using the intein:F2A vector, which is comparable with the typical protein level of GFP when it is expressed alone in NT1 cells using the same $(ocs)_3$/mas promoter. Cleaved mCherry and GFP in NT1 extract were purified by strep-tactin chromatography or hydrophobic (phenyl) interaction chromatography followed by immobilized metal affinity chromatography (IMAC) and analyzed using N-terminal amino acid sequencing and ESI-TOF mass spectrometry (ESI-TOF MS), and were found to be cleaved at the expected sites (N-terminal of the intein domain and between the last two amino acids, i.e. Gly and Pro of the FMDV 2A). As a side note, we could not detect the excised intein:F2A cassette in western blot analysis probed with a 2A-specific polyclonal antibody, suggesting possible degradation of the excised intein:F2A domain in planta.

Example 1.2

Figure 15:
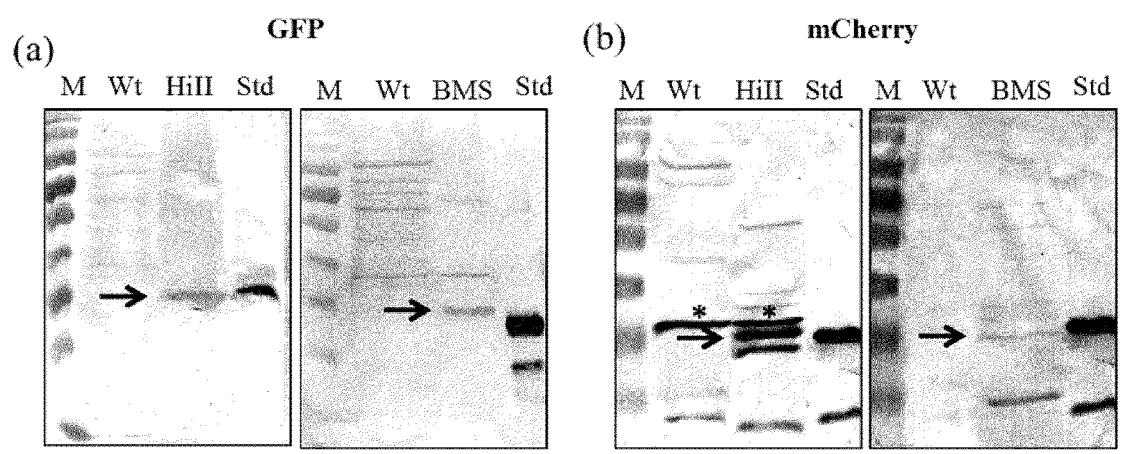
FIG. 15 illustrates processing of GFP-Intein::F2A-mCherry-steptag polyprotein in maize HiII hybrid endosperm and maize BMS (Black Mexican Sweet) suspension cells analyzed by western blot probed with (a) anti-GFP antibody; and (b) anti-streptag antibody. "→" and "*" denote target protein band and nonspecific immunoreactive band, respectively.

Transient Expression of Two Fluorescent Reporter Proteins Using an Intein:F2A Based Polyprotein Constructs in Maize To investigate the expression and processing of two fluorescent reporter proteins using intein:F2A based polyprotein in monocot plants, the GFP172-intein::F2A-mCherry-streptag sequence in pE1775 was amplified with polymerase chain reaction (PCR) and cloned into pCR8-TOPO TA vector and subsequently transfer to the binary vector pANIC6E under the control of the maize ubiquitin promoter via Gateway cloning strategy. The construct was transformed into both maize HiII AXB hybrid endosperm and maize BMS (Black Mexican Sweet) suspension cells via *Agrobacterium* co-cultivation. The *Agrobacterium*-co-cultivation experiments were carried out as described in previous publication (Armstrong et al., 2001, Requesens et al., 2010). The processing of GFP172-intein::F2A-mCherry-streptag polyprotein in maize expression system was examined using western blot (FIG. 15). Cleaved GFP and mCherry products were clearly detected in the extracts of both transformed maize HiII endosperm and maize BMS suspension cells, while no unprocessed polyprotein precursors were observed. This finding indicates the efficient processing of intein::F2A mediated polyprotein system in monocot plants (exemplified with maize).

Example 1.3

Expression of Proteins Other than Fluorescent Reporter Using an Intein::F2A Based Polyprotein Constructs in Tobacco To demonstrate the intein::F2A polyprotein system is applicable to express proteins other than fluorescent reporters, two intein::F2A polyprotein constructs were made (cf. FIG. 4A): one with the upstream GFP172 replaced with a human cytokine, hGMCSF containing a N-terminal hexa-Histag, and the other construct with the downstream mCherry proteins replaced with chloramphenicol acetyl transferase (CAT) containing a C-terminal streptag. For each construct, the expression cassette included nucleotides 760-1434 of SEQ ID NO: 8). The constructs were subsequently introduced into tobacco NT1 cells via *Agrobacterium*-cocultivation. The proper enzymatic activity of CAT as well as GFP fluorescence were detected in the extract of NT1 cells that are transformed with the GFP-intein::F2A-CAT-streptag construct. In addition, in-vivo processing of the GFP-intein::F2A-CAT-streptag and hGMCSF-intein::F2A-mCherry-streptag polyproteins in transgenic NT1 cells were confirmed using western blots (FIG. 15). Similar to the results with the co-expression of two fluorescent reporter proteins, there is no unprocessed polyprotein precursor observed in both construct, indicating the effective processing of the polyprotein precursors within tobacco cells. Based on western blot, enzymatic assay and fluorescent measurement, we confirmed that the CAT and GFP were produced approximately in stoichiometric amounts in the cell.

Example 1.4

Expression of Three Fluorescent Reporter Proteins Using an Intein::F2A Based Polyprotein Constructs in Tobacco The intein::F2A based auto-processing cassette can also mediate co-expression of more than two proteins. To validate this point, an intein::F2A construct harboring three different genes encode for GFP, mKO1, and mCherry, respectively, was assembled in the binary vector pE1775 by inserting the mKO1'-FLAGtag-Intein::F2A fragment between the F2A and mCherry in the GFP 172-intein::F2A-mCherry-streptag construct described above (SEQ ID NO: 8). The assembled construct was tested in *Nicotiana benthamiana* via agroinfiltration and stably transformed tobacco NT1 cells. In both systems, all three proteins were found to be correctly processed into the expected molecular sizes base on western blot analysis (FIG. 5B). The processed protein constituents possess proper fluorescent function (FIG. 5A).

Example 1.5

Figure 17:
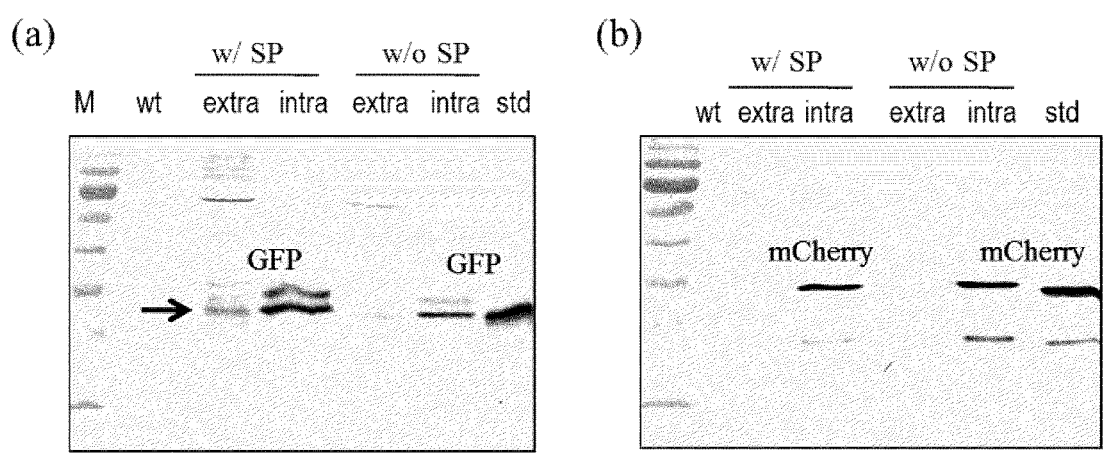
FIG. 17 illustrates western blots illustrating the different cellular targeting of protein constituents processed from intein:F2A polyprotein (Refer to construct in FIG. 8 and SEQ ID NOs: 18 and 19) in stably transformed NT1 cells. The concentrated media of suspension culture and intracellular cell extract were detected with anti-GFP antibody (a) and anti-streptag antibody (b)

Expression of Fluorescent Reporter Proteins that Target to Different Cellular Compartments Using an Intein::F2A Based Polyproteins Construct in Tobacco The individual protein moieties expressed using the intein::F2A based polyprotein system can be targeted to different cellular compartments by fusing signal peptides at the N-terminus of each protein constituent. As an example, an *Arabidopsis* basic chitinase signal peptide was fused at the N-terminus of the upstream protein (GFP172 in this case) to create the SP-GFP172-intein::F2A-mCherry-streptag construct. The construct was transformed into tobacco NT1 cells via *Agrobacterium*-cocultivation. The polyprotein processing and subcellular targeting of the released proteins were investigated using western blot analysis of cellular extract of transgenic NT1 cells and the concentrated media of suspension culture. As shown in the western blot (FIG. 17), both GFP and mCherry were effectively processed from the polyprotein precursor. In the concentrated media of suspension transgenic NT1 cell culture, a strong GFP immunoreactive band matching the processed GFP molecular weight was also detected, whereas, no mCherry immunoreactive band was detected in the culture media. This finding indicates that the autocatalytic cleavage can also occur when the protein precursor is targeted to the endoplasmic reticulum (ER). Additionally, removal of the intein::F2A sequence from the upstream GFP was efficient and therefore there was no GFP mistargeting observed.

Example 2

Intein-Non Viral 2A (Intein::S2A)

Figure 18:
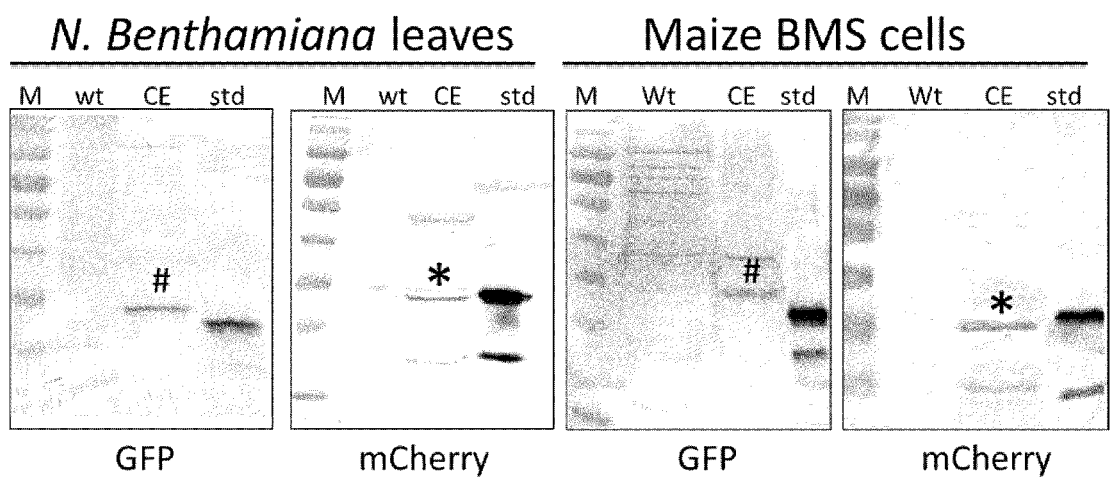
FIG. 18 illustrates western blots probing extracts of *N. benthamiana* leaves and maize BMS cells for GFP and mCherry, indicating efficient processing of polyprotein precursor mediated by the intein::S2A domain.

In this example, the FMDV 2A (F2A) sequence in the intein::F2A auto-processing cassette was replaced with a 2A like sequence found in purple sea urchin (*Strongylocentrotus purpuratus*), termed S2A herein. The S2A-mCherry-streptag fragment was assembled by 3-step overlapping PCR and cloned into the construct depicted in FIG. 1A to replace the original F2A-mCherry-streptag fragment in order to create the GFP172-intein::S2A-mCherry-streptag construct. This construct (SEQ ID NO: 12) was tested via transient expression in the leaf tissues of *Nicotiana tabacum* cv. *Xanthi* and *Nicotiana benthamiana* via agroinfiltration, as well as in maize HiII hybrid endosperms and maize BMS (Black Mexican Sweet) callus cells via *Agrobacterium*-cocultivation. Polyprotein processing was examined using western blot analysis. The western blot result indicates the intein::S2A domain can mediate correct processing of the polyprotein precursor in both dicot (*Nicotiana* sp.) and monocot (exemplified using maize) plants (FIG. 18).

Example 3

Intein::UB

Figure 20:
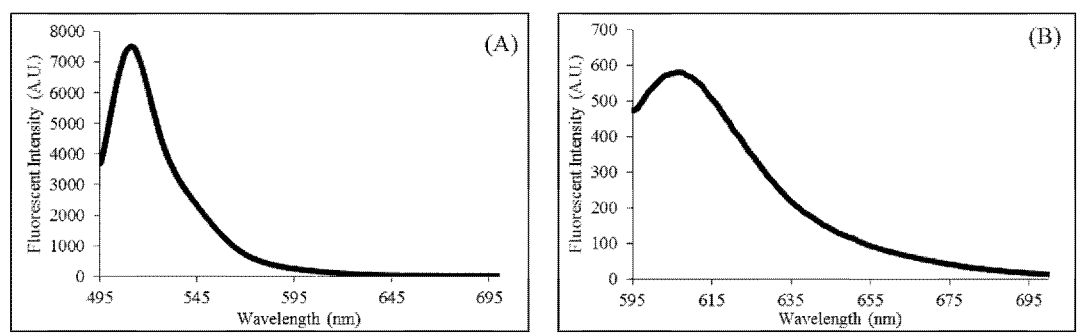
FIG. 20 illustrates fluorescent activity of processed GFP (A) and mCherry (B) from NT1 cells transformed with an intein::UBQ polyprotein construct.

In this example, an *Arabidopsis* ubiquitin domain variant with K48R mutation (UB) was used to replace the 2A sequence in the intein:2A auto-processing cassette to create the intein:UB domain for co-expressing multiple proteins. To create the intein:UB construct, GFP172-intein fragment and UB-mCherry-streptag fragment was synthesized independently with PCR and subsequently assembled into GFP172-intein::UB-mCherry-streptag (SEQ ID NO: 10) in the binary vector pE1775. The construct was stably transformed into tobacco NT1 cells via *Agrobacterium* co-cultivation. To test the processing in different plant species, the construct was also transiently expressed in the leaf tissues of *Nicotiana tabacum*, cv. *Xanthi* and *Nicotiana benthamiana* via agroinfiltration. The cellular extracts of transformed tissues/cells were subjected to western blot analysis to examine the processing of the polyprotein precursor. The in vivo protein auto-processing mediated by the intein:UB domain was confirmed by the detection of cleaved GFP1172 and mCherry-streptag on western blots probed with GFP and streptag (for downstream mCherry detection) antibodies, respectively. Characteristic GFP and mCherry fluorescence was observed in stably transformed NT1 extract (FIG. 20), indicating the processed proteins are functional. Based on the fluorescence measurement and fluorescence calibration curves for GFP and mCherry, stoichiometric production of the two proteins using the intein::UB cassette in a number of transgenic NT1 lines was confirmed. Additionally, the western blot result indicates correct processing of the polyprotein precursor into GFP and mCherry (FIG. 19).

Example 4

Intein-Intein

In this example, a Ssp PCC6803 DnaB mini-intein variant with C1A mutation to augment its C-terminal cleavage activity while abolishing its splicing activity was fused downstream of the N159A Ssp DnaE mini-intein variant to create the intein::intein, or dual intein, auto-processing cassette. To create this construct, the C-terminal cleaving DnaB intein domain was synthesized by PCR and substituted the F2A domain in the GFP172-intein::F2A-mCherry-streptag construct (SEQ ID NO: 14). The assembled intein::intein construct was mobilized into the plant expression binary vector pE1775 under the control of (ocs)3/mas super promoter, mammalian expression vector pcDNA3.1 under the control of cytomegalovirus (CMV) promoter, as well as in the *Escherichia coli* vector pUC57.

Figure 21:
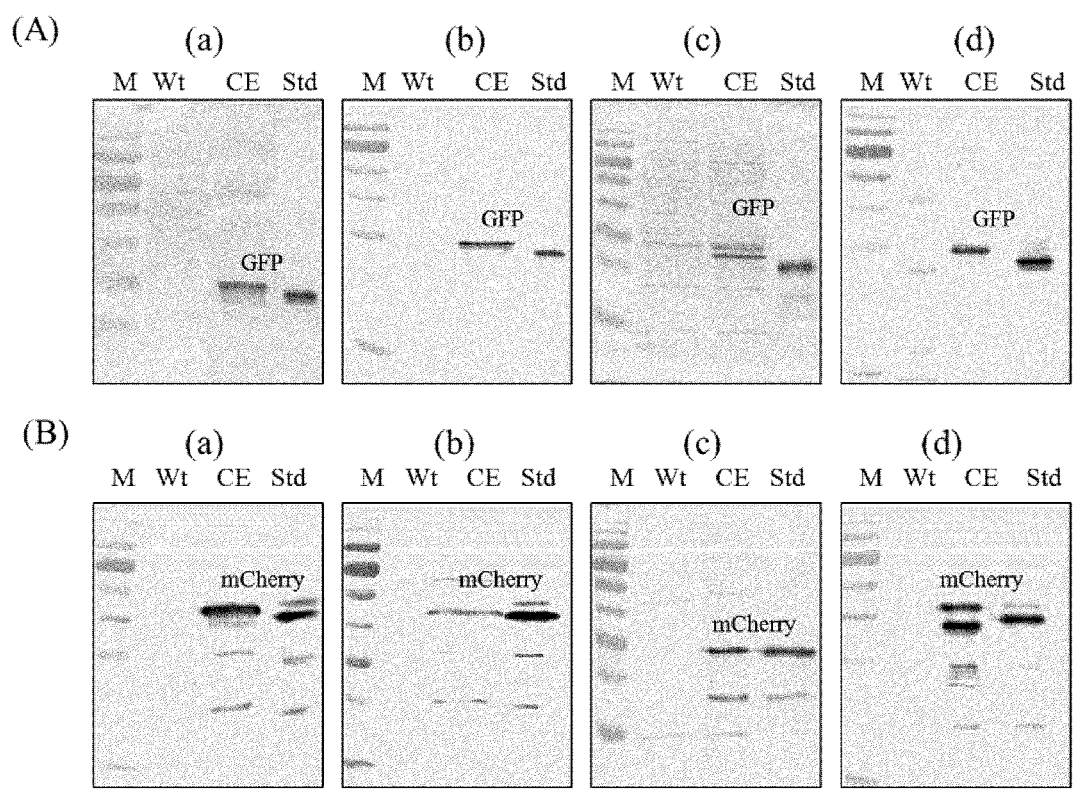
FIG. 21 illustrates Western blots illustrating the processing of intein::intein polyprotein in stably transformed NT1 cells (a), *N. benthamiana* leaf (b), mammalian HEK293 cells (c), and *Escherichia coli* (d), using anti-GFP (A), and anti-streptag (B) antibodies.
Figure 22:
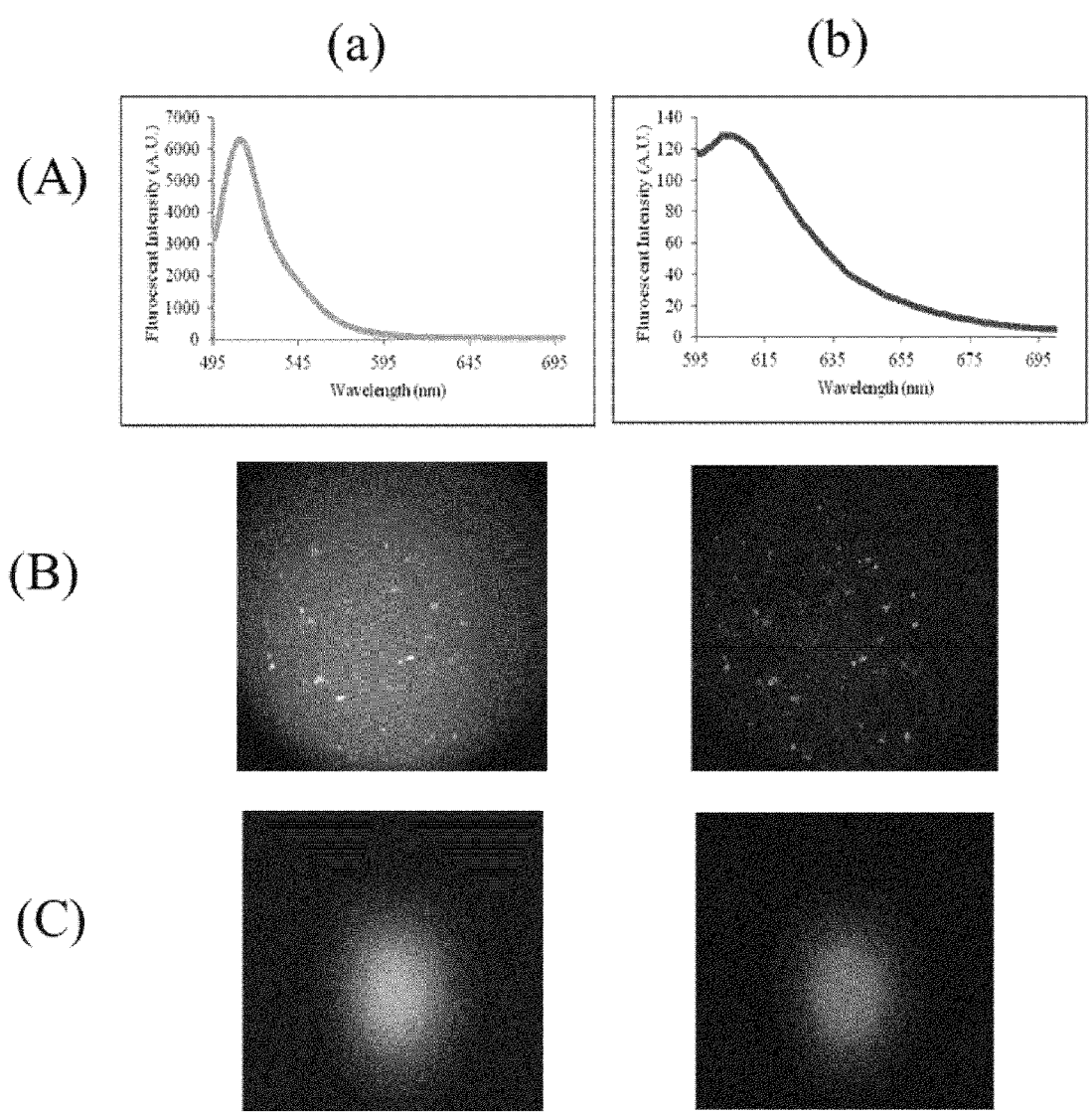
FIG. 22 illustrates fluorescence activity of GFP (a) and mCherry (b) released from intein::intein polyprotein precursor. (A): fluorescence spectra of NT1 extract; (B) & (C): fluorescence microscope images of transfected HEK293 cells and *E. coli* colony, respectively.

The plant construct was stably transformed into tobacco NT1 cells via *Agrobacterium* co-cultivation. The construct was also used to transiently transfect leaf tissues of *Nicotiana benthamiana* via agroinfiltraion. The mammalian construct was used to transfect HEK293T cells while the bacterial construct was introduced into *E. coli* via heat-shock transformation. The cellular processing of polyprotein precursor mediated by the intein::intein cassette in plant, mammalian and bacteria cells were characterized. The transformed cells were found to display both GFP and mCherry fluorescence. The processing of intein::intein polyprotein in different expression systems were examined using western blot analysis. As shown in FIGS. 21-22, both processed GFP and mCherry were detected in the extracts of all the tested tissues with no full length unprocessed fusion protein precursor or partially cleaved fragments. This finding supports the efficacy of the intein::intein auto-processing domain in all three host systems tested (i.e. plant, mammalian, and bacterial expression systems). In addition, characteristic GFP and mCherry fluorescence can be detected in all systems tested.

Example 5

Figure 23:
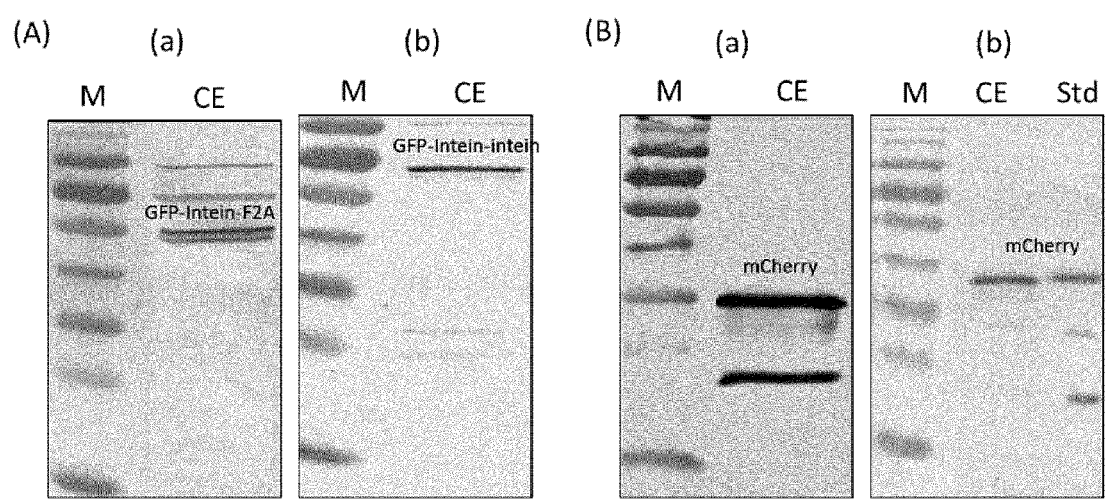
FIG. 23 illustrates Western blots illustrating the processing of inactive N-terminal cleaving intein in Intein::F2A (a) and Intein:Intein (b) polyprotein, using anti-GFP (A), and anti-streptag (B) antibodies.

Use an Intein Mutant with Impaired N-Terminal Cleavage Activity in the Intein::F2A or Intein::Intein Cassette in Tobacco Cells LED to Abolished N-Terminal Cleavage To confirm the N-terminal cleavage of the auto-processing cassette was attributed to the activity of the N-terminal cleaving intein mutant domain, an inactive Ssp DnaE mini-intein double mutant (C1A/N159A) (SEQ ID NO: 16) that abolishes both cleavage and splicing activities was used to replace the active intein domain in intein::F2A and intein::intein polyprotein constructs. The resulting constructs harboring the inactive intein variant were tested in stably transformed tobacco NT1. Although the cells still display proper GFP and mCherry fluorescence, there was no N-terminal cleavage noted based on the western blot analysis (FIG. 23). It is noted that only the first intein was inactivated and hence the C-terminal cleavage activity of the second intein is still preserved. This result confirms that the N-terminal cleaving intein in the active auto-processing cassette functions in the release of the upstream protein.

Example 6

Split-GFP Based Assay for the N-Terminal Cleavage Activity of Intein Mutants

The unique split-GFP screening scheme (FIG. 24) is aimed at selecting intein variants with high N-terminal autocleavage activity. As depicted in FIG. 24, in our proposed assay transsplicing between split DnaB (DB-c & DB-n) joins the two fragments of GFP11 (GFP11-n and GFP11-c represent N- and C-terminal fragments of GFP11, respectively) to form a complete GFP11 strand. With active mini-intein derivatives having high N-terminal cleavage activity, the spliced GFP11 becomes a peptide tag fused to the C-terminus of the intein and reconstitutes with GFP1-10 to form a fluorescent GFP, whereas for an inactive intein (with no N-terminal cleavage) the close distance between the two termini of intein puts a strain on the GFP11 and likely prevents it from reconstituting with the GFP1-10 to form a fluorescent protein. The split Ssp DnaB intein has been used for the synthesis of cyclic peptide in *E. coli* (Scott et al., 1999). Normally the most important flanking extein residue for effective splicing is the one at C+1. In the case of the DnaB intein, the native C+1 residue is Ser. To this end, a GFP11 mutant called M2 (L221H, F223S, T225N) showing improved reconstitution with GFP1-10 compared with wild-type GFP11 does contain a Ser residue in the middle of its sequence DHMVLHESVNAA (SEQ ID NO: 30) (Cabantous et al., 2005). Therefore we used the sequence DHMVLHE (SEQ ID NO: 31) as G11-n and SVNAA (SEQ ID NO: 32) as G11-c. We created two split-GF sensor constructs, one contains an active N159A DnaE mini-intein and the other contains a C1A/N159A inactive intein. When co-expressed with a GFP1-10 gene, *E. coli* expressing the active intein gave strong fluorescence while there was no fluorescence seen for inactive intein (FIG. 25). Western blot was also conducted to further verify the identity and processing of the sensor proteins (FIG. 25). The proposed split-GFP system has the advantage of being a "turn-on" sensor, i.e. lights up in positive clones, as opposed to "turn-off" sensors in which the signal is lost or reduced in positive clones, such as the FRET sensor reported in Amitai et al (Amitai et al., 2009), and that can potentially improve sensor sensitivity. Furthermore, the proposed design can potentially provide tight negative control and hence lowered background noise. We have also appended a RFP (red fluorescent protein mCherry) to the amino-terminus of the split-GFP sensor and showed that it allowed normalization of the sensor response (FIG. 26).

What is claimed is:

1. A method of expressing at least two separate polypeptides in a cell, the method comprising:
    initiating expression in the cell of two polypeptides of interest from a single polynucleotide encoding, from 5' to 3',
        a first polypeptide of interest;
        a processing unit downstream of the first polypeptide of interest and comprising an N-terminal autocatalytic cleavage domain upstream of a C-terminal cleavage domain; and
        a second polypeptide of interest downstream of the processing unit;
    wherein the N-terminal autocatalytic domain cleaves the first polypeptide of interest from the processing unit; and
    wherein the C-terminal cleavage domain cleaves the second polypeptide of interest from the processing unit,
    such that separate first and second polypeptides of interest are produced.

2. The method of claim 1, wherein the N-terminal autocatalytic cleavage domain comprises an intein, a B-type bacterial intein-like (BIL) domain, or a derivative thereof.

3. The method of claim 1, wherein the N-terminal autocatalytic cleavage domain comprises an intein that has no splicing activity, and that cleaves at an N-terminal, but not C-terminal end of the intein.

4. The method of claim 2, wherein the N-terminal autocatalytic domain hydrolyzes a peptide bond so that there is no amino acid overhang on a C terminus of the first polypeptide of interest.

5. The method of claim 1, wherein the method is performed in a eukaryotic cell.

6. The method of claim 2, wherein the first polypeptide is cleaved from the first N-terminal autocatalytic cleavage domain in a cellular location outside of the Golgi.

7. The method of claim 1, wherein the C-terminal cleavage domain comprises an intein.

8. The method of claim 2, wherein the C-terminal cleavage domain comprises a 2A sequence.

9. The method of claim 8, wherein the 2A sequence is a non-viral 2A sequence.

10. The method of claim 8, wherein the C-terminal cleavage domain further comprises at least one of SUMO or UB.

11. The method of claim 1, wherein the C-terminal cleavage domain comprises at least one of SUMO or UB.

12. The method of claim 1, wherein cleaving the second polypeptide of interest comprises hydrolyzing a peptide bond so that there is no amino acid overhang on an N terminus of the second polypeptide of interest.

13. The method of claim 1, wherein the first polypeptide of interest and second polypeptide of interest are expressed stoichiometrically.

14. The method of claim 1, wherein the polynucleotide encodes at least three polypeptides of interest, and wherein a processing unit is positioned between each two consecutive polypeptides of interest, and
    each of the at least three polypeptide of interest is cleaved from a processing unit adjacent thereto.

15. The method of claim 1, wherein the processing unit is encoded by a polynucleotide sequence comprising at least one of: SEQ ID NO: 41, SEQ ID NO: 43, SEQ ID NO: 45, SEQ ID NO: 47, SEQ ID NO: 51; SEQ ID NO: 53; or positions 760 to 1557 of SEQ ID NO: 26.

16. The method of claim 1, wherein the single polynucleotide comprises at least one of SEQ ID NO: 6, SEQ ID NO: 8, SEQ ID NO: 10, SEQ ID NO: 12, SEQ ID NO: 14, SEQ ID NO: 18; SEQ ID NO: 20; or SEQ ID NO: 26.

17. The method of claim 1, wherein the single polynucleotide of interest encodes a processing unit comprising at least one of SEQ ID NO: 42, SEQ ID NO: 44, SEQ ID NO: 46, SEQ ID NO: 48, SEQ ID NO: 52, SEQ ID NO: 54; or positions 245 to 510 of SEQ ID NO: 27.

18. The method of claim 1, wherein initiating expression comprises at least transfecting, transforming, or transducing the cell with the single polynucleotide.

19. A polynucleotide encoding, from 5' to 3':
a first polypeptide of interest;
a processing unit downstream of the first polypeptide of interest comprising:
  a N-terminal autocatalytic cleavage domain that can cleave a peptide bond between an N terminus of the N-terminal autocatalytic cleavage domain and a C terminus of the first polypeptide of interest so that there are no overhanging amino acid residues on a C terminus of the first polypeptide of interest after cleaving the peptide bond; and
  a C-terminal cleavage domain downstream of the N-terminal autocatalytic cleavage domain; and
a second polypeptide of interest downstream of the processing unit,
wherein the C-terminal cleavage domain can cleave a peptide bond between the C-terminal cleavage domain and the second polypeptide of interest.

20. The polynucleotide of claim 19, wherein the N-terminal autocatalytic cleavage domain comprises an intein.

21. The polynucleotide of claim 19, wherein the C-terminal cleavage domain is configured to cleave such that there is are no overhanging amino acid residues on an N terminus of the second polypeptide of interest.

22. The polynucleotide of claim 19, wherein the C-terminal cleavage domain comprises a 2A sequence.

23. The polynucleotide of claim 22, wherein the 2A sequence comprises a non-viral 2A sequence.

24. The polynucleotide of claim 21, wherein the C-terminal cleavage domain comprises a UB, SUMO, or furin site positioned immediately upstream of an N terminus of the second polypeptide of interest.

25. The polynucleotide of claim 19, further comprising a linker of about 3-40 amino acids in length positioned between the N-terminal autocatalytic cleavage domain and the C-terminal cleavage domain.

26. The polynucleotide of claim 19, wherein the C-terminal cleavage domain comprises an intein configured to have no splicing activity, and to cleave at an C-terminal, but not N-terminal end of the intein.

27. The polynucleotide of claim 19, wherein the C-terminal cleavage domain comprises a UB, SUMO, or furin site positioned immediately upstream of an N terminus of the second polypeptide of interest.

28. The polynucleotide of claim 19, wherein the first polypeptide of interest comprises a first subunit of a multimer, and the second polypeptide of interest comprises a second subunit of the multimer.

29. The polynucleotide of claim 19,
wherein the N-terminal autocatalytic cleavage domain comprises SEQ ID NO: 28, and
wherein the C-terminal cleavage domain comprises a 2A sequence of SEQ ID NO: 5.

30. The polynucleotide of claim 19, wherein the polynucleotide encodes a linker positioned downstream of the N-terminal autocatalytic cleavage domain, and upstream of and adjacent to the C-terminal cleavage domain, wherein the linker comprises about 3-40 amino acid residues.

31. The polynucleotide of claim 19, wherein the polynucleotide comprises at least one of: SEQ ID NO: 39, SEQ ID NO: 41, SEQ ID NO: 43, SEQ ID NO: 45, SEQ ID NO: 47, SEQ ID NO: 51; SEQ ID NO: 53; or positions 760 to 1557 of SEQ ID NO: 26.

32. The polynucleotide of claim 19, wherein the polynucleotide comprises at least one of SEQ ID NO: 6, SEQ ID NO: 8, SEQ ID NO: 10, SEQ ID NO: 12, SEQ ID NO: 14, SEQ ID NO: 18; SEQ ID NO: 20, or SEQ ID NO: 26.

33. The polynucleotide of claim 19, wherein the polynucleotide encodes a polypeptide comprising at least one of SEQ ID NO: 40, SEQ ID NO: 42, SEQ ID NO: 44, SEQ ID NO: 46, SEQ ID NO: 48, SEQ ID NO: 52, SEQ ID NO: 54; or positions 245 to 510 of SEQ ID NO: 27.

34. The polynucleotide of claim 19, wherein the polynucleotide is integrated into a genome of a eukaryotic host cell.

35. A polypeptide encoded by the polynucleotide of claim 19.

* * * * *

UNITED STATES PATENT AND TRADEMARK OFFICE
CERTIFICATE OF CORRECTION

PATENT NO. : 8,945,876 B2  
APPLICATION NO. : 13/683869  
DATED : February 3, 2015  
INVENTOR(S) : Wei Wen Su Page 1 of 1

It is certified that error appears in the above-identified patent and that said Letters Patent is hereby corrected as shown below:

In The Drawings

Sheet 5 of 38 (Reference Numeral 210, FIGURE 2) at line 1, Change "polynuclotide" to --polynucleotide--.

In The Specification

In column 4 at line 36 (approx.), Change "peptide" to --peptide.--.

In column 4 at line 43, Change "peptides" to --peptides.--.

In column 4 at line 50, Change "peptide" to --peptide.--.

In column 5 at line 11, Change "peptide" to --peptide.--.

In column 5 at line 14, Change "peptide" to --peptide.--.

In column 5 at line 28, Change "steptag" to --streptag--.

In column 5 at line 42, Change "antibody (b)" to --antibody (b).--.

In column 17 at line 20, Change "DUBS" to --DUBs--.

In column 29 at line 51 (approx.), Change "/nfb/" to --/nf.b/--.

In column 29 at line 51 (approx.), Change "htll11" to --htll1l--.

In column 29 at line 54 (approx.), Change "Bioi" to --Biol--.

In column 34 at line 6, Change "agroinfiltraion." to --agroinfiltration.--.

In The Claims

In column 129 at lines 37-38, In Claim 21, change "is are" to --are--.

Signed and Sealed this  
Twenty-sixth Day of January, 2016

Michelle K. Lee  
*Director of the United States Patent and Trademark Office*